US009632085B2

(12) United States Patent
Super et al.

(10) Patent No.: US 9,632,085 B2
(45) Date of Patent: Apr. 25, 2017

(54) RAPID ANTIBIOTIC SUSCEPTIBILITY TESTING

(71) Applicant: PRESIDENT AND FELLOWS OF HARVARD COLLEGE, Cambridge, MA (US)

(72) Inventors: Michael Super, Lexington, MA (US); Donald E. Ingber, Boston, MA (US); Mark J. Cartwright, West Newton, MA (US); Alexander Watters, North Andover, MA (US); John Samuel Workman, Seattle, WA (US); Daniel Levner, Boston, MA (US); Martin Marcus Rottman, St. Cloud (FR)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/382,043

(22) PCT Filed: Feb. 28, 2013

(86) PCT No.: PCT/US2013/028409
§ 371 (c)(1),
(2) Date: Aug. 29, 2014

(87) PCT Pub. No.: WO2013/130875
PCT Pub. Date: Sep. 6, 2013

(65) Prior Publication Data
US 2015/0064703 A1    Mar. 5, 2015

Related U.S. Application Data

(60) Provisional application No. 61/647,860, filed on May 16, 2012, provisional application No. 61/604,878, filed on Feb. 29, 2012.

(51) Int. Cl.
| | | |
|---|---|---|
| *G01N 33/53* | (2006.01) | |
| *G01N 33/569* | (2006.01) | |
| *C12Q 1/18* | (2006.01) | |

(52) U.S. Cl.
CPC ......... *G01N 33/56938* (2013.01); *C12Q 1/18* (2013.01); *G01N 33/56911* (2013.01); *G01N 33/56916* (2013.01); *G01N 2333/245* (2013.01); *G01N 2333/31* (2013.01); *G01N 2500/10* (2013.01)

(58) Field of Classification Search
CPC ............................ C12Q 1/18; G01N 33/56938
USPC ......................................... 435/35, 6.12, 7.32
See application file for complete search history.

(56) References Cited

U.S. PATENT DOCUMENTS

| | | |
|---|---|---|
| 5,137,810 A | 8/1992 | Sizemore et al. |
| 5,270,199 A | 12/1993 | Ezekowitz |
| 5,545,820 A | 8/1996 | Gatehouse et al. |
| 5,789,173 A | 8/1998 | Peck et al. |
| 5,951,976 A | 9/1999 | Segal |
| 6,117,977 A | 9/2000 | Lasky et al. |
| 6,184,027 B1 * | 2/2001 | Laine ............... C07K 14/001 435/261 |
| 6,225,046 B1 | 5/2001 | Vesey et al. |
| 6,503,761 B1 | 1/2003 | Koenig et al. |
| 6,528,624 B1 | 3/2003 | Idusogie et al. |
| 6,562,784 B1 | 5/2003 | Thiel et al. |
| 6,733,753 B2 | 5/2004 | Boone et al. |
| 6,846,649 B1 | 1/2005 | Thiel et al. |
| 6,900,292 B2 | 5/2005 | Sun et al. |
| 7,202,207 B2 | 4/2007 | Thiel et al. |
| 7,211,396 B2 | 5/2007 | Uttenthal |
| 7,226,429 B2 | 6/2007 | Tullis |
| 7,439,224 B2 | 10/2008 | Thiel et al. |
| 7,462,596 B2 | 12/2008 | Larsen et al. |
| 7,695,937 B2 | 4/2010 | Baum et al. |
| 7,763,436 B2 | 7/2010 | Das et al. |
| 8,080,245 B2 | 12/2011 | Visintin et al. |
| 8,084,275 B2 | 12/2011 | Hirai et al. |
| 8,088,596 B2 | 1/2012 | Zeng et al. |
| 8,415,118 B2 | 4/2013 | Huang et al. |
| 2003/0162248 A1 | 8/2003 | Wakamiya |
| 2003/0166878 A1 | 9/2003 | Nishiya et al. |
| 2004/0229212 A1 | 11/2004 | Thiel et al. |
| 2005/0014932 A1 | 1/2005 | Imboden et al. |

(Continued)

FOREIGN PATENT DOCUMENTS

| | | | |
|---|---|---|---|
| EP | 0861667 A2 | 9/1998 | |
| EP | 0915970 B1 | 9/2004 | |
| EP | 1812459 B1 | 3/2011 | |
| WO | 8901519 A1 | 2/1989 | |
| WO | 00/23792 * | 4/2000 | ............ G01N 21/77 |
| WO | 0232292 A2 | 4/2002 | |
| WO | 03014150 A2 | 2/2003 | |
| WO | 03054164 A2 | 7/2003 | |
| WO | 2004018698 A2 | 3/2004 | |
| WO | 2007/001332 * | 1/2007 | ............ A61K 38/17 |

(Continued)

OTHER PUBLICATIONS

Witus, Leah S e tal, JACS Articles, published on line Nov. 10, 2010, Identification of highly reactive sequences ofPLP-mediated bioconjugation using a combinatorial Peptide Library, Journal of the American Chemical Society, vol. 132, 2010, pp. 16812-16817.*

(Continued)

*Primary Examiner* — Albert Navarro
(74) *Attorney, Agent, or Firm* — Nixon Peabody LLP

(57) ABSTRACT

Embodiments of various aspects described herein are directed to methods, compositions, kits and systems for rapid determination of antibiotic susceptibility of a microbe within hours after a sample is collected. In some embodiments, the methods, compositions, kits and systems described herein can allow determination of antibiotic susceptibility of a microbe based on a small number of microbes, e.g., as few as 5-10 microbes bound to a microbe-targeting substrate described herein.

26 Claims, 17 Drawing Sheets

(56) References Cited

U.S. PATENT DOCUMENTS

| | | |
|---|---|---|
| 2005/0037949 A1 | 2/2005 | O'Brien et al. |
| 2005/0095665 A1 | 5/2005 | Williams et al. |
| 2005/0277170 A1 | 12/2005 | Black et al. |
| 2006/0040362 A1 | 2/2006 | Wakamiya |
| 2006/0104975 A1 | 5/2006 | Geijtenbeek et al. |
| 2006/0177879 A1 | 8/2006 | Mayes et al. |
| 2006/0188963 A1 | 8/2006 | Kongerslev et al. |
| 2006/0251580 A1 | 11/2006 | Keppler et al. |
| 2007/0037225 A1 | 2/2007 | Metzger et al. |
| 2007/0224640 A1 | 9/2007 | Dahlgren Caldwell et al. |
| 2007/0269818 A1 | 11/2007 | Savage |
| 2007/0269878 A1 | 11/2007 | Gerard et al. |
| 2008/0156736 A1 | 7/2008 | Hirai et al. |
| 2008/0182793 A1 | 7/2008 | Baum |
| 2008/0193965 A1 | 8/2008 | Zeng et al. |
| 2009/0181041 A1 | 7/2009 | Holgersson et al. |
| 2009/0220932 A1 | 9/2009 | Ingber et al. |
| 2009/0297516 A1 | 12/2009 | Mayo et al. |
| 2010/0266558 A1 | 10/2010 | Zipori |
| 2010/0323429 A1 | 12/2010 | Hu et al. |
| 2010/0331240 A1 | 12/2010 | Michelow et al. |
| 2011/0027267 A1 | 2/2011 | Kyneb et al. |
| 2011/0053145 A1 | 3/2011 | Takakura et al. |
| 2011/0053250 A1 | 3/2011 | Takakura et al. |
| 2011/0159000 A1 | 6/2011 | Silverman |
| 2011/0183398 A1 | 7/2011 | Dasaratha et al. |
| 2011/0281792 A1 | 11/2011 | Zion et al. |
| 2012/0164628 A1 | 6/2012 | Duffin et al. |
| 2014/0227723 A1* | 8/2014 | Ingber ............ A61K 47/48369 435/7.92 |

FOREIGN PATENT DOCUMENTS

| | | | | |
|---|---|---|---|---|
| WO | 2007/001332 A2 | | 1/2007 | |
| WO | 2007044642 A2 | | 4/2007 | |
| WO | 2008/095905 | * | 8/2008 | ........... G01N 33/566 |
| WO | 2008130618 A1 | | 10/2008 | |
| WO | 2009062195 A2 | | 5/2009 | |
| WO | 2009/079232 | * | 6/2009 | ............... C12Q 1/68 |
| WO | 2009126346 A2 | | 10/2009 | |
| WO | 2010/114727 | * | 10/2010 | ............... C12M 1/12 |
| WO | 2011/090954 | * | 7/2011 | ............... C07K 19/00 |
| WO | 2011/090954 A2 | | 7/2011 | |
| WO | 2011/091037 | * | 7/2011 | ............. G01N 35/08 |
| WO | 2011091037 A2 | | 7/2011 | |
| WO | 2012100099 A2 | | 7/2012 | |
| WO | 2012/135834 | * | 10/2012 | ........... G01N 33/569 |
| WO | 2012135834 A2 | | 10/2012 | |
| WO | 2013012924 A2 | | 1/2013 | |
| WO | 2014014788 A2 | | 1/2014 | |

OTHER PUBLICATIONS

Chem, Mu-Lin e tal, Fabrication of an Oriented Fc-Fused Lectin Microarray through boronate Foirmation, Angew. Chem. Int. Ed. 2008, vol. 47, pp. 8627-8630.*

Lin, Ya-Shivan et al, Affinity Capture using Vancomycin-Bound Magnetic nanoparticles of the MALDI-MS Analysis of Bacteria, Anal. Chem. vol. 77, pp. 1753-1760, 2005.*

Arakawa et al., "Elution of antibodies from a protein-A column by aqueous arginine solutions." Protein Expression and Purification 36:244-248 (2004).

Armour et al., "Recombinant human IgG molecules lacking Fcgamma receptor I binding and monocyte triggering activities." Eur. J. Immunol. 29:2613-2624 (1999).

Ashkenazi et al., "Immunoadhesins as research tools and therapeutic agents," Curr. Opin. Immunol. 9(2):195-200 (1997).

Bangs Laboratories, Inc., "Protein Coated Microspheres", Tech. Note #51 (1997).

Bayston et al., "Bacterial endotoxin and current concepts in the diagnosis and treatment of endotoxaemia", J. Med. Microbiol. 31:73-83 (1990).

Bossola et al., "Circulating Bacterial-Derived DNA Fragments and Markers of Inflammation in Chronic Hemodialysis Patients." Clin J. Am. Soc. Nephrol. 4:379-385 (2009).

Brooks et al., "Expression and secretion of ficolin beta by porcine neutrophils", Biochim. Biophys. Acta 1624 (1-3):36-45 (2003).

Brouwer et al., "Mannose-Binding Lectin (MBL) Facilitates Opsonophagocytosis of Yeasts but Not of Bacteria despite MBL Binding", J. Immunol. 180(6):4124-4132 (2008).

Chamow et al., "Immunoadhesins: principles and applications", Trends Biotechnol. 14(2):52-60 (1996).

Chang et al., "Crystallization and Preliminary X-ray Analysis of a Trimeric Form of Human Mannose Binding Protein." J. Mol. Biol. 241:125-127 (1994).

Chen et al., "Fabrication of an Oriented Fc-Fused Lectin Microarray through Boronate Formation", Angew. Chem. Int. Ed., 47:8627-8630 (2008).

Ellsaesser et al., "A new method for the cytochemical staining of cells immobilized in agarose", Histochemistry 80:559-562 (1984).

Eun et al., "Encapsulating bacteria in agarose microparticles using microfluidics for high-throughput cell analysis and Isolation", ACS Chem Biol. 6(3):260-266 (2011).

Foster, "Immune Evasion by Staphylococci", Nature 3:948-958 (2005).

Fox et al., "Single amino acid substitutions on the surface of *Escherichia coli* maltose-binding protein can have a profound impact on the solubility of fusion proteins", Protein Sci. 10(3):622-630 (2001).

Frakking et al., "Safety and phamacokinetics of plasma-derived mannose-binding lectin (MBL) substitution in children with chemotherapy-induced neutropaenia", Eur. J. Cancer 45(4):505-512 (2009).

Garnacho-Montero "Timing of adequate antibiotic therapy is a greater determinant of outcome than are TNF and IL-10 polymorphisms in patients with sepsis", et al., Crit. Care 10(4):R111 (2006).

Garred et al., "Mannose-binding lectin and its genetic variants", Genes and Immunity 7(2):85-94 (2006).

Grogl et al., "Leishmania braziliensis: Protein, Carbohydrate, and Antigen Differences between Log Phase and Stationary Phase Promastigotes in Vitro", Exp. Parasitol. 63(3):352-359 (1987).

Hinton et al., "Engineered Human IgG Antibodies with Longer Serum Half-lives in Primates", J. Biol. Chem. 279(8):6213-6216 (2004).

Holmskov et al., "Affinity and kinetic analysis of the bovine plasma C-type lectin collectin-43 (CL-43) interacting with mannan", FEBS Lett. 393(2-3):314-316 (1996).

Huang et al., "Porcine DC-SIGN: Molecular cloning, gene structure, tissue distribution and binding characteristics", Dev. Comp. Immunol. 33(4):464-480 (2009).

Hwang et al., "The Pepper Mannose-Binding Lectin Gene CaMBL1 is Required to Regulate Cell Death and Defense Responses to Microbial Pathogens", Plant Physiol. 155(1):447-463 (2011).

Idusogie et al., "Engineered Antibodies with Increased Activity to Recruit Complement", J. Immunol. 166 (4):2571-2575 (2001).

Invivo Gen Insight, "IgG-Fc Engineering for Therapeutic Use." Apr./May 2006.

Jack et al., "Mannose-binding lectin: targeting the microbial world for complement attack and opsonophagocytosis", Immunol. Rev. 180:86-99 (2001).

Jarva et al., "*Streptococcus pneumoniae* Evades Complement Attack and Opsonophagocytosis by Expressing the pspC Locus-Encoded Hic Protein That Binds to Short Consensus Repeats 8-11 of Factor H", J. Immunol. 168(4):1886-1894 (2002).

Kang et al., "The human macrophage mannose receptor directs *Mycobacterium tuberculosis* lipoarabinomanan-mediated phagosome biogenesis", J. Exp. Med. 202(7):987-999 (2005).

Keen et al., "Interrelationship Between pH and Surface Growth of Nitrobacter." Soil Biol. Biochem. 19(6):665-672 (1987).

Kehres, "A kinetic model for binding protein-mediated arabinose transport", Protein Sci. 1(12):1661-1665 (1992).

Krarup et al., "Simultaneous Activation of Complement and Coagulation by MBL-Associated Serine Protease 2", PLoS ONE, 2(7):e623 (2007).

(56) References Cited

OTHER PUBLICATIONS

Kumar, "Optimizing Antimicrobial Therapy in Sepsis and Septic Shock", Crit. Care Clin. 25(4):733-751 (2009).
Linehan et al., "Endogenous ligands of carbohydrate recognition domains of the mannose receptor in murine macrophages, endothelial cells and secretory cells; potential relevance to inflammation and immunity", Eur. J. Immun. 31:1857-1866 (2001).
Lo et al., "High level expression and secretion of Fc-X fusion proteins in mammalian cells", Protein Eng. 11(6):495-500 (1998).
Loosdrecht et al., "Influence of interfaces on microbial activity." Microbiological Reviews 54(1):75-87 (1990).
Matsushita et al., "Activation of the Classical Complement Pathway by Mannose-binding Protein in Association with a Novel C1s-like Serine Protease", J. Exp. Med. 176(6):1497-1502 (1992).
Michelow et al., "A Novel L-ficolin/Mannose-binding Lectin Chimeric Molecule with Enhanced Activity against Ebola Virus", J. Biol. Chem. 285(32):24729-24739 (2010).
Nadesalingam et al., "Mannose-Binding Lectin Recognizes Peptidoglycan via the N-Acetyl Glucosamine Moiety, and Inhibits Ligand-Induced Proinflammatory Effect and Promotes Chemokine Production by Macrophages", J. Immunol. 175:1785-1794 (2005).
Nakamura et al., "Characterization of the interaction between serum mannan-binding protein and nucleic acid ligands", J. Leukocyte Biol. 86:737-748 (2009).
Neth et al., "Ehancement of Complement Activation and Opsonophagocytosis by Complexes of Mannose-Binding Lectin with Mannose-Binding Lectin-Associated Serine Protease After Binding to *Staphylococcus aureus*", J. Immunol. 169:4430-4436 (2002).
Neth et al., "Mannose-Binding Lectin Binds to a Range of Clinically Relevant Microorganisms and Promotes Complement Deposition", Infect. Immun. 68(2):688-693 (2000).
Nisnevitch et al., "The solid phase in affinity chromatography: strategies for antibody attachment", J. Biochem. Thophys. Methods 49:467-480 (2001).
Ogden et al., "Gig and Mannose Binding Lectin Engagement of Cell Surface Calreticulin and CD91 Initiates Macropinocytosis and Uptake of Apoptotic Cells", J. Exp. Med. 194:781-795 (2001).
Perham, "Domains, Motifs, and Linkers in 2-Oxo Acid Dehydrogenase Multienzyme Complexes: A Paradigm in the Design of a Multifunction Protein", Biochemistry 30(35):8501-8512 (1991).
Product Data Sheet, "Human Mannan Binding Lectin peptide (237-248) (Carboxyterminal end) ab45655".
Rutishauser et al., "Amino Acid Sequence of the Fc Region of a Human yG Immunoglobulin", Biochemistry 61:1414-1421 (1968).
Safarik et al., "The application of magnetic separations in applied microbiology", J. Appl. Bacteriol. 78:575-585 (1995).
Schmidt, "Fusion proteins as biopharmaceuticals—Applications and challenges", Curr. Opin. Drug Discov. Devel. 12(2):284-295 (2009).
Shields et al, "High Resolution Mapping of the Binding Site on Human IgG1 for Fc gamma RI, Fc gamma RII, Fc gamma RIII, and FcRn and Design of IgG1 Variants with Improved Binding to the Fc gamma R", J. Biol. Chem. 276(9):6591-6604 (2001).
Sprong et al., "Mannose-Binding Lectin Is a Critical Factor in Systemic Complement Activation during Meningococcal Septic Shock", Clin. Infect. Dis. 49(9):1380-1386 (2009).
Steurer et al., "Ex Vivo Coating of Islet Cell Allografts with Murine CTLA4/Fc Promotes Graft Tolerance", J. Immunol. 155(3):1165-1174 (1995).
Stuart et al., "Mannose-Binding Lectin-Deficient Mice Display Defective Apoptotic Cell Clearance but No Autoimmune Phenotype", J. Immunol. 174:3220-3226 (2005).
Takahashi et al., "Mannose-binding lectin and its associated proteases (MASPs) mediate coagulation and its deficiency is a risk factor in developing complications from infection, including disseminated intravascular coagulation", Immunobiology 216(1-2):96-102 (2011).
Terai et al., "Relationship between gene polymorphisms of mannose-binding lectin (MBL) and two molecular forms of MBL", Eur. J. Immunol., 33:2755-2763 (2003).
Thiel et al., "A second serine protease associated with mannan-binding lectin that activates complement", Nature 386:506-510 (1997).
Vaccaro et al., "Engineering the Fc region of immunoglobulin G to modulate in vivo antibody levels", Nat. Biotechnol. 23(10):1283-1288 (2005).
Ward et al, "Characterization of Humanized Antibodies Secreted by Aspergillus niger", Appl. Environ. Microbiol. 70(5):2567-2576 (2004).
Warwick et al., "Use of Quantitative 16S Ribosomal DNA Detection for Diagnosis of Central Vascular Catheter-Associated Bacterial Infection", J. Clin. Microbiol. 42(4):1402-1408 (2004).
Witus et al., "Identification of Highly Reactive Sequences for PLP-Mediated Bioconjugation Using a Combinatorial Peptide Library", J. Am. Chem. Soc. 132(47):16812-16817 (2010).
Wong et al., "Bioinspired self-repairing slippery surfaces with pressure—stable omniphobicity." Nature 477:443-447 (2011).
Wriggers et al., "Control of Protein Functional Dynamics by Peptide Linkers", Biopolymers 80(6):736-746 (2005).
Xia et al., "Combined microfluidic-micromagnetic separation of living cells in continuous flow", Biomed. Microdevices 8(4):299-308 (2006).
Ye et al., "Surface display of a glucose binding protein", Journal of Molecular Catalysis B: Enzymatic 28(4-6):201-206 (2004).
Yung et al., "Micromagnetic-microfluidic blood cleansing device", Lab Chip 9(9):1171-1177 (2009).

\* cited by examiner

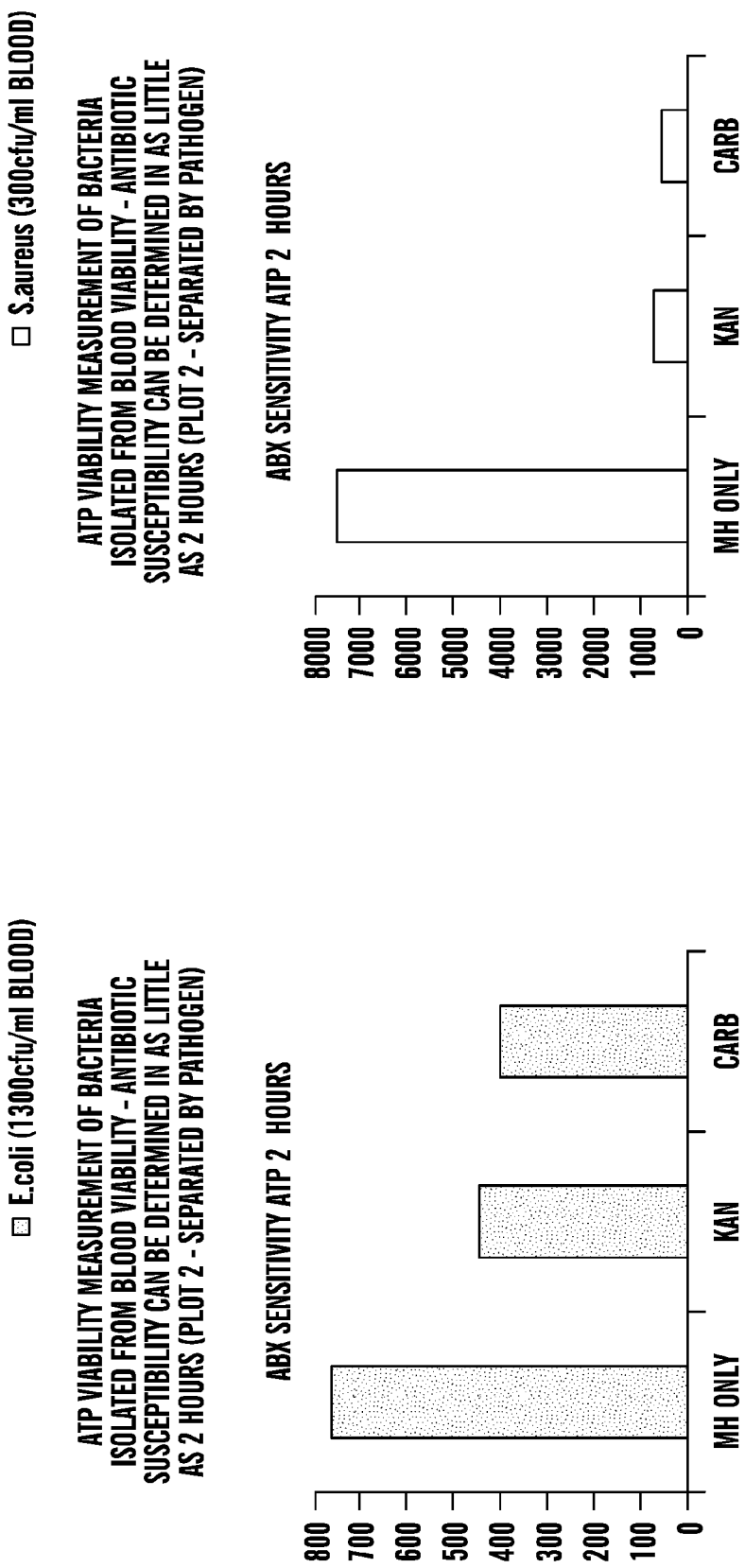

RAPID ANTIBIOTIC SUSCEPTIBILITY TESTING

CROSS REFERENCE TO RELATED APPLICATIONS

This Application is a 35 U.S.C. §371 National Phase Entry Application of International Application No. PCT/US2013/028409 filed Feb. 28, 2013, which designates the U.S., and which claims the benefit under 35 U.S.C. §119(e) of U.S. Provisional Application No. 61/604,878 filed Feb. 29, 2012; and 61/647,860 filed May 16, 2012, the contents of which are herein incorporated by reference in their entirety.

GOVERNMENT SUPPORT

This invention was made with government support under grant no. N66001-11-1-4180 awarded by DARPA. The government has certain rights in the invention.

SEQUENCE LISTING

The instant application contains a Sequence Listing which has been submitted electronically in ASCII format and is hereby incorporated by reference in its entirety. Said ASCII copy, created on Sep. 15, 2014, is named 002806-071742-US_SL.txt and is 18,676 bytes in size.

TECHNICAL FIELD

The present disclosure relates to methods, compositions and kits for rapid determination of antibiotic susceptibility of a microbe within hours after sample collection.

BACKGROUND OF THE DISCLOSURE

Every year more than 18 million patients experience sepsis caused by systemic blood-borne infection, and more than 6 million of these people die. Mortality rates from sepsis in intensive-care units range from 20 to 60% worldwide, and one retrospective study revealed that 20% of patients with septic shock were initially treated with inappropriate antibiotic therapy (Kumar et al., Chest 2009; 25: 733). This is largely because it takes days to obtain a rigorous diagnosis of pathogen type, even in state-of-the art clinical microbiology laboratories. Moreover, patients who initially receive incorrect therapies exhibit a 5-fold lower survival rate than those who are treated with optimal therapy from early in the course of the disease. In fact, in one study it was shown that the risk for in-hospital mortality increased by 9% for every hour of delay before the correct antibiotic regimen was administered (Garnacho-Montero et al., Critical Care 2006; 10:R111). Thus, the speed of pathogen diagnosis in a patient with a blood-borne microbial infection can mean the difference between life and death. The current state-of-the-art for detection of a microbial infection in blood, which has essentially remained unchanged for the past thirty years, is to culture the blood in a hospital or commercial clinical microbiology laboratory. Liquid cultures can permit detection of the existence of some type of growing organism in the fluid within 16 to 30 hours (based on the analysis of more than 50,000 blood cultures carried out in one year at the Brigham and Women's Hospital clinical microbiological laboratory). This assay is not quantitative and without knowledge of the type of pathogen and their specific antibiotic sensitivities, only wide-spectrum antibiotics can be administered at this time, which are suboptimal at best. To identify the specific type of pathogen, and to carry out sensitivity testing to determine their responses to various potential antibiotic therapies, the pathogens growing in liquid medium must then be transferred to other growth media (e.g., agar plates). The total time for full diagnosis and sensitivity testing is commonly 3-7 days and empiric antibiotic treatment based on clinical symptoms is started well before the results of the antibiotic sensitivity are obtained, often within 1-3 hours after blood cultures are first drawn from the patient.

Many patients with septicemia or suspected septicemia exhibit a rapid decline over a 24-48 hour period. Thus, rapid and reliable diagnostic and treatment methods are essential for effective patient care. Unfortunately, current antimicrobial susceptibility testing techniques generally require a prior isolation of the microorganism by culture (e.g., about 12 to about 48 hours), followed by a process that requires another about 6 to about 24 hours. For example, a confirmed diagnosis as to the type of infection, traditionally requires microbiological analysis involving inoculation of blood cultures, incubation for 16-24 hours, plating the causative microorganism on solid media, another incubation period, and final identification 1-2 days later. Even with immediate and aggressive treatment, many patients develop multiple organ dysfunction syndrome and eventually death.

Every hour lost before a correct treatment is administered can make a crucial difference in patient outcome. Consequently, it is important for physicians to determine rapidly if the patient indeed has sepsis, and if so, what antibiotics would be effective for the treatment. For example, an appropriate antimicrobial therapy that can be instated within 6 hours of the onset of sepsis can positively impact patient outcome. However, the current practice, i.e., blood culture, takes two days or more to yield an answer, which quite often proves too long. Accordingly, there is a strong need for a more rapid antibiotic sensitivity testing, preferably one that can identify specific antibiotic susceptibilities within only a few hours after blood samples are first drawn. A rapid test of this type would therefore permit physicians to initiate the optimal drug therapy from the start, rather than starting with a suboptimal or completely ineffective antibiotic, hence greatly increasing clinical responsiveness.

SUMMARY

Existing antimicrobial susceptibility testing (AST) techniques generally require the prior isolation of the microorganism by culture (~12 to ~48 hours) followed by a process that requires another 6 to 24 hours. However, adapted antimicrobial therapy in the first few hours of septic shock is a key predictor for survival. Thus, there is a strong need for rapid antimicrobial susceptibility testing. Inventors have discovered inter alia that antibiotic susceptibility of a microbe can be determined within hours after a sample is collected. In one embodiment, the antibiotic susceptibility test or assay can be completed in less than 6 hours. The method can be used with or without first identifying the microbe. Additionally, while existing AST technology generally relies on an analysis of large bacterial populations (e.g., $\sim 10^5$ to $\sim 10^7$ CFU) obtained from a culture, the inventors have discovered inter alia that antibiotic susceptibility of a microbe can be determined by concentrating the microbe from a biological sample prior to culture and performing single cell analysis of susceptibility to one or more antibiotic agents. Accordingly, disclosed herein is an assay for rapidly determining antibiotic susceptibility of a microbe. Aspects of the assay are based on the rapid separation and concentration of microbes from a biological sample, e.g., biological fluid. Generally the assay comprises obtaining a microbe extracted from a biological source and determining the growth or a functional response of the microbe in presence of an antibiotic agent. Reduced growth or functional response in the presence of the antibiotic agent relative to a control indicates that the microbe is susceptible to the antibiotic agent tested. In addition, the assay can also carry antibiotic susceptibility testing in a small number of microbes (as few as 300 in a sample). In some embodiments, the assay can allow determination of susceptibility of one or more microbes or microorganisms to at least one antibiotic agent (including antimicrobial agent) from single microbes or microorganisms (e.g., as few as about 5-10 live microbes). In some embodiments, the assay described herein can be performed in as a little as three hours of specimen reception. The capability of determining susceptibility of a microbe or microorganism to an antibiotic agent using a small number of the microbe (e.g., as few as about 5-10 live microbes or lower) can be desirable because clinical samples of biological fluids (e.g., blood, cerebral spinal fluid, etc.) can have only rare microbes (<100/mL) and they are often limited in volume to only a few milliliters or less.

In addition, embodiments of the method utilizing Mannose Binding Lectin (MBL) and genetically engineered version of MBL (FcMBL and Akt-FcMBL) as broad-spectrum microbe binding molecules to capture and grow the microbes, can be carried out without identifying the microbe, either for extraction or for antibiotic sensitivity testing.

In some embodiments, the biological fluid is collected or derived from a subject who is suspected of having a microbial infection. Further, once an antibiotic agent resistance is established, a practitioner can select a treatment regimen for the subject afflicted with the microbes. For example, the treatment regime can comprise administering to the subject one or more antibiotic agents to which the microbe showed susceptibility.

BRIEF DESCRIPTION OF THE DRAWINGS

FIGS. 11A-11D are bar graphs showing ATP viability measurement of bacteria isolated from blood. Viability or antibiotic susceptibility can be determined in as little as 2 hours.

FIG. 12A, Bead 1: Akt-FcMBL; Bead 2:1:1 ratio–Akt-FcMBL: Biotin heparin; Bead 3: Heparin cross-linked to Akt-FcMBL directly; and Bead 4: Heparin only. FIG. 12B, Bead 1: AOB Akt-FcMBLcoupled beads (AOB=aminooxybiotin); Bead 2:1:1 ratio–AOB Akt-FcMBL: Biotin heparin coupled beads; Bead 3: Heparin Beads+AKT-FcMBL-1 um beads conjugated with heparin, then coupled with AOB AKT-FcMBL; Bead 4: AKTFcMBL Beads-heparin—Previously coupled AOB AKT-FcMBL beads are conjugated with heparin; Bead 5: Heparin conjugated to Akt-FcMBL directly and coupled to 1 uM beads; and Bead 6: Heparin conjugated beads.

FIGS. 14C and 14D are corrected for blood/bead background.

DETAILED DESCRIPTION OF THE INVENTION

Figure 1:
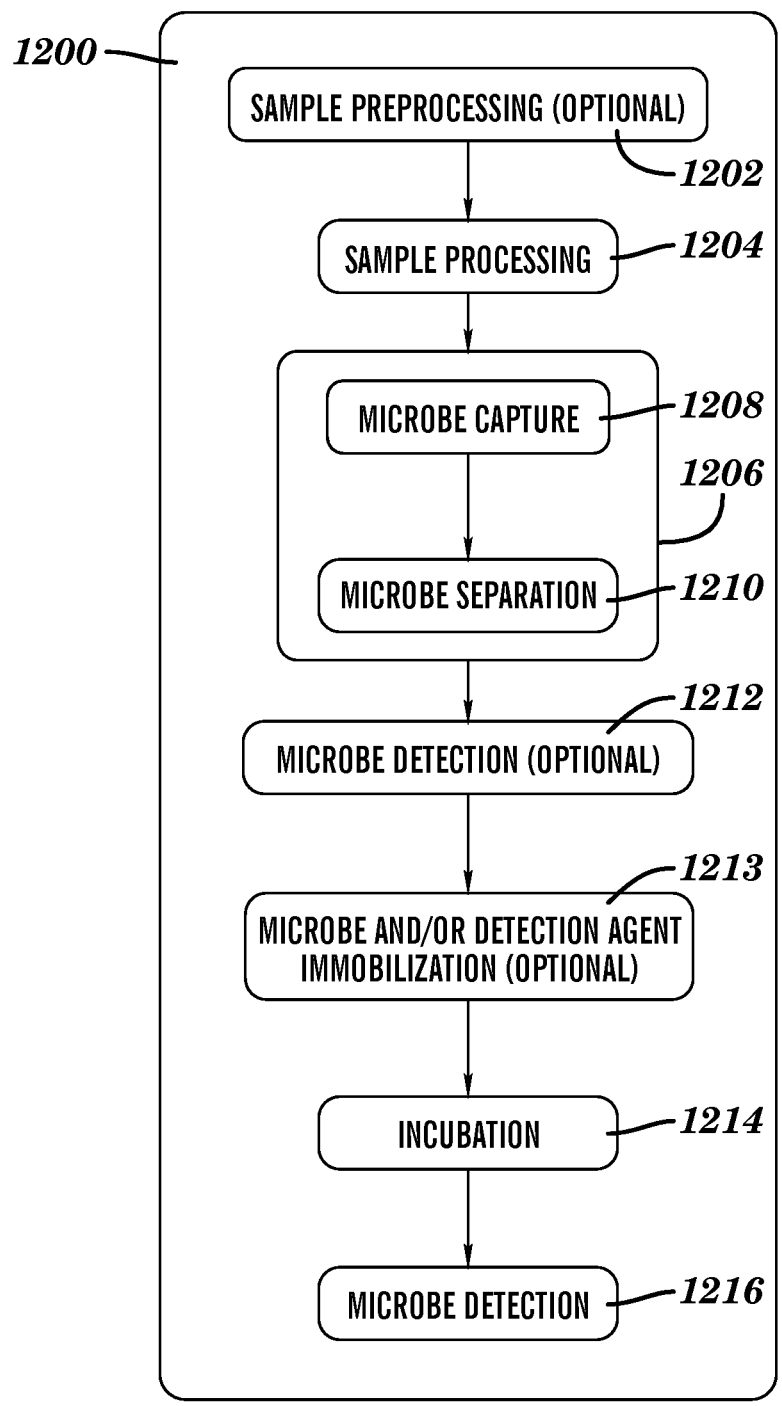
FIG. 1 is a schematic of the process described herein.

Inventors have discovered inter alia that antibiotic susceptibility of a microbe (e.g., a pathogen) can be determined within hours after a sample is collected. The method can be used with or without first identifying the microbe. Accordingly, disclosed herein is an assay for determining antibiotic susceptibility of a microbe. The assay comprises providing a sample suspected of comprising a microbe extracted from a test sample, such as a biological source (e.g. a biological fluid), and determining the growth or a functional response of the microbe in the presence of an antibiotic agent. Reduced growth or functional response in the presence of the antibiotic agent relative to a control indicates that the microbe is susceptible to the antibiotic agent tested.

Generally, the method comprises: (i) extraction and concentration of microbes from a biological fluid, e.g., blood; (ii) splitting into subsamples and incubation with antibiotic-supplemented media (Yeast extract free media for ELISA or other for Luciferase based assay); and (iii) detection of microbe growth or a functional response. The microbe can be extracted from the test sample using a microbe-targeting substrate, i.e., a solid substrate coated with microbe-binding molecules. Microbe-targeting substrates and microbe-binding molecules are described in more detail below. Additionally, while the method is described in relation to biological fluids, the method can be practiced with any test sample, e.g., biological fluids; fluids from a culture, e.g., blood culture; a sample taken from a colony; and/or a sample taken from any environmental source, e.g., but not limited to, food products, water, ponds, food processing plants.

Without wishing to be bound by a theory, the antibiotic susceptibility testing method described herein can detect microbial infection of blood or septicemia caused by different pathogens (e.g., bacteremia, fungemia, viremia) and provide the antibiotic sensitivity and resistance profile of the causative agent (e.g., microbial pathogen) in less than 48 hours, less than 24 hours, less than 12 hours, less than 10 hours, less than 8 hours, less than 6 hours, less than 4 hours, less than 3 hours, less than 2 hours, less than 1 hour, less than 30 mins, less than 15 mins, or lower. In some embodiments, the antibiotic susceptibility testing described herein can detect septicemia and provide the antibiotic sensitivity and resistance profiles of the causative agent (e.g., microbe or pathogen) in less than 6 hours, less than 4 hours, less than 3 hours, less than 2 hours, less than 1 hour, less than 30 mins, less than 15 mins, or lower.

In addition, as described below, the method can be carried out without having to identify the microbe (e.g., pathogen) either for extraction or for incubation with an antibiotic agent. For example, the microbe can be extracted from the test sample using a substrate coated with a broad-spectrum microbe-binding molecule. Various microbe-binding molecules are described in more detail below.

In some embodiments, the assay described herein is based on the direct measurement of bacteria's ability to grow in the presence of the tested antibiotic agents. This direct measurement can provide the clinically relevant result that a physician seeks and is thus superior to methods that test for indirect properties, e.g., presence of antibiotic-resistance genes or enzymes. In contrast to blood culture, the method described herein is able to detect microbes and their antibiotic sensitivity using short growth times and requires only one short culture step.

In some embodiments, more than one types of microbial detection (e.g., bacterial and fungal detection) can be combined into the same antibiotic susceptibility testing method (e.g. bacterial detection, fungal detection, and antibiotic sensitivity) as described herein.

Antibiotic Susceptibility Assay

Figure 13:
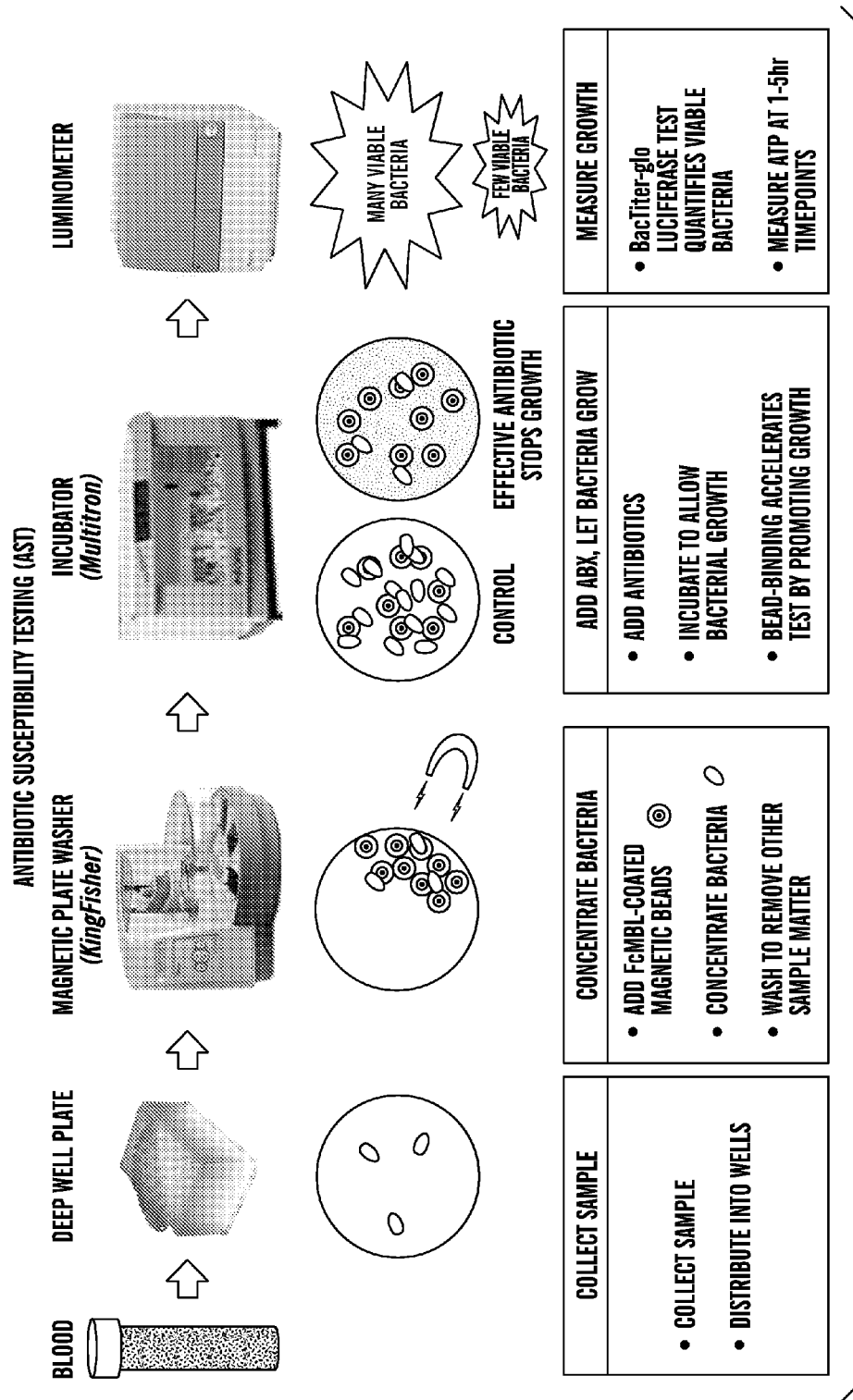
FIG. 13 is a schematic representation of an embodiment of the antibiotic susceptibility assay showing how the assay can be carried out using currently available equipment.
Figure 14B:
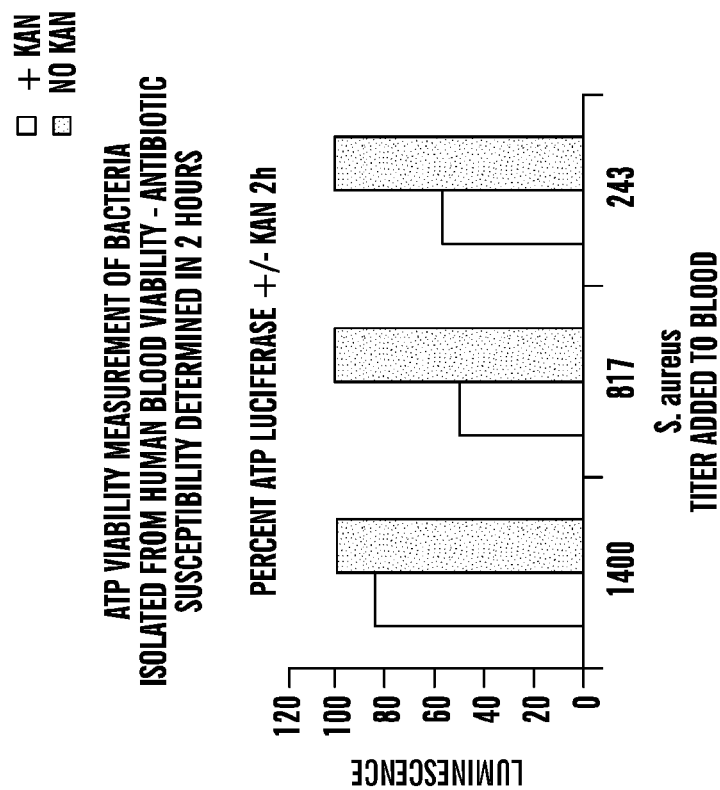
FIGS. 14A-14D are bar graphs showing ATP viability measurement of bacteria isolated from human blood.
Figure 14A:
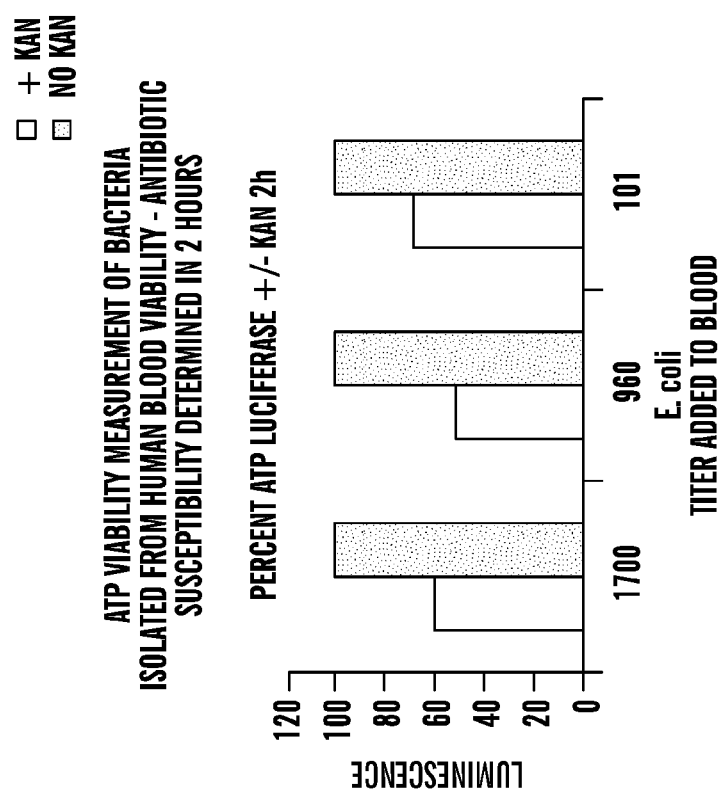
Figure 14D:
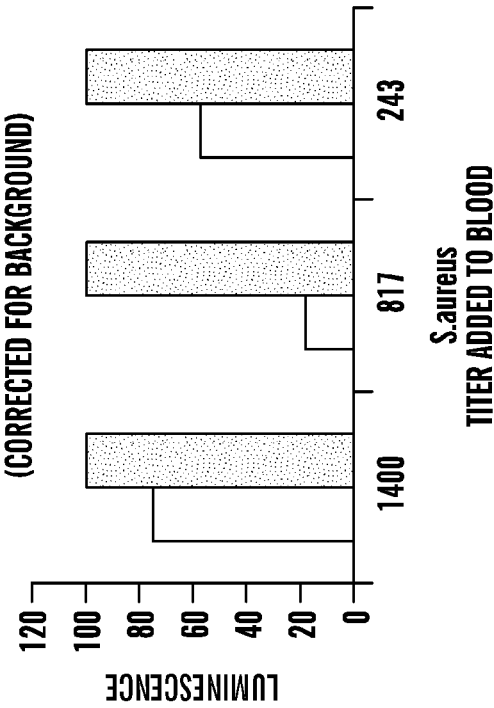
Figure 14C:
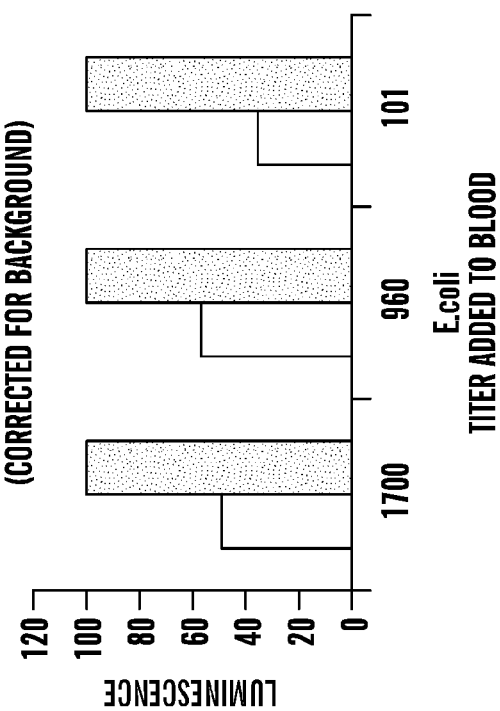

An exemplary process for determining the antibiotic susceptibility of a microbe (e.g., a pathogen) from a test sample is shown in FIG. 1. As shown in FIG. 1, the process 1200 comprises the optional step 1202 (preprocessing of the sample), step 1204 (processing of the sample), step 1206 comprising 1208 (microbe capture, e.g., pathogen capture) and 1210 (microbe separation, e.g., pathogen separation), the optional step 1212 (detection of microbe or pathogen identity and number), the optional step 1213 (microbe and/or detection agent immobilization), step 1214 (incubation with the antibiotic agent), and step 1216 (detection of microbe number and/or viability). While these are discussed as discrete processes, one or more of the preprocessing, processing, capture, microbe separation, detection, and antibiotic sensitivity can be performed in a system. In one embodiment, one or more of the preprocessing, processing, capture, microbe separation, detection, and antibiotic sensitivity can be performed in a microfluidic device. In some embodiments, one or more of the microbe capture or separation, microbe incubation, and microbe detection can be included in a microfluidic device. In some embodiments, one or more of the modules or systems performing microbe capture or separation, microbe incubation, and microbe detection can comprise a microfluidic channel. Use of a microfluidic device can automate the process and/or allow processing of multiple samples at the same time. One of skill in the art is well aware of methods in the art for collecting, handling and processing biological fluids which can be used in the practice of the present disclosure. Additionally, the microfluidic devices for the various steps can be combined into one system for carrying out the method described herein. For example, such a system can comprise two or more of the following: (i) a capture or separation system for capturing a microbe from a biological fluid; (ii) an incubation system for incubating the microbe with or without an antibiotic agent; and (iii) a detection system for detecting the microbe after incubation. Alternatively, the various steps can also be carried out using separate systems or devices. An example of this is illustrated in FIG. 13.

1202 (Sample Preprocessing):

It can be necessary or desired that a test sample, such be preprocessed prior to microbe detection as described herein, e.g., with a preprocessing reagent. Even in cases where pretreatment is not necessary, preprocess optionally can be done for mere convenience (e.g., as part of a regimen on a commercial platform). A preprocessing reagent can be any reagent appropriate for use with the methods described herein.

In some embodiments, the test sample can be a biological fluid, e.g., blood, plasma, serum, lactation products, amniotic fluids, sputum, saliva, urine, semen, cerebrospinal fluid, bronchial aspirate, perspiration, mucus, liquefied stool sample, synovial fluid, lymphatic fluid, tears, tracheal aspirate, and any mixtures thereof. For example, the sample can be a whole blood sample obtained from a subject suspected of having a microbe infection (e.g., a pathogen infection).

In some embodiments, the test sample can be a fluid or specimen obtained from an environmental source. For example, the fluid or specimen obtained from the environmental source can be obtained or derived from food products, food produce, poultry, meat, fish, beverages, dairy product, water (including wastewater), ponds, rivers, reservoirs, swimming pools, soils, food processing and/or packaging plants, agricultural places, hydrocultures (including hydroponic food farms), pharmaceutical manufacturing plants, animal colony facilities, or any combinations thereof.

In some embodiments, the test sample can be a fluid or specimen collected or derived from a cell culture.

In some embodiments, the test sample can be a fluid or specimen collected or derived from a microbe colony.

The sample preprocessing step generally comprises adding one or more reagents to the sample. This preprocessing can serve a number of different purposes, including, but not limited to, hemolyzing cells such as blood cells, dilution of sample, etc. The preprocessing reagents can be present in the sample container before sample is added to the sample container or the preprocessing reagents can be added to a sample already present in the sample container. When the sample is a biological fluid, the sample container can be a VACUTAINER®, e.g., a heparinized VACUTAINER®.

The preprocessing reagents include, but are not limited to, surfactants and detergents, salts, cell lysing reagents, anticoagulants, degradative enzymes (e.g., proteases, lipases, nucleases, lipase, collagenase, cellulases, amylases and the like), and solvents, such as buffer solutions.

In some embodiments, a preprocessing reagent is a surfactant or a detergent. In one embodiment, the preprocessing reagent is Triton X100.

Amount of preprocessing reagent to be added can depend on a number of factors. Generally, the preprocessing reagent is added to a final concentration of about 0.1 mM to about 10 mM. If a liquid, the preprocessing reagent can be added so as to dilute the sample at least 10%, at least 20%, at least 30%, at least 40%, at least 50%, at least 60%, at least 60%, at least 80%, at least 90%, at least 1-fold, at least 2-fold, at least 3-fold, or at least 5-fold.

After addition of the preprocessing reagent, the reagent can be mixed into the sample. This can be simply accomplished by agitating the sample, e.g., shaking the sample and/or moving the sample around in a microfluidic device.

After addition of the preprocessing reagent, the sample mixture can be incubated for a period of time, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample is incubated for about fifteen minutes at room temperature. In some embodiments, incubation is for about 5 seconds to about 60 seconds. In some embodiments, there is no incubation and the sample mixture is used directly in the sample processing step.

1204 (Sample Processing):

After the optional preprocessing step, the sample can be optionally further processed by adding one or more processing reagents to the sample. These processing reagents can degrade unwanted molecules present in the sample and/or dilute the sample for further processing. These processing reagents include, but are not limited to, surfactants and detergents, salts, cell lysing reagents, anticoagulants, degradative enzymes (e.g., proteases, lipases, nucleases, lipase, collagenase, cellulases, amylases, heparanases, and the like), and solvents, such as buffer solutions. Amount of the processing reagent to be added can depend on the particular sample to be analyzed, the time required for the sample analysis, identity of the microbe to be detected or the amount of microbe present in the sample to be analyzed.

It is not necessary, but if one or more reagents are to be added they can present in a mixture (e.g., in a solution, "processing buffer") in the appropriate concentrations. Amount of the various components of the processing buffer can vary depending upon the sample, microbe to be detected, concentration of the microbe in the sample, or time limitation for analysis.

Generally, addition of the processing buffer can increase the volume of the sample by 5%, 10%, 15%, 20% or more. In some embodiments, about 50 µl to about 500 µl of the processing buffer are added for each ml of the sample. In some embodiments, about 100 µl to about 250 µl of the processing buffer are added for each ml of the sample. In one embodiment, about 125 µl of the processing buffer are added for each ml of the sample.

In some embodiments, a detergent or surfactant comprises about 5% to about 20% of the processing buffer volume. In some embodiment, a detergent or surfactant comprises about 5% to about 15% of the processing buffer volume. In one embodiment, a detergent or surfactant comprises about 10% of the processing buffer volume.

Exemplary surfactants and detergents include, but are not limited to, sulfates, such as, ammonium lauryl sulfate, sodium dodecyl sulfate (SDS), and sodium lauryl ether sulfate (SLES) sodium myreth sulfate; sulfonates, such as, dioctyl sodium sulfosuccinate (Docusates), perfluorooctanesulfonate (PFOS), perfluorobutanesulfonate, alkyl benzene sulfonates, and 3-[(3-Cholamidopropyl)dimethylammonio]-1-propanesulfonate (CHAPS); 3-[(3-cholamidopropyl)dimethylammonio]-2-hydroxy-1-propanesulfonate (CHAPSO); phosphates, such as alkyl aryl ether phosphate and alkyl ether phosphate; carboxylates, such as fatty acid salts, sodium stearate, sodium lauroyl sarcosinate, perfluorononanoate, and perfluorooctanoate (PFOA or PFO); octenidine dihydrochloride; alkyltrimethylammonium salts, such as cetyl trimethylammonium bromide (CTAB) and cetyl trimethylammonium chloride (CTAC); cetylpyridinium chloride (CPC); polyethoxylated tallow amine (POEA); benzalkonium chloride (BAC); benzethonium chloride (BZT); 5-Bromo-5-nitro-1,3-dioxane; dimethyldioctadecylammonium chloride; dioctadecyldimethylammonium bromide (DODAB); sultaines, such as cocamidopropyl hydroxysultaine; cetyl alcohol; stearyl alcohol; cetostearyl alcohol (consisting predominantly of cetyl and stearyl alcohols); oleyl alcohol; polyoxyethylene glycol alkyl ethers (Brij) such as, octaethylene glycol monododecyl ether and pentaethylene glycol monododecyl ether; polyoxypropylene glycol alkyl ethers; glucoside alkyl ethers, such as decyl glucoside, lauryl glucoside and octyl glucoside; polyoxyethylene glycol octylphenol ethers, such as Triton X-100; polyoxyethylene glycol alkylphenol ethers, such as Nonoxynol-9; glycerol alkyl esters, such as glyceryl laurate; polyoxyethylene glycol sorbitan alkyl esters, such as Polysorbate 20 (Polyoxyethylene (20) sorbitan monolaurate), Polysorbate 40 (Polyoxyethylene (20) sorbitan monopalmitate), Polysorbate 60 (Polyoxyethylene (20) sorbitan monostearate), and Polysorbate 80 (Polyoxyethylene (20) sorbitan monooleate); cocamide ME; cocamide DEA; dodecyldimethylamine oxide; poloxamers; DOC; nonyl phenoxypolyethoxylethanol NP-40 (Tergitol-type NP-40); octyl phenoxypolyethoxylethanol (Noidet P-40); cetyltrimethylammonium bromide; and any mixtures thereof.

In some embodiments, one ml of the processing buffer comprises about 1 U to about 100 U of a degradative enzyme. In some embodiments, one ml of the processing buffer comprises about 5 U to about 50 U of a degradative enzyme. In one embodiment, one ml of the processing buffer comprises about 10 U of a degradative enzyme. Enzyme unit (U) is an art known term for the amount of a particular enzyme that catalyzes the conversion of 1 μmol of substrate per minute.

In some embodiments, one ml of the processing buffer comprises about 1 μg to about 10 μg of an anti-coagulant. In some embodiment, one ml of the processing buffer comprises about 1 μg to about 5 μg of an anti-coagulant. In one embodiment, one ml of the processing buffer comprises about 4.6 μg of an anti-coagulant.

In some embodiments, one ml of the processing buffer comprises about 1 mg to about 10 mg of anti-coagulant. In some embodiment, one ml of the processing buffer comprises about 1 mg to about 5 mg of anti-coagulant. In one embodiment, one ml of the processing buffer comprises about 4.6 mg of anti-coagulant.

Exemplary anti-coagulants include, but are not limited to, heparin, heparin substitutes, salicylic acid, D-phenylalanyl-L-prolyl-L-arginine chloromethyl ketone (PPACK), Hirudin, ANCROD® (snake venom, VIPRONAX®), tissue plasminogen activator (tPA), urokinase, streptokinase, plasmin, prothrombopenic anticoagulants, platelet phosphodiesterase inhibitors, dextrans, thrombin antagonists/inhibitors, ethylene diamine tetraacetic acid (EDTA), acid citrate dextrose (ACD), sodium citrate, citrate phosphate dextrose (CPD), sodium fluoride, sodium oxalate, sodium polyanethol sulfonate (SPS), potassium oxalate, lithium oxalate, sodium iodoacetate, lithium iodoacetate and mixtures thereof.

Suitable heparinic anticoagulants include heparins or active fragments and fractions thereof from natural, synthetic, or biosynthetic sources. Examples of heparin and heparin substitutes include, but are not limited to, heparin calcium, such as calciparin; heparin low-molecular weight, such as enoxaparin (LOVENOX®), Bemiparin, Certoparin, Dalteparin, Nadroparin, Parnaparin, Reviparin or Tinzaparin; heparin sodium, such as heparin, lipo-hepin, liquaemin sodium, and panheprin; heparin sodium dihydroergotamine mesylate; lithium heparin; and ammonium heparin.

Suitable prothrombopenic anticoagulants include, but are not limited to, anisindione, dicumarol, warfarin sodium, and the like.

Examples of phosphodiesterase inhibitors suitable for use in the methods described herein include, but are not limited to, anagrelide, dipyridamole, pentoxifyllin, and theophylline.

Suitable dextrans include, but are not limited to, dextran70, such as HYSKON™ (CooperSurgical, Inc., Shelton, Conn., U.S.A.) and MACRODEX™ (Pharmalink, Inc., Upplands Vasby, Sweden), and dextran 75, such as GENTRAN™ 75 (Baxter Healthcare Corporation).

Suitable thrombin antagonists include, but are not limited to, hirudin, bivalirudin, lepirudin, desirudin, argatroban, melagatran, ximelagatran and dabigatran.

As used herein, anticoagulants can also include factor Xa inhibitors, factor IIa inhibitors, and mixtures thereof. Various direct factor Xa inhibitors are known in the art including, those described in Hirsh and Weitz, Lancet, 93:203-241, (1999); Nagahara et al. Drugs of the Future, 20: 564-566, (1995); Pinto et al, 44: 566-578, (2001); Pruitt et al, Biorg. Med. Chem. Lett., 10: 685-689, (2000); Quan et al, J. Med. Chem. 42: 2752-2759, (1999); Sato et al, Eur. J. Pharmacol, 347: 231-236, (1998); Wong et al, J. Pharmacol. Exp. Therapy, 292:351-357, (2000). Exemplary factor Xa inhibitors include, but are not limited to, DX-9065a, RPR-120844, BX-807834 and SEL series Xa inhibitors. DX-9065a is a synthetic, non-peptide, propanoic acid derivative, 571 D selective factor Xa inhibitor. It directly inhibits factor Xa in a competitive manner with an inhibition constant in the nanomolar range. See for example, Herbert et al, J. Pharmacol. Exp. Ther. 276:1030-1038 (1996) and Nagahara et al, Eur. J. Med. Chem. 30 (suppl):140s-143s (1995). As a non-peptide, synthetic factor Xa inhibitor, RPR-120844 (Rhone-Poulenc Rorer), is one of a series of novel inhibitors which incorporate 3-(S)-amino-2-pyrrolidinone as a central template. The SEL series of novel factor Xa inhibitors (SEL1915, SEL-2219, SEL-2489, SEL-2711: Selectide) are pentapeptides based on L-amino acids produced by combinatorial chemistry. They are highly selective for factor Xa and potency in the pM range.

Factor IIa inhibitors include DUP714, hirulog, hirudin, melgatran and combinations thereof. Melagatran, the active form of pro-drug ximelagatran as described in Hirsh and Weitz, Lancet, 93:203-241, (1999) and Fareed et al. Current Opinion in Cardiovascular, pulmonary and renal investigational drugs, 1:40-55, (1999).

Generally, salt concentration of the processing buffer can range from about 10 mM to about 100 mM. In some embodiments, the processing buffer comprises a salt at a concentration of about 25 mM to about 75 mM. In some embodiment, the processing buffer comprises a salt at a concentration of about 45 mM to about 55 mM. In one embodiment, the processing buffer comprises a salt at a concentration of about 43 mM to about 45 mM.

The processing buffer can be made in any suitable buffer solution known the skilled artisan. Such buffer solutions include, but are not limited to, TBS, PBS, BIS-TRIS, BIS-TRIS Propane, HEPES, HEPES Sodium Salt, MES, MES Sodium Salt, MOPS, MOPS Sodium Salt, Sodium Chloride, Ammonium acetate solution, Ammonium formate solution, Ammonium phosphate monobasic solution, Ammonium tartrate dibasic solution, BICINE buffer Solution, Bicarbonate buffer solution, Citrate Concentrated Solution, Formic acid solution, Imidazole buffer Solution, MES solution, Magnesium acetate solution, Magnesium formate solution, Potassium acetate solution, Potassium acetate solution, Potassium acetate solution, Potassium citrate tribasic solution, Potassium formate solution, Potassium phosphate dibasic solution, Potassium phosphate dibasic solution, Potassium sodium tartrate solution, Propionic acid solution, STE buffer solution, STET buffer solution, Sodium acetate solution, Sodium formate solution, Sodium phosphate dibasic solution, Sodium phosphate monobasic solution, Sodium tartrate dibasic solution, TNT buffer solution, TRIS Glycine buffer solution, TRIS acetate-EDTA buffer solution, Triethylammonium phosphate solution, Trimethylammonium acetate solution, Trimethylammonium phosphate solution, Tris-EDTA buffer solution, TRIZMA® Base, and TRIZMA® HCL. Alternatively, the processing buffer can be made in water.

In some embodiments, the processing buffer comprises a mixture of Triton-X, DNAse I, human plasmin, $CaCl_2$ and Tween-20. In one embodiment, the processing buffer consists of a mixture of Triton-X, DNAse I, human plasmin, $CaCl_2$ and Tween-20 in a TBS buffer.

In one embodiment, one ml of the processing buffer comprises 100 µl of Triton-X100, 10 µl of DNAse (1 U/1 µl), 10 µl of human plasmin @ 4.6 mg/ml and 870 µl of a mixture of TBS, 0.1% Tween-20 and 50 mM $CaCl_2$.

Reagents and treatments for processing blood before assaying are also well known in the art, e.g., as used for assays on Abbott TDx, AxSYM®, and ARCHITECT® analyzers (Abbott Laboratories), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay Comparison with TDx Monoclonal Whole Blood and EMIT Cyclosporine Assays, Clin. Chem. 45: 432-435 (1999)), and/or as commercially available. Additionally, pretreatment can be done as described in U.S. Pat. No. 5,135,875, European Pat. Pub. No. 0 471 293, U.S. Provisional Pat. App. 60/878,017, filed Dec. 29, 2006, and U.S. Pat. App. Pub. No. 2008/0020401, content of all of which is incorporated herein by reference. It is to be understood that one or more of these known reagents and/or treatments can be used in addition to or alternatively to the sample treatment described herein.

In some embodiments, after addition of the processing buffer, the sample comprises 1% Triton-X, 10 U of DNase, 4.6 mg/ml of plasmin, 5 mM Calcium, 0.01% of Tween 20, 2.5 mM of Tris, 150 mM of NaCl and 0.2 mM of KCl in addition to the components already present in the sample.

After addition of the processing buffer, the sample can undergo mixing. This can be simply accomplished by agitating the sample, e.g., shaking the sample or moving the sample around in a microfluidic device.

After addition of the processing reagents, the sample can be incubated for a period of time, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample is incubated for about fifteen minutes at room temperature.

1206 (1208 (Microbe Capture) and 1210 (Microbe Separation)):

After processing of the sample, the sample can be subjected to a microbe capture process. The microbe capture process can allow for concentrating and/or cleaning up the sample before proceeding with incubation with an antibiotic agent. Without limitations, any method known in the art for capturing or extracting or concentrating microbes from a biological sample (e.g., a biological fluid) can be used. A sample comprising the extracted microbes from the biological fluid is also referred to as a microbe sample herein.

The extraction and concentration process can be completed in less than 6 hours, less than 5 hours, less than 4 hours, less than 3 hours, less than 2 hours, less than 1 hour, less than 30 minutes, less than 15 minutes, less than 10 minutes, or shorter. In some embodiments, extraction and concentration of a microbe in the sample can be done within 10 minutes to 60 minutes of starting the process. In some embodiments, extraction and concentration of a microbe in the sample can be done in about 10 minutes, e.g., mixing a sample comprising a microbe to be extracted with at least one microbe-targeting substrate (e.g., a plurality of microbe-targeting magnetic particles described herein) followed by separation of the microbe-bound microbe-targeting substrate from the rest of the sample.

Additionally, the extraction and concentration process described herein can be utilized to extract a microbe in a sample of any given volume. In some embodiments, sample volume is about 0.25 ml to about 50 ml, about 0.5 ml to about 25 ml, about 1 ml to about 15 ml, about 2 ml to about 10 ml. In some embodiments, sample volume is about 5 ml. In one embodiment, sample volume is 8 ml.

Generally, microbe capturing and isolating or separating microbes from the test sample comprises contacting the test sample (e.g., the biological fluid) with a microbe-targeting molecule linked to a solid substrate or scaffold (e.g., beads, fibers, filters, beads, filters, fibers, screens, mesh, tubes, hollow fibers, fluidic channels, microfluidic channels, and the like) for capturing and isolating or separating microbes from the biological fluid.

The microbe capture process comprises mixing a solid substrate, surface of which is coated with microbe-binding molecules which can bind to a microbe in the sample. By "coated" is meant that a layer of microbe-binding molecules is present on a surface of the solid substrate and available for binding with a microbe. A solid substrate coated with microbe-binding molecules is also referred to as a "coated-substrate" or a "microbe-targeting substrate." The amount of the microbe-targeting molecules used to coat a substrate surface can vary with a number of factors such as a substrate surface area, coating density, types of microbe-targeting molecules, and binding performance. A skilled artisan can determine the optimum density of microbe-targeting molecules on a substrate surface using any methods known in the art. By way of example only, the amount of the microbe-targeting molecules used to coat a substrate can vary from about 1 wt % to about 30 wt % or from about 5 wt % to about 20 wt %. In some embodiments, the amount of the microbe-targeting molecules used to coat the solid substrate can be higher or lower, depending on a specific need. However, it should be noted that if the amount of the microbe-targeting molecules used to coat the substrate is too low, the microbe-targeting substrate can show a lower binding performance with a microbe. On the contrary, if the amount of the microbe-targeting molecules used to coat the substrate is too high, the dense layer of the microbe-targeting molecules can exert an adverse influence on the binding properties.

In some embodiments, the coated-substrate is a particle, e.g., a nano- or micro-particle. In some embodiments, the microbe-binding molecule coated substrate is a MBL, a recombinant MBL, FcMBL or AKT-FcMBL coated bead, microbead or magnetic microbead as described in the International Application Publication Nos. WO/2011/090954 and WO/2013/012924, contents of both of which are incorporated herein by reference. In some embodiments, the microbe-targeting substrate can be coated with antibodies, aptamers, or nucleic acids against specific microbes, lectin (e.g., but not limited to MBL), or any combinations thereof.

The amount of coated-substrate added to the sample can be dependent on a number of different factors, such as, number of affinity molecules on the substrate, size of the substrate, binding affinity of the affinity molecule to the microbe, and concentration of the microbe in the sample. Additionally, the amount of coated-substrate added to the sample can be adjusted to optimize the capture of microbes. In some embodiments, the amount of coated-substrate added to the sample is such that a substrate binds with one microbe. However, each microbe can be bound to more than one coated-substrate. This can induce cross-linking of multiple microbes together which can lead to coagulation or precipitation of such cross-linked microbes from the sample. When the coated-substrate is a bead, about 100 to about $10^9$ beads can be added to each ml of the sample. In some embodiments, about $10^4$ to about $5 \times 10^6$ beads can be added for each ml of sample.

In some embodiments, the coated-substrate can be present in the processing buffer. For example, one ml of the processing buffer can comprise about 100 µl of Triton-X100, 10 µl of a solution comprising about 25 million affinity molecule coated-beads (e.g., AKT-FcMBL on 1 µm MyOne C1 streptavidin beads), 10 µl of DNase (1 U/1 µl), 10 µl of human plasmin at 4.6 mg/ml and 870 µl of a mixture of TBS, 0.1% Tween-20, and about 50 mM $CaCl_2$.

In some embodiments, the coated-substrate and microbe to be extracted can be present in a processing buffering. For example, 10 µL of a sample (e.g., diluted sample) comprising a microbe can be added to about 1 mL of processing buffer comprising a mixture of TBS, 0.1% Tween-20, 5 mM $Ca^{2+}$ and 10 µL of microbe-targeting substrates (e.g., Akt-FcMBL magnetic particles) at a concentration of about 1 mg/mL to about 2 mg/mL.

After addition of the coated-substrate, the coated-substrate can be mixed in the sample to allow microbes to bind with the affinity molecule. This can be simply accomplished by agitating the sample, e.g., shaking the sample and/or moving the sample around in a microfluidic device.

After addition of the coated-substrate, the sample mixture can be incubated for a period of time to allow the coated-substrate to bind with the microbes, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample can be incubated for about fifteen minutes at room temperature. In some embodiments, the sample can be incubated with agitation (e.g., mechanical mixing) for about 10-15 minutes at room temperature.

To prevent or reduce agglutination during separation of the microbes from the sample, additional reagents can be added to the sample mixture. Such reagents are also referred to as blocking reagents herein. For example, these blocking reagents can comprise a ligand of the target-binding molecules on the coated-substrate. Addition of such blocking reagents can reduce agglutination by binding with any empty ligand binding sites on the target-binding molecules. Accordingly, when a MBL, FcMBL, or Akt-FcMBL coated-substrate is used for capturing the microbes the blocking reagent can be a carbohydrate, such as mannose. The amount of blocking reagent can depend on the amount of coated substrate added to the sample. Generally, the blocking reagent can be added to a final concentration of about 0.1 mM to about 10 mM. In some embodiments, the blocking reagent is added at a final concentration of about 10 mM.

After addition of the blocking reagent, the sample mixture can be incubated for a period of time to allow the blocking reagent to bind with the target-binding molecules, e.g., for at least one minute, at least two minutes, at least three minutes, at least four minutes, at least five minutes, at least ten minutes, at least fifteen minutes, at least thirty minutes, at least forty-five minutes, or at least one hour. Such incubation can be at any appropriate temperature, e.g., room-temperature (e.g., about 16° C. to about 30° C.), a cold temperature (e.g. about 0° C. to about 16° C.), or an elevated temperature (e.g., about 30° C. to about 95° C.). In some embodiments, the sample is incubated for about fifteen minutes at room temperature. In some embodiments, incubation is for about 5 seconds to about 60 seconds.

1210 (Microbe Separation from Sample):

The sample mixture is then subjected to a microbe separation process. Without wishing to be bound by a theory, capture and separation of the bound microbes from the sample can concentrate the microbes and also remove components which can interfere with the assay from the sample. Any method known in the art for separating the coated-substrate from the sample can be employed.

For example, when the coated-substrate is magnetic, e.g., a magnetic bead, a magnet can be employed to separate the substrate bound microbes from the sample fluid. Without limitations, microbe capture also can be carried out by non-magnetic means, for example, by coating microbe-binding molecules on non-magnetic solid substrates or scaffolds (e.g., beads, posts, fibers, filters, capillary tubes, etc.) and flow sample by these affinity substrates.

The skilled artisan is well aware of methods for carrying out magnetic separations. Generally, a magnetic field or magnetic field gradient can be applied to direct the magnetic beads. Optionally, the bound microbe can be washed with a buffer to remove any leftover sample and unbound components. The number of wash steps can range from 1 to many, e.g., 1, 2, 3, 4, 5, 6, 7, 8, 9, 10 or more wash steps. Without wishing to be bound by a theory, capture and separation of the bound microbes from the sample can concentrate the microbes and also remove components, which can interfere with the assay or process, from the test sample.

The magnetic field source can be any magnet device positioned to generate the magnetic field gradient that is used to pull the captured microbe out from the sample. An electromagnetic controller can be used to control and adjust the magnetic field and gradients thereof, and to control the migration, separation and orientation of the magnetically bound microbes. The magnetic field gradient can be generated by a permanent magnet or by an electromagnetic signal generator. The electromagnetic signal generator can include an electromagnet or electrically-polarizable element, or at least one permanent magnet. The magnetic field gradient can be produced at least in part according to a pre-programmed pattern. The magnetic field gradient can have a defined magnetic field strength and/or spatial orientation. In some embodiments, the magnetic field gradient has a defined magnetic field strength. The term "magnetic field gradient" as used herein refers to a variation in the magnetic field with respect to position. By way of example only, a one-dimensional magnetic field gradient is a variation in the magnetic field with respect to one direction, while a two-dimensional magnetic field gradient is a variation in the magnetic field with respect to two directions.

As used herein, the term "magnetic field" refers to magnetic influences which create a local magnetic flux that flows through a composition and can refer to field amplitude, squared-amplitude, or time-averaged squared-amplitude. It is to be understood that magnetic field can be a direct-current (DC) magnetic field or alternating-current (AC) magnetic field. The magnetic field strength can range from about 0.00001 Tesla per meter (T/m) to about $10^5$ T/m. In some embodiments, the magnetic field strength can range from about 0.0001 T/m to about $10^4$ T/m. In some other embodiments, the magnetic field strength can range from about 0.001 T/m to about $10^3$ T/m.

In some embodiments, microbe capture and/or microbe-targeting substrate separation can be performed by a rapid microbe diagnostic device as described in Int. Pat. App. No. WO 2011/091037, filed Jan. 19, 2011, and/or WO 2012/135834 filed Apr. 2, 2012, the contents of which are incorporated herein by reference. A rapid microbe diagnostic device as described in Int. Pat. App. No. WO 2011/091037, filed Jan. 19, 2011, can be modified to replace the capture chamber or capture and visualization chamber with an s-shaped flow path. A magnet can then be used to capture bound microbe against the flow path wall; separating the bound microbe from rest of the sample.

In some embodiments, microbe capture and/or separation (e.g., pathogen capture and/or separation) is by a device or method as described in U.S. Pat. App. Pub. No. 2009/0220932, No. 2009/007861, No. 2010/0044232, No. 2007/0184463, No. 2004/0018611, No. 2008/0056949, No. 2008/0014576, No. 2007/0031819, No. 2008/0108120, and No. 2010/0323342, the contents of which are all incorporated herein by reference.

Methods of separating or concentrating a microbe (e.g., a pathogen) from a biological sample are also described in the International Application Publication No. WO/2013/012924, contents of which are incorporated herein by reference.

Without limitations, if a microbe-targeting substrate does not possess a magnetic property, isolation of a microbe-targeting substrate (e.g., particles, posts, fibers, dipsticks, membrane, filters, capillary tubes, etc.) from the test sample can be carried out by non-magnetic means, e.g., centrifugation, and filtration. In some embodiments where the microbe-targeting substrate is in a form a dipstick or membrane, the microbe-targeting dipstick or membrane can be simply removed from the test sample, where microbes, if any, in the test sample, remained bound to the engineered microbe-binding molecules conjugated to the dipstick or membrane substrate.

The extracted sample can optionally be washed any number (e.g., 1, 2, 3, 4, 5 or more) of times before incubation with an antibiotic agent. Without wishing to be bound by a theory, such washing can reduce and or eliminate any contaminants from the biological fluid that can be problematic during incubation or detection. In one embodiment, the microbe-targeting substrate after isolated from the solution and/or the test sample can be washed with a buffer (e.g., but not limited to, TBST) for at least about 1-3 times.

Any art-recognized wash buffer that does not affect function/viability of the microbe bound on the microbe-targeting substrate and does not interfere with binding of the microbe with the microbe-targeting substrate can be used to wash the extracted or isolated microbe-bound microbe-targeting substrates (e.g., but not limited to microbe-bound microbe-targeting magnetic particles). Examples of a wash buffer can include, but are not limited to, phosphate-buffered saline, Tris-buffered saline (TBS), and a combination thereof. In some embodiments, the same processing buffer described herein without microbe-targeting substrates (e.g., microbe-targeting magnetic particles) and microbes can be used as the wash buffer. For example, in some embodiments, a wash buffer can include a mixture of TBS, 0.1% Tween and 5 mM $Ca^{2+}$.

The amount of calcium ions ($Ca^{2+}$) present in the processing buffer and/or wash buffer can vary from about 1 mM to about 100 mM, from about 3 mM to about 50 mM, or from about 5 mM to about 25 mM. Calcium ions can be obtained from any calcium salts, e.g., but not limited to, $CaCl_2$, $CaBr_2$, $CaI_2$, and $Ca(NO_3)_2$, and any other art-recognized calcium salts. Without wishing to be bound by theory, the presence of calcium ions in the processing buffer and/or wash buffer can facilitate and/or maintain calcium-dependent binding (e.g., lectin-mediated binding such as MBL-mediated binding) of the microbe to a microbe-targeting substrate.

In some embodiments, the processing buffer and/or wash buffer can exclude calcium ions and/or include a chelator, e.g., but not limited to, EDTA. In such embodiments, microbes that solely depend on calcium-dependent binding (e.g., lectin-mediated binding such as MBL-mediated binding) to the microbe-targeting substrate will less likely bind to the microbe-targeting substrate in the absence of calcium ions. However, microbes (e.g., pathogens such as S. aureus) that at least partly depend on non-calcium-dependent interaction (e.g., but not limited to, protein A/Fc-mediated binding) with the microbe-targeting substrate (e.g., FcMBL-coated magnetic particles) can bind to the microbe-targeting substrate in the absence of calcium ions, and additional information can be found, e.g., in the International Application Publication No. WO/2013/012924, or in the U.S. Provisional App. No. 61/605,052 filed Feb. 29, 2012, the content of which is incorporated herein by reference.

In some embodiments, the capture or extraction from the biological fluid or other test samples can be accomplished by a method that does not require the identity of the microbe to be known for capture or extraction. This can be accomplished using a substrate coated with a broad-spectrum microbe-binding molecule for microbe extraction from the test sample. For example, in their previous work, the inventors described a method for the extraction and concentration of microbes (e.g., pathogens) from blood that does not require prior identification of pathogen. See PCT Application No. PCT/US2011/021603, filed Jan. 19, 2011, content of which is incorporated herein by reference. The method is based on beads that are coated with mannose binding lectin (MBL) or a genetically engineered version of MBL (FcMBL or Akt-FcMBL). MBL is a key component of the innate immune system, which binds to carbohydrate structures containing mannose, N-acetyl glucosamine and fucose on the surface of microbes or pathogens and that are not found on mammalian cells. MBL binds to at least 36 species of bacteria (e.g. Gram positive: Staphylococci, MRSA, VRSA, Streptococci, Clostridium; Gram negative: Pseudomonas, E. coli, Klebsiella,), 17 viruses (e.g. CMV, HIV, Ebola, HSV, HepB), 20 fungi (e.g., Candida, Aspergillus, Cryptococcus), and 9 parasites (e.g. Malaria, Schistosoma), in addition to at least one molecular toxin (e.g., LPS endotoxin). Consequently, MBL can serve as a broad-spectrum capture reagent, allowing a wide range of microbes (e.g., pathogens) to be extracted and concentrated from blood samples or other biological fluids.

Accordingly, in some embodiments of the aspects described herein, microbe capture or extraction from a biological sample or other test sample is by substrate coated with a broad-spectrum microbe-targeting molecule. For example, microbe capture or extraction from a biological sample is by magnetic micro- or nano-beads as described in the International Application Publication Nos. WO/2011/090954 and WO/2013/012924, contents of both of which are incorporated herein by reference.

The inventors have discovered inter alia that adding a solid substrate coated with an anticoagulant to the extracted microbe sample can allow for better sample division, analysis or reproducibility. Without wishing to be bound by theory, addition of additional anticoagulant can reduce clumping of microbe-targeting substrates. Accordingly, in some embodiments, anticoagulant coated substrate can be added to the test sample before or during or after the capture step. Without limitations, anticoagulant can be coated on a microbe-targeting substrate (i.e. a substrate coated with a microbe-targeting molecule). Generally, coating the substrate with an anticoagulant before coating with microbe-targeting molecule provides substantially same efficiency as for a microbe-targeting substrate that has not been coated with an anticoagulant. Alternatively, or in addition, a substrate coated only with anticoagulant can be added.

Any amount of anticoagulant coated substrate can be added to the test sample. For example, amount of anticoagulant coated substrate can be from about 5 wt % to about 500 wt % of the microbe-binding molecule coated substrate to be used for microbe extraction.

In some embodiments, about equal amounts of anticoagulant coated and microbe-binding molecule coated substrate can be added to the test sample.

1212 (Optional Microbe Detection):

Before incubation with an antibiotic agent, one can optionally analyze, detect, determine identity, or confirm the presence of a microbe in the sample. In accordance with various embodiments described herein, the identity of a microbe is not required before incubation with an antibiotic agent. However, in some embodiments, it can be desirable to detect or determine the presence and/or initial number of microbes bound on a microbe-targeting substrate, prior to incubation with an antibiotic agent, e.g., for evaluation of efficacy of an antibiotic agent to treat the microbe.

In some embodiments, the microbes captured can be cultured to ascertain the vitality of the microbe prior to determination of antibiotic susceptibility. The cultivation step can also be used to increase the number of microbes available for antibiotic susceptibility testing and subsequent determination of the bacterial or microbial identity. The microbes captured can be cultured for any period of time. In some embodiments, the microbes captured can be cultured for at least about 30 seconds, at least about 1 minute, at least about 5 minutes, at least about 10 minutes, at least about 15 minutes, at least about 30 minutes, at least about 1 hour, at least about 2 hours, or longer. In some embodiments, the microbes captured can be cultured for at least about 1 hour, at least about 2 hours, at least about 3 hours, at least about 4 hours, at least about 5 hours, at least about 6 hours, at least about 12 hours or longer. In some embodiments, the microbes captured can be cultured for at least about 12 hours, at least about 24 hours, at least about 36 hours, at least about 48 hours, at least about 72 hours or longer. Generally, the longer the microbes are cultured, the larger population of the microbes captured can become. In other embodiments, a small number of microbes can be sufficient for an antibiotic susceptibility assay described herein, and thus no culture for cell expansion is required.

Accordingly, in some embodiments, the extracted or concentrated microbes (e.g., microbes bound on a microbe-targeting substrate) can be labeled with a labeling molecule (as described in detail hereafter) that allows detection of microbe presence, but does not compromise microbe viability or function (e.g., bacterial metabolism). An exemplary labeling molecule can be fluorescently labeled, luminescently labeled or isotopically labeled. The labeling molecule can be specific or non-specific to types or species of microbes. In some embodiments, fluorescent nano- or micro-particles coated with microbe-targeting molecules described herein (e.g., FcMBL) can be used to label extracted or concentrated microbes. After labeling, the labeled microbes can be washed (e.g., once, twice, three times, four time, five times or more) with a wash buffer described earlier to remove any unbound detection labels. In one embodiment, Akt-FcMBL coated FluoSpheres, (Life Technologies, Carlsbad, Calif.), e.g., having a size of about 40 nm can be used to label extracted or concentrated microbes.

Depending on types of microbe labeling methods, for example, a detection component, device or system can be used to optionally detect the presence of the separated microbe by spectroscopy, electrochemical detection, polynucleotide detection, fluorescence anisotropy, fluorescence resonance energy transfer, electron transfer, enzyme assay, magnetism, electrical conductivity, isoelectric focusing, chromatography, immunoprecipitation, immunoseparation, aptamer binding, filtration, electrophoresis, use of a CCD camera, immunoassay, polymerase chain reaction (PCR), mass spectroscopy, microcalorimetry, mass spectrometry, or substantially any combination thereof. Without limitations, microbe analysis or detection can be carried out using any methods known in the art for determining cell viability, growth or functional response including those described herein. Without wishing to be bound by a theory, identifying the microbe before incubating with antibiotic agents can reduce the number of antibiotic agents that need to be tested. For example, susceptibility can be tested against only those antibiotic agents that are known to be effective against the specific class of microbe, type of microbe or specific microbe identified.

In some embodiments, the captured microbe (e.g., pathogen) can be analyzed or detected in the capture chamber or capture and visualization chamber of a rapid pathogen diagnostic device described in the Int. Pat. App. No. WO/2011/091037, filed Jan. 19, 2011. Alternatively, the captured microbe can be recovered (i.e., removed) and analyzed and/or detected.

In some embodiments, the captured microbe (e.g., pathogen) is recovered and analyzed or detected using a particle on membrane assay as described in U.S. Pat. No. 7,781,226, content of which is incorporated herein by reference. A particle on membrane assay as described in U.S. Pat. No. 7,781,226 can be operably linked with a rapid pathogen diagnostic device of the Int. Pat. App. No. WO/2011/091037 to reduce the number of sample handling steps, automate the process and/or integrate the capture, separation and analysis/detection steps into a microfluidic device.

In some embodiments, microbe capture, separation and analysis can be done using a hybrid microfluidic SPR and molecular imagining device as described in U.S. Pat. App. Pub. No. US 2011/0039280.

In some embodiments, while not necessary, microbe detection 1212 can include determination of an identity of a microbe captured and isolated from step 1206. Methods to identify a microbe are known in the art. For example, a portion of the isolated microbe (without treatment with any antibiotic agent) can be subjected to mass spectroscopy (e.g., matrix-assisted laser desorption/ionization (MALDI)-time of flight (TOF) mass spectroscopy). Alternatively or additionally, a portion of the isolated microbe can be subjected to a molecular assay to determine/detect specific identification markers (e.g., but not limited to, PCR, including in situ PCR, immunoassay, and/or immunostaining).

In accordance with various aspects described herein, microbes in a sample needs not be identified prior to incubation with one or more antibiotic agents. While FIG. 1 illustrates that the optional step 1212 (microbe detection) can occur between step 1206 and optional step 1213, it should be readily appreciated that the optional step 1212 can be carried out at any time after step 1206 (microbe capture and separation). In some embodiments, step 1212 can be performed independently in parallel with any of the steps after step 1206. In some embodiments, step 1212 can be performed after step 1216 where antibiotic activity is detected in microbial cultures. For example, the captured microbes grown in the control antimicrobial/antibiotic-free matrix can be subjected to microbe identification (e.g., MALDI-TOF mass spectroscopy). In some embodiments, step 1212 can be performed once or more than once throughout the process 1200.

1213 (Optional Microbe and/or Detection Agent Immobilization):

Once the microbes or pathogens bound to the microbe-targeting substrate are isolated or extracted from a biological fluid, the isolated microbes from the biological fluid can be separated into a plurality of subsamples (e.g., 1, 2, 3, 4, 5, 6, 7, 8, 9, 10, 15, 20, 30, 40, 50, 100, 150, or more) before incubation with different concentrations of antibiotic agents to be tested. The number of subsamples depends, among other factors, on the number of antibiotic agents and control combinations to be tested or the amount of microbes isolated. Generally, each subsample can comprise a substantially equal number of microbes. Determination of equal number of microbes in each subsample can be determined indirectly by dividing the subsamples so as to generate duplicates for each treatment (including control) and confirming the same readouts for the duplicates at assay termination.

In some embodiments, antibiotic susceptibility can be determined based on a collective response from a population of captured or isolated microbes, e.g., microbes bound on one or more microbe-targeting substrates, e.g., microbe-targeting magnetic particles. In some embodiments, antibiotic susceptibility can be determined based on a collective response from more than 1, more than 10, more than 25, more than 50, more than 100, more than 1000, more than $10^5$ captured or isolated microbes, e.g., microbes bound on one or more microbe-targeting substrates, e.g., microbe-targeting magnetic particles. In these embodiments, a population of microbes in a subsample can be subjected to incubation with at least one antibiotic agent (step 1214) without microbe immobilization (step 1213) as described herein.

As used herein, the term "collective response" refers to the average response of a population of captured or isolated microbes (e.g., microbes bound on one or more microbe-targeting substrates, e.g., microbe-targeting magnetic particles). In a population some captured microbes can respond differently to an antibiotic agent from some other captured microbes in the same population. For example, while a small number of captured or isolated microbes may not be responsive or may be less responsive to an antibiotic agent, the collective response based on the total population could still indicate a positive therapeutic effect of an antibiotic agent on treatment of the microbes if the majority of the captured or isolated microbes are adversely affected by the antibiotic agent.

In some embodiments, antibiotic susceptibility can be determined based on individual microbes. In such embodiments, responses of individual microbes to an antibiotic can be independently monitored. In these embodiments, at least a portion of the captured microbes (e.g., microbes bound on one or more microbe-targeting substrates, e.g., one or more microbe-targeting magnetic particles) can be subjected to microbe and/or detection agent immobilization (step 1213) as described herein. For example, in one embodiment, at least a portion of the captured microbes (e.g., microbes bound on one or more microbe-targeting substrates, e.g., microbe-targeting magnetic particles) in each subsample can be immobilized in a matrix and/or on a solid support. By the term "immobilized" is generally meant an object or an entity (e.g., a microbe, or a detection agent) being substantially fixed in place or being encapsulated in a confined space for at least a period of time. In reference to a microbe, the term "immobilized" refers to a microbe being substantially fixed in place, e.g., in a matrix and/or on a solid support, for at least a period of time so that the same microbe can be tracked for its response and behavior during that period of time, e.g., after the microbe is treated with at least one antibiotic agent. The term "substantially fixed in place" refers to movement of a microbe from its initial position in a matrix and/or on a solid support (e.g., before incubation with an antibiotic agent) being less than 100 µm, less than 50 µm, less than 25 µm, less than 10 µm, less than 5 µm, less than 1 µm, less than 0.5 µm, less than 0.1 µm, less than 0.01 µm or lower. In reference to a detection agent, the term "immobilized" refers to a detection agent being encapsulated in a confined space, e.g., in a matrix, or being localized at a specific location, e.g., on a solid support, for at least a period of time.

In some embodiments, at least a portion of the captured microbes in each subsample can be placed on a solid support and overlaid with a matrix, e.g., a gel matrix.

In some embodiments where the microbes are captured on microbe-targeting magnetic particles, the captured microbes can be immobilized on a solid support with an underlying magnet. However, in some embodiments where continuous exposure of the captured microbes to a magnetic field, e.g., during treatment with an antibiotic agent, is not desirable, the captured microbes can be first immobilized on a solid support with an underlying magnet, followed by an overlay with a matrix, e.g., a gel matrix, such that the captured microbes can be immobilized on a solid support by the matrix. In such embodiments, the magnet underlying the solid support to immobilize the captured microbes can be removed after the matrix, e.g., gel matrix, has gelled.

In some embodiments, rather than overlaying a captured microbe placed on a solid support with a matrix, e.g., a gel matrix, the captured microbe can be suspended and mixed in a matrix, e.g., a gel matrix, when the matrix is still a liquid or a viscous liquid. In such embodiments, a captured microbe dispersed in a liquid matrix or a viscous liquid matrix can be spotted on a solid support where the liquid matrix or viscous liquid matrix comprising the captured microbe is allowed to gel or set.

As used herein, the term "solid support" generally refers to any structural surface on which an entity can deposit (or attach to). Such structural surface can take the form of, e.g., but not limited to, plates (e.g., multi-well plates) or slides (e.g., microscopic slides), papers or strips, disks, dipsticks, tubes, discs, capillaries, cover slips, films, containers, microchannels, and beads. The structural surface can be substantially flat or curved. The solid support can be biological, nonbiological, organic, inorganic, or a combination of any of these. Exemplary solid support material can include, but are not limited to, glass, PDMS, silicone rubber, quartz, latex, polyurethane, silicon and modified silicon, Ge, gallium arsenide, GaP, silicon dioxide, silicon nitride, metals (such as gold, and other derivatizable transition metals, a variety of gels and polymers such as (poly)tetrafluoroethylene, (poly)vinylidendifluoride, polystyrene, polystyrene-divinylbenzene copolymer, polycarbonate, polypropylene, and any combinations thereof. Other suitable solid support materials will be readily apparent to those of skill in the art. Solid-support base materials are generally compatible and/or inert to a reaction condition to which they are subjected in the assays described herein.

In some embodiments, the solid support can be coated with a detection substrate prior to applying a captured microbe onto a solid support. As used herein, the term "a detection substrate" refers to a substrate immobilized with at least one detection agent for determining at least a function and/or response of a microbe. For example, depending on types of the detection agent, the detection substrate can be reactive to microbe metabolism (e.g., bacterial metabolism or bacterial activity), cell viability (e.g., live vs. dead), intracellular pH, and/or cell growth that can be analyzed by microscopy, e.g., a fluorescent microscope. In some embodiments, at least one detection agent can be encapsulated or immobilized in a matrix or a gel matrix. A gel matrix coating comprising at least one detection agent can have any thickness and/or any concentrations of matrix material. In some embodiments, the gel matrix coating comprising at least one detection agent can have a thickness of about 0.001 mm to about 5 mm, about 0.01 mm to about 2.5 mm, or about 0.1 mm to about 1 mm. In some embodiments, the gel matrix can have a concentration of the matrix ranging from about 0.5 wt % to about 10 wt %, or about 1 wt % to about 5 wt %. A skilled in the art can optimize the concentration of a gel matrix, depending on desired porosity and/or pore sizes of the resultant gel matrix (which can affect diffusion properties of a detection agent encapsulated therein), and/or mechanical property of the resultant gel matrix. In one embodiment, a gel matrix coating can comprise about 3% agarose gel with a thickness of about 0.5 mm.

In other embodiments, at least one detection agent can be immobilized on a solid support by covalently bound to a surface of the solid support on which the captured microbe is subsequently applied. In such embodiments, the solid support can be functionalized by any chemical coupling or conjugation methods known in the art such that a detection agent can be directly or indirectly (e.g., via a linker) conjugated to a surface of the solid support.

In some embodiments, the matrix or gel matrix overlaying a captured microbe can comprise at least one detection agent that can be used to determine at least a function and/or response of a captured microbe in the matrix. For example, in some embodiments, the matrix or gel matrix can comprise at least one detection agent that can be used to determine metabolism of a captured microbe in the matrix. For example, resazurin, carboxyfluorescein succidimyl ester, tetrazolium compounds (e.g., but not limited to, MTT, MTS, XTT, WST-1), or any other metabolic indicators (e.g., protease markers, or ATP detection) that can be converted or reduced to a different chemical by a microbe to induce a color change of the detection agent or a detectable signal can be included in the matrix or gel matrix. For example, in some embodiments, the reduction of a non-fluorescent detection agent (e.g., but not limited to, resazurin) to a fluorescent detection agent (e.g., resorufin) by metabolically active microbes can allow identification of growing microbes. In some embodiments, a peptide substrate (e.g., glycyl-phenylalanyl-amino fluorocoumarin; GF-AFC) can be included in the matrix or gel matrix and the peptide substrate can converted to a fluorescent compound in the presence of aminopeptidase activity present in viable cells. In other embodiments, ATP present in a viable microbe can be measured using a luciferase reaction to generate light. In such embodiments, luciferin and luciferase can be included in the matrix or gel matrix for ATP detection.

In some embodiments, the matrix or gel matrix overlaying a captured microbe can comprise at least one detection agent that can be used to determine the presence of viable cells in the matrix. Examples of such detection agents can include, but are not limited to, calcein AM, resazurin, tetrazolium compounds (e.g., but not limited to, MTT, MTS, XTT, WST-1), protease markers (e.g., GF-AFC), and ATP detection substrates (e.g., luciferin and luciferase), and any combinations thereof.

In some embodiments, the matrix or gel matrix overlaying a captured microbe can comprise at least one detection agent that can be used to determine the presence of dead cells in the matrix. For example, propidium iodine (or Trypan blue or another equivalent dye such as Sytox Green 11 and other nucleic acid stain such as Syto 9) can be included in the matrix or gel matrix and it can penetrate the membrane of a dead microbe due to its loss of the plasma membrane integrity and binds to nucleic acids of the dead microbe.

Other examples of a detection agent that can be included in the matrix (or gel matrix) or the detection substrate described herein can include, without limitations, any art-recognized or commercially-available cell viability indicators (e.g., but not limited to the ones from Invitrogen/Life Technologies), any art-recognized or commercially-available protease marker (e.g., but not limited to, GF-AFC), any art-recognized or commercially available pH indicator (e.g., but not limited to, SNARF indicators, HPTS (pyranine), BCECF, fluoresceins and carboxyfluoresceins, LysoSensor™ Green DND-189, Oregon Green dyes, LysoSensor Yellow/Bue DND-160 and pHrodo™ dye from Invitrogen/Life Technologies), any art-recognized or commercially available ATP indicator (e.g., but not limited to, luciferin and luciferase), any art-recognized or commercially available ROS indicator (e.g., but not limited to, chemically reduced and acetylated forms of 2',7'-dichlorofluorescein (DCF) and calcein or any commercially available ROS detection agents, e.g., from Invitrogen/Life Technologies), and any combinations thereof.

The matrix or gel matrix to immobilize a microbe and/or a detection agent and/or to form a detection substrate can be formed from any art-recognized material that does not interfere with biological response and/or function (e.g., metabolic activity and/or viability) of a microbe under a normal or untreated condition. In some embodiments, the matrix or gel matrix can include, without limitations, an agarose gel, a collagen gel, a matrigel, an alginate gel, a biocompatible polymer gel (e.g., but not limited to, PEG, PLGA and thermally-reversible polymer gel such as N-isopropylacrylamide), a hydrogel, gelatin, a fibrin gel, a hydragel, and any combinations thereof. In some embodiments, the matrix or gel matrix used in the assays described herein can include agarose gel (e.g., low melting point agarose gel such as NUSIEVE® agarose gel). A skilled artisan can readily select an appropriate matrix for optimal growth and/or detection method (e.g., imaging) of captured microbes.

The matrix or gel matrix for immobilization a microbe and/or a detection agent can have a concentration of the matrix ranging from about 0.1% to about 10%, from about 0.2% to about 5%, or from about 0.5% to about 3%. In one embodiment, the captured microbe on a solid support can be overlaid with a ~0.5% gel matrix (e.g., agarose gel). In another embodiment, the captured microbe on a solid support can be overlaid with a ~3% gel matrix (e.g., agarose gel).

In some embodiments, the coordinates of individual microbes on a solid support (e.g., but not limited to, a cover slip, a slide, a multi-well plate) can be determined, e.g., by microscopy or imaging, before incubation with an antibiotic agent. In such embodiments, antibiotic activity in each individual microbe can be determined and/or monitored. For example, the reduction of resazurin to resorufin (560 nm excitation/590 nm emission) by bacteria can be detected before addition of an antibiotic agent or an antimicrobial agent. The coordinates of individual bacteria can also be recorded before an addition of growth media including an antibiotic agent or an antimicrobial agent. Responses of single bacterium can be detected for switch between resorufin detection (red) to detection of Sytox Green 11 uptake (green). A red to green shift indicates antibiotic activity.

1214 (Incubation with Antibiotic Agent):

At least a portion of the captured or isolated microbes (e.g., microbes bound on one or more microbe-targeting substrates from step 1206 or from step 1213 (e.g., after immobilization of at least a portion of the captured microbes in a matrix or gel matrix) can be exposed to at least one antibiotic agent. The antibiotic agent in each subsample can be the same or different. Without limitations, the microbes in one or more subsamples can be incubated with at least one antibiotic agent, including at least two, at least three, at least four or more antibiotic agent, e.g., to determine the efficacy of a combination therapy. At least one (e.g., one, two, three, four, five, six, seven, eight, nine, ten, or more) of the subsamples can be incubated without addition of any antibiotic agents for serving as a control. Alternatively, or in addition, at least one (e.g., one, two, three, four, five, six, seven, eight, nine, ten, or more) of the subsamples can be incubated with a broad-spectrum antibiotic agent for serving as a positive control.

As used herein, the term "antibiotic agent" refers to naturally occurring, semisynthetic, or fully synthetic agents which inhibit the growth of microbes (i.e., bacteria, fungi, viruses, parasites and microbial spores) thereby preventing their development and microbial or pathogenic action. An antibiotic agent can be selected from the group consisting of small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; an extract made from biological materials such as bacteria, plants, fungi, or animal cells; animal tissues; naturally occurring or synthetic compositions; and any combinations thereof. As used herein, the term "antibiotic agent" is intended to embrace antibacterial agents or antimicrobial agents, antifungal agents, antiprotozoal agents, antiviral agents and mixtures thereof.

Exemplary antibacterial agents or antimicrobial agents include, but are not limited to, Acrosoxacin, Amifloxacin, Amikacin, Amoxycillin, Ampicillin, Aspoxicillin, Azidocillin, Azithromycin, Aztreonam, Balofloxacin, lc Benzylpenicillin, Biapenem, Brodimoprim, Cefaclor, Cefadroxil, Cefatrizine, Cefcapene, Cefdinir, Cefetamet, Ceftmetazole, Cefoxitin, Cefprozil, Cefroxadine, Ceftarolin, Ceftazidime, Ceftibuten, Ceftobiprole, Cefuroxime, Cephalexin, Cephalonium, Cephaloridine, Cephamandole, Cephazolin, Cephradine, Chlorquinaldol, Chlortetracycline, Ciclacillin, Cinoxacin, Ciprofloxacin, Clarithromycin, Clavulanic Acid, Clindamycin, Clofazimine, Cloxacillin, Colistin, Danofloxacin, Dapsone, Daptomycin, Demeclocycline, Dicloxacillin, Difloxacin, Doripenem, Doxycycline, Enoxacin, Enrofloxacin, Erythromycin, Fleroxacin, Flomoxef, Flucloxacillin, Flumequine, Fosfomycin, Gentamycin, Isoniazid, Imipenem, Kanamycin, Levofloxacin, Linezolid, Mandelic Acid, Mecillinam, Meropenem, Metronidazole, Minocycline, Moxalactam, Mupirocin, Nadifloxacin, Nalidixic Acid, Netilmycin, Netromycin, Nifuirtoinol, Nitrofurantoin, Nitroxoline, Norfloxacin, Ofloxacin, Oxytetracycline, Panipenem, Pefloxacin, Phenoxymethylpenicillin, Pipemidic Acid, Piromidic Acid, Pivampicillin, Pivmecillinam, Prulifloxacin, Rufloxacin, Sparfloxacin, Sulbactam, Sulfabenzamide, Sulfacytine, Sulfametopyrazine, Sulphacetamide, Sulphadiazine, Sulphadimidine, Sulphamethizole, Sulphamethoxazole, Sulphanilamide, Sulphasomidine, Sulphathiazole, Teicoplanin, Temafloxacin, Tetracycline, Tetroxoprim, Tigecyclin, Tinidazole, Tobramycin, Tosufloxacin, Trimethoprim, Vancomycin, and pharmaceutically acceptable salts or esters thereof.

Exemplary antifungal agents include, but are not limited to, 5-Flucytosin, Aminocandin, Amphotericin B, Anidulafungin, Bifonazole, Butoconazole, Caspofungin, Chlordantoin, Chlorphenesin, Ciclopirox Olamine, Clotrimazole, Eberconazole, Econazole, Fluconazole, Flutrimazole, Isavuconazole, Isoconazole, Itraconazole, Ketoconazole, Micafungin, Miconazole, Nifuroxime, Posaconazole, Ravuconazole, Tioconazole, Terconazole, Undecenoic Acid, and pharmaceutically acceptable salts or esters thereof.

Exemplary antiprotozoal agents include, but are not limited to, Acetarsol, Azanidazole, Chloroquine, Metronidazole, Nifuratel, Nimorazole, Omidazole, Propenidazole, Secnidazole, Sineflngin, Tenonitrozole, Temidazole, Tinidazole, and pharmaceutically acceptable salts or esters thereof.

Exemplary antiviral agents include, but are not limited to, Acyclovir, Brivudine, Cidofovir, Curcumin, Desciclovir, 1-Docosanol, Edoxudine, gQ Fameyclovir, Fiacitabine, Ibacitabine, Imiquimod, Lamivudine, Penciclovir, Valacyclovir, Valganciclovir, and pharmaceutically acceptable salts or esters thereof.

In some embodiments, the antibiotic agent can be selected from the group consisting of amoxicillin/clavulanate, amikacin, ampicillin, aztreonam, ceftrazidime, cephalothin, chloramphenicol, ciprofloxacin, clindamycin, ceftriaxone, cefotaxime, cefuroxime, erythromycin, cefepime, gentamicin, imipenem, levofloxacin, linezolid, meropenem, minocycline, nitrofurantoin, oxacillin, penicillin, piperacillin, ampicillin/sulbactam, trimethoprim/sulfamethoxazole or co-trimoxazole, tetracycline, tobramycin, vancomycin, or any combinations thereof.

Rather than individually testing every available antibiotic, prior antibiotic sensitivity tests have established a practice of testing only representatives of the different antibiotic classes. The assay disclosed herein can be used to test these class representatives. However, the assay disclosed herein is flexible and can easily be augmented to include any number of additional drugs or combinations.

In some embodiments, incubation of microbes with at least one antibiotic agent can be done without detaching the microbes (e.g., pathogens) from the captured microbe-binding molecules.

In some other embodiments, the microbes or pathogens bound to the capture molecules can be detached therefrom prior to incubation with or without an antibiotic. By way of example only, without wishing to be bound by theory, as calcium ions are involved in binding interaction of MBL with microbe surface, calcium ions can be depleted from the culture medium containing the microbes or pathogens bound to the engineered microbe-targeting molecules such that the microbes become free from the engineered microbe-targeting molecules again. For detaching the bound microbes, EDTA or other chelating agent can be added to the sample.

Alternatively or in addition, divalent cations other than $Ca^{2+}$ can be added to the sample. The free microbes can then be incubated in culture medium with or without an antibiotic. Detachment of microbes from the capture molecules can be done before or after splitting the microbe sample into subsamples. Exemplary chelators include, but are not limited to, 1,2-bis(2-Aminophenoxy)ethane-N,N,N',N'-tetraacetic acid; ethylenediaminetetraacetic acid (EDTA); ethylene glycol-bis(2-aminoethylether)-N,N,N',N'-tetraacetic acid; ethylene glycol-bis(β3-aminoethyl ether)-N,N,N',N'-tetraacetic acid; 1,2-bis(o-aminophenoxy)ethane-N,N,',N'-tetraacetic acid (BAPTA); and the like.

The set of subsamples comprising microbes with or without an antibiotic agent can be incubated under any conditions suitable for microbial growth. One of skill in the art can readily determine optimum culture conditions for microbial growth (e.g., bacterial growth), e.g., incubating them at a suitable temperature and atmosphere such as at from about 20° C. to about 45° C. in the presence or absence of adequate levels of oxygen and/or carbon dioxide. In some embodiments, incubation is at from about 25° C. to about 40° C., or from about 30° C. to about 42° C., or from about 35° C. to about 40° C. In one embodiment, incubation is at about 37° C. Furthermore, incubation can be with or without agitation. Moreover, the skilled artisan appreciates that the control and the test subsamples should be incubated under substantially identical conditions. A subsample incubated without an antibiotic agent under substantially identical conditions can be used as a control or reference sample.

A sufficient amount of growth medium (e.g. LB broth or agar plate) can be added to a subsample for incubation. In some embodiments, the growth medium can further include at least one detection agent that determines at least a biological function and/or response of a captured microbe described herein (e.g., a metabolic indicator). The growth medium can be supplemented with one or more antibiotic agents to which the microbe's sensitivity is to be determined. For a control, the growth media needs not be supplemented with an antibiotic agent or the growth media can be supplemented with a broad spectrum antibiotic agent. One of skill in the art understands that amount of growth media to be added depends on the amount/volume of the subsample, the antibiotic concentration to be tested, size of the incubation vessel, time for incubation, method of detection, or other conditions to be used for incubation.

In some embodiments, the growth medium is free of yeast extract. Without wishing to be bound by a theory, yeast extract free media allows better detection or sensitivity when using further MBL-based assays.

In some embodiments where the captured microbes are to be immobilized in a matrix or a gel matrix, e.g., as in step 1213 described herein, the growth medium (optionally including a detection agent with or without an antibiotic to be evaluated) can be incorporated or mixed into the matrix or gel matrix before depositing the matrix or gel matrix over or encapsulating the captured microbes in each subsample. In some embodiments, at least one antibiotic agent can be directly incorporated or mixed into the matrix or gel matrix before depositing the matrix or gel matrix over or encapsulating the captured microbes in each subsample.

In some embodiments, the growth medium can be added to the microbial culture or added to a matrix or gel matrix for diffusion of the nutrients (optionally including a detection agent with or without an antibiotic to be evaluated) into the matrix or gel matrix.

In some embodiments, an antibiotic concentration gradient can be formed in the matrix or gel matrix for at least a period of time, for example, by diffusion or by conjugation of the antibiotic to the matrix or gel matrix.

The microbial culture can be incubated in the presence or absence of an antibiotic for any period of time. The microbial growth can be monitored during the incubation period and the incubation period can continue until there is a sufficient difference in detection signal, e.g., microbial counts, between subsamples that are antibiotic-inhibited, and those that are not. For example, in some embodiments, incubation can be for about 15 seconds, 30 seconds, 45 seconds, 1 minute, 3 minutes, 5 minutes, 10 minutes, 15 minutes, about 30 minutes or longer. In some embodiments, incubation can be for about 10, 15, 20, 25, 30, 35, 40, 45, 50, 55, 60, 90, 120, 150, 180, 210, 240, 300, 360 minutes or more. In some embodiments, incubation time can range from a lower limit of about 10, 15, 20, 25, 30, 35, 40, 45, 50, 55, or 60 minutes to an upper limit of about 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180 minutes, or more. In one embodiment, the incubation can be from about fifteen minutes to about three hours, from about thirty minutes to five hours, or from about thirty minutes to about two hours. In one embodiment, the incubation can be more than 2 hours, e.g., at least about 2 hours, at least about 6 hours, at least about 12 hours, at least about 24 hours, at least about 2 days, at least about 3 days. Depending on the proliferation and/or growth rate of captured microbes, one of skill in the art can determine optimum incubation duration for subsequent analysis, e.g., cell viability analysis.

Conditions for incubation (including, e.g., choice of growth media) can be optimized using methods well known in the art to yield optimal bacterial growth. For example, incubation can be done in an airlift formation setup to obtain optimal bacterial growth conditions. Additionally, the inventors have discovered that for the 96 well cultures, 900 RPM significantly improves growth of bacteria.

In some embodiments, incubation is carried out in incubator shaker (3 mm shake radius) in, e.g., 96-well plates or 384-well plates, (to provide enough test sample for multiple assays) at 37° C. and 950 rpm using, but not limited to, Mueller Hinton Broth. The incubation can be performed aerobically or anaerobically.

In some embodiments, the assay described herein can further include determination of minimum inhibitory concentration (MIC) and/or minimum bactericidal concentration (MBC) of one or more antibiotic agents. For example, various concentrations of an antibiotic agent can be evaluated in a plurality of subsamples of the captured microbes. In some embodiments, a plurality of subsamples can be cultured in growth media containing different concentrations of an antibiotic agent. In some embodiments, an antibiotic agent can be incorporated or mixed into a matrix or gel matrix in different concentrations before depositing the matrix or gel matrix over or encapsulating the captured microbes in corresponding subsamples. In some embodiments, an antibiotic concentration gradient can be formed in a matrix or gel matrix or a detection substrate described herein. For example, in one embodiment, an antibiotic agent can be conjugated to, or cross-linked with, a matrix or gel matrix or a detection substrate to form an antibiotic concentration gradient. In one embodiment, an antibiotic concentration gradient can be formed in a matrix or gel or gel matrix or a detection substrate by incubation in the presence of an antibiotic agent for a period of time to allow diffusion of the antibiotic agent into the matrix or gel matrix. In these embodiments where an antibiotic gradient is formed in a matrix or gel matrix or detection substrate, microbial responses to an antibiotic agent at various concentrations can be monitored at corresponding locations in a single matrix or gel matrix or a detection substrate.

In some embodiments, micro- or nano-compartments (e.g., an array of micro-wells or nano-wells) in a microfluidic device can be coated with at least one antibiotic agent such that captured microbes can be cultured therein. In these embodiments, the micro- or nano-compartments (e.g., an array of micro-wells or nano-wells) in a microfluidic device can also be coated with microbe-targeting molecules described herein such that when a fluid sample flows through such microfluidic device (an array of nanowells potentially coated with different antibiotics), one or more microbes can be captured by the microbe-targeting molecules and cultured in a single well with the antibiotic agent for antibiotic susceptibility test.

In some embodiments, at least one antibiotic agent can be conjugated to a microbe-targeting molecule described herein. Examples of microbe-targeting molecules comprising an antibiotic agent described in the Provisional Application No. 61/691,983 filed Aug. 22, 2012 entitled "Pathogen binding methods and compositions" can be used in some embodiments of the methods described herein. In these embodiments, microbes present in a test sample can be exposed to the antibiotic agent concurrently with their capture by the conjugated microbe-targeting molecules.

1216 (Microbe Growth or Functional Response Detection):

After incubation, microbe growth or a functional response of microbes can be determined using any methods known in the art for determining cell viability, growth or functional response. Bacteria can be observed for, for example, growth in the presence of the antibiotics (to determine the resistance of the bacteria to the particular antibiotics), cell death (to determine bactericidal activity), and/or inhibition of growth (to determine bacteriostatic activity). For example, microbe growth and/or cell death can be assessed by: (i) counting the number of microbes in the subsample, as compared to a control or reference; (ii) total amount of microbes in the subsample, as compared to a control or reference; (iii) ratio of cells expressing at least one microbe marker in the subsample, as compared to a control or reference; (iv) relative metabolite levels in the subsample, as compared to a control or reference; or (v) any combinations thereof. In some embodiments, the microbe growth or a functional response of microbes can be determined or monitored in real-time, e.g., by microscopy or flow cytometry.

For use as a control or reference, a subsample can be incubated without any antibiotic agents. Alternatively, or in addition, number of microbes or functional response level in the subsample can be determined before incubation with an antibiotic agent.

In some embodiments, the mechanisms of resistance of a microbe (e.g., a pathogen) to antibiotics can be extrapolated by comparison of the antibiotic susceptibility pattern or profile of the microbe (e.g., pathogen) tested to databases of antibiotic susceptibility patterns or profiles gathered from microbes (e.g., pathogens) with known resistance mechanisms.

In some embodiments, relative microbe counts in the subsample, as compared to a control, are used in determining the number of microbes in the subsample. Any method known in the art for determining the viability of cells in a sample can be used for determining the relative number of cells in a subsample as compared to a control or reference. Generally, cell viability can be assayed using cytolysis or membrane leakage assays (such as lactate dehydrogenase assays), mitochondrial activity or caspase assays (such as Resazurin and Formazan (MTT/XTT) assays), production of reactive oxygen species (ROS) assays, functional assays, or genomic and proteomic assays. Exemplary methods include, but are not limited to, ATP test, ROS test, Calcein AM, pH sensitive dyes, Clonogenic assay, Ethidium homodimer assay, Evans blue, Fluorescein diacetate hydrolysis/Propidium iodide staining (FDA/PI staining), Flow cytometry, Formazan-based assays (MTT/XTT), Green fluorescent protein, Lactate dehydrogenase (LDH), Methyl violet, Propidium iodide, DNA stain that can differentiate necrotic, apoptotic and normal cells, Resazurin, Trypan Blue (a living-cell exclusion dye (dye only crosses cell membranes of dead cells)), TUNEL assay, cell labeling or staining (e.g., a cell-permeable dye (e.g., Carboxylic Acid Diacetate, Succinimidyl Ester (Carboxy-DFFDA, SE)), a cell-impermeable dye, cyanine, phenantridines, acridines, indoles, imidazoles, a nucleic acid stain, a cell permeant reactive tracer (e.g., intracellularly-activated fluorescent dyes CMRA, $CMF_2HC$ (4-Chloromethyl-6,8-Difluoro-7-Hydroxycoumarin), CMFDA (5-Chloromethylfluorescein Diacetate), CMTMR (5-(and -6)-(((4-Chloromethyl)Benzoyl)Amino) Tetramethylrhodamine), CMAC (7-Amino-4-Chloromethylcoumarin), CMHC (4-Chloromethyl-7-Hydroxycoumarin)) or any combinations thereof), fluorescent DNA dyes (e.g., DAPI, Heochst family, SYBR family, SYTO family (e.g., SYTO 9), SYTOX family (e.g., SYTOX green), ethidium bromide, propidium iodide, acridines, or any combinations thereof); chromogenic dyes (e.g., eosin, hematoxilin, methylene blue, azure, or any combinations thereof); cytoplasma stain (e.g., calcofluor white, periodic acid-schiff stain, or any combinations thereof); metabolic stains (e.g., any metabolic stains described herein, any diacetate dye (including, rhodamine based-dye, fluorescin, or any combinations thereof), resazurin/resorufin (alamar blue); ROS stains (e.g., any ROS stains described herein, DCFDA and related family, calcein-acetoxymethyl and related family); membrane stains (e.g., bodipy, FM 1-43, FM 4-64, and functionally equivalent thereof, CellMask™ stains, DiI, DiO, DiA); biologic stains (e.g., labeled antibodies, labeled chitin-binding protein), optical imaging, microscopic imaging after staining, ELISA, mass spectrometric analysis (e.g., of peptides, proteins, glycopeptides, lipopeptides, carbohydrates, and/or metabolites), modification of metabolomic fingerprint, degradation of RNA or of protein content and the like. In some embodiments, the detection of the growth or functional response of the microbe to the antibiotic agent can be done using solid phase, microfluidics or droplet based assays. In one embodiment, the detection of the growth or functional response of the microbe to the antibiotic agent can comprise use of a mass spectrometer. In one embodiment, the detection of the growth or functional response of the microbe to the antibiotic agent can comprise detection of at least one metabolite, or a metabolic profile. In one embodiment, the detection of the growth or functional response of the microbe to the antibiotic agent can comprise detection of transcriptional changes.

As used herein, the term "cell permeant reactive tracer" refers to a molecule that can diffuse freely through membranes of live cells and yield a fluorescent product that can generally be retained in the live cells through several generations. In some embodiments, the fluorescent product retained in live cells cannot be transferred to adjacent cells in a population. In some embodiments, the fluorescent product retained in live cells can be transferred to adjacent cells, e.g., by transport through gap junctions. In some embodiments, cell permeant reactive tracer prior to diffusing through the membranes of live cells can remain non-fluorescent until the molecule diffuses into the cells and processed inside the cells, e.g., by an enzymatic reaction inside the cells. In some embodiments, the cell permeant reactive tracer prior to diffusing through the membranes of live cells can be fluorescent. Examples of cell permeant reactive tracers can include, but are not limited to, thiol-reactive tracers (e.g., but are not limited to, fluorescent 7-aminocoumarin (e,g,m CMAC), fluorescent 7-hydroxycoumarin (CMHC), fluorescent 6,8-difluoro-7-hydroxycoumarin (CMF$_2$HC), fluorescent 2,3,6,7-tetrahydro-9-bromomethyl-1H,5H-quinolizino(9,1-gh)coumarin (BMQC), fluorescent fluorescein diacetate (CMFDA), fluorescent BODIPY derivative (BODIPY), fluorescent tetramethylrhodamine (CMTMR), fluorescent CMRA, fluorescent CMTPX, chloromethyl derivatives of SNARF-1 and H$_2$DCFDA, bimanes, or any combinations thereof), amine-reactive tracers (e.g., but are not limited to, CFSE and its derivatives, carboxylic acid diacetate succinimidyl ester, DDAO-SE, SNARF-1 carboxylic acid acetate, or any combinations thereof), or any combinations thereof. In some embodiments, any commercially-available cell tracers, probes and/or dyes (e.g., but not limited to, from INVITROGEN) can be used to label the cell and/or determine cell viability.

Labeling molecules which bind with the microbe can be also be used to label the microbes for detection. As used herein, a "labeling molecule" refers to a molecule that comprises a detectable label and can bind with a target microbe. Labeling molecules can include, but are not limited to, MBL, FcMBL, AKT-FcMBL, wheat germ agglutinin, lectins, antibodies (e.g., gram-negative antibodies or gram-positive antibodies, antibiotics to specific microbial strains or species), antigen binding fragments of antibodies, aptamers, ligands (agonists or antagonists) of cell-surface receptors and the like. The labeling molecule can be a non-specific labeling molecule that non-specifically stains all viable cells in a sample.

As used herein, the term "detectable label" refers to a composition capable of producing a detectable signal indicative of the presence of a target. Detectable labels include any composition detectable by spectroscopic, photochemical, biochemical, immunochemical, electrical, optical or chemical means. Suitable labels include fluorescent molecules, radioisotopes, nucleotide chromophores, enzymes, substrates, chemiluminescent moieties, bioluminescent moieties, and the like. As such, a label is any composition detectable by spectroscopic, photochemical, biochemical, immunochemical, electrical, optical or chemical means needed for the methods and devices described herein.

A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP(Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 Ca2+ Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CFDA; CFP—Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; Cy2™; Cy3.18; Cy3.5™; Cy3™; Cy5.18; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); DIDS; Dihydrorhodamine 123 (DHR); DiO (DiOC18(3)); DiR; DiR (DiIC18(7)); Dopamine; DsRed; DTAF; DY-630—NHS; DY-635—NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP(S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; C12 resorufin derivative; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; TruRed; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used.

Other exemplary detectable labels include radiolabels (e.g., $^{3}H$, $^{125}I$ $^{35}S$, $^{14}C$, or $^{32}P$), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

In some embodiments, the detectable label is a fluorophore or a quantum dot. Without wishing to be bound by a theory, using a fluorescent reagent can reduce signal-to-noise in the imaging/readout, thus maintaining sensitivity. Accordingly, in some embodiments, prior to detection, the microbial subsamples/cultures, e.g., after incubation, can be stained with at least one stain, e.g., at least one fluorescent staining reagent comprising a microbe-targeting molecule, wherein the microbe-targeting molecule comprises a fluorophore or a quantum dot. Examples of fluorescent stains include, but are not limited to, any microbe-targeting element (e.g., microbe-specific antibodies or any microbe-detecting proteins or peptides or oligonucleotides) typically conjugated with a fluorophore or quantum dot, and any fluorescent stains used for detection as described herein.

In some embodiments, a labeling molecule can be configured to include a "smart label", which is undetectable when conjugated to the microbe-targeting molecules, but produces a color change when released from the engineered molecules in the presence of a microbe enzyme. Thus, when a microbe binds to the engineered microbe-targeting molecules, the microbe releases enzymes that release the detectable label from the engineered molecules. An observation of a color change indicates presence of the microbe in the sample.

In some embodiments, the microbe-targeting solid substrate can be conjugated with a label, such as a detectable label or a biotin label.

In some embodiments, the labeling molecule comprises MBL or a microbe-targeting molecule described herein. In one embodiment, the labeling molecule comprises FcMBL. Without wishing to be bound by a theory, labeling molecules based on MBL, and FcMBL in particular, attach selectively to a broad range of microbes or pathogens, and so they enable the method described herein to detect the majority of blood-borne microbes (e.g., pathogens) with high sensitivity and specificity.

Any method known in the art for detecting the particular label can be used for detection. Exemplary methods include, but are not limited to, spectrometry, fluorometry, microscopy imaging, immunoassay, and the like. While the capture extraction step can specifically extract microbes, it can be beneficial to use a labeling molecule that can enhance this specificity. If imaging, e.g., microscopic imaging, is to be used for detecting the label, the staining can be done either prior to or after the microbes have been laid out for microscopic imaging. Additionally, imaging analysis can be performed via automated image acquisition and analysis.

For optical detection, including fluorescent detection, more than one stain or dye can be used to enhance the detection or identification of the microbe. For example, a first dye or stain can be used that can bind with a genus of microbes, and a second dye or strain can be used that can bind with a specific microbe. Co-localization of the two dyes then provides enhanced detection or identification of the microbe by reducing false positive detection of microbes.

In some embodiments, microscopic imaging can be used to detect signals from label on the labeling agent. Generally, the microbes in the subsample are stained with a staining reagent and one or more images taken from which an artisan can easily count the number of cells present in a field of view. By way of example only, microscopy of fluorescently stained bacteria can yield images from which one skilled in the art can easily count the number of bacterial cells present in a field of view. In some embodiments, the use of high content screening imagers is particularly well-adapted to the time-lapse observation of microbe behavior after exposure to antibiotic agents. For example, the Hermes WiScan automated imaging/high content screening system can allow the automated observation of glass-bottom microplates.

Without wishing to be bound by theory, since microscopy generally works best when the sample is presented as a flat layer (so that the entire image is within the microscope's depth of field), care should be taken to present the sample suitably. For example, the sample (containing microbes) can be presented on a surface of a separation device that is used to isolate the bound microbes (e.g., microbes bound to a microbe-targeting substrate) from a biological fluid (e.g., on the surface of a magnetic element used for magnetic separation), in a microfluidic channel or slide-coverslip sandwich with a small channel-height/gap, or after filtration through a membrane-type filter. One advantage of using membrane filters is that they can also be used to remove any of the microbe-targeting substrates that are not bound to a microbe or pathogen, hence removing potential obstructions. Filtration cells that allow in situ imaging of the captured microbes can also be used.

In some embodiments, microbe can be detected through use of one or more enzyme assays, e.g., enzyme-linked assay (ELISA). Numerous enzyme assays can be used to provide for detection. Examples of such enzyme assays include, but are not limited to, beta-galactosidase assays, peroxidase assays, catalase assays, alkaline phosphatase assays, and the like. In some embodiments, enzyme assays can be configured such that an enzyme will catalyze a reaction involving an enzyme substrate that produces a fluorescent product. Enzymes and fluorescent enzyme substrates are known and are commercially available (e.g., Sigma-Aldrich, St. Louis, Mo.). In some embodiments, enzyme assays can be configured as binding assays that provide for detection of microbe. For example, in some embodiments, a labeling molecule can be conjugated with an enzyme for use in the enzyme assay. An enzyme substrate can then be introduced to the one or more immobilized enzymes such that the enzymes are able to catalyze a reaction involving the enzyme substrate to produce a detectable signal.

In some embodiments, an enzyme-linked assay (ELISA) can be used to detect signals from label on the labeling molecule. In ELISA, the labeling molecule comprises an enzyme as the detectable label. Each labeling molecule can comprise one or more (e.g., 1, 2, 3, 4, 5, 6, 7, 8, 9, 10 or more) enzymes. Additionally, each labeling molecule can comprise one or more (e.g., 1, 2, 3, 4, 5, 6, 7, 8, 9, 10 or more) sites for binding with a microbe. Without wishing to be bound by a theory, presence of multimeric probe molecules can enhance ELISA signal.

For ELISA, any labeling molecule conjugated to an enzyme can be used. Exemplary labeling molecule include those comprising MBL, FcMBL, Akt-FcMBL, wheat germ agglutinin, lectins, antibodies (e.g., gram-negative antibodies or gram-positive antibodies), antigen binding fragments of antibodies, aptamers, ligands (agonists or antagonists) of cell-surface receptors and the like.

In some embodiments, the labeling molecule comprises MBL or FcMBL labeled with a detectable label.

Similarly, a variety of enzymes can be used, with either colorimetric or fluorogenic substrates. In some embodiments, the reporter-enzyme produces a calorimetric change which can be measured as light absorption at a particular wavelength. Exemplary enzymes include, but are not limited to, beta-galactosidases, peroxidases, catalases, alkaline phosphatases, and the like.

In some embodiments, the enzyme is a horseradish peroxidase (HRP).

A microbe-targeting molecule and the enzyme can be linked to each other by a linker. In some embodiments, the linker between the microbe-targeting molecule and the enzyme is an amide bond. In some embodiments, the linker between the microbe-targeting molecule and the enzyme is a disulfide (S—S) bond.

When the microbe-targeting molecule is a peptide, polypeptide or a protein, the enzyme can be linked at the N-terminus, the C-terminus, or at an internal position of the microbe-targeting molecule. Similarly, the enzyme can be linked by its N-terminus, C-terminus, or an internal position.

In one embodiment, the ELISA probe molecule comprises a MBL or FcMBL molecule linked to a HRP. The FcMBL-HRP construct can be generated using Lightning-Link® HRP Conjugation Kit (Innova Biosciences) a proprietary lyophilized HRP mixture for directional coupling to antibodies and other proteins. It is to be understood that creation of FcMBL-HRP is not limited to this kit as any labeling procedure for antibodies well known in the known art can be used.

Following incubation with the probe-molecule, the subsample can be washed one or more (e.g., 1, 2, 3, 4, 5 or more) times to remove any unbound probes. The enzyme's substrate can be added and the assay developed.

One advantage of the ELISA-based approach is that the solid substrate does not need to be dispersed or dissociated from the microbe before binding the secondary reagents. This is in contrast to microscopic techniques, in which excess residual solid substrate may obscure the microbe during imaging. Furthermore, the optical readout components for ELISA are likely cheaper than in the microscopy case, and there is no need for focusing or for demanding that the sample be on the same focal plane. A further advantage of the ELISA-based approach is that it can take advantage of commercially available laboratory equipment. In particular, when the solid substrate is magnetic, magnetic separation can be automated using the KINGFISHER® system, the brief culture can be performed using an airlift fermenter, and the colorimetric/fluorescent readout can be attained using a standard plate reader.

Further amplification of the ELISA signal can be obtained by multimerizing the recognition molecule (i.e., the microbe-targeting molecule) or by multimerizing the detection enzyme (HRP, etc.). For instance, phage expression can be used to yield multimerized MBL and provide a scaffold to increase the concentration of HRP (either through direct coupling of HRP to the phage particles or using an HRP-antiM13 conjugated antibody).

In some embodiments, microbe can be detected through use of immunoassay. Numerous types of detection methods may be used in combination with immunoassay based methods.

Detection of microbes in a subsample can also be carried out using light microscopy with phase contrast imaging based on the characteristic size (5 um diameter), shape (spherical to elliptical) and refractile characteristics of target components such as microbes, for example, in the case of fungi that are distinct from all normal blood cells. Greater specificity can be obtained using optical imaging with fluorescent or cytochemical stains that are specific for all microbes or specific subclasses (e.g. calcofluor (1 µM to 100 µM) for chitin in fungi, fluorescent antibodies directed against fungal surface molecules, gram stains, acid-fast stains, fluorescent MBL, fluorescent Fc-MBL, etc.).

Microbe detection can also be carried out using an epifluorescent microscope to identify the characteristic size (5 um diameter), shape (spherical to elliptical) and staining characteristics of microbes. For example, fungi stain differently from all normal blood cells, strongly binding calcofluor (1 μM to 100 μM) and having a rigid ellipsoid shape not found in any other normal blood cells.

In some embodiments, microbe can be detected through use of spectroscopy. Numerous types of spectroscopic methods can be used. Examples of such methods include, but are not limited to, ultraviolet spectroscopy, visible light spectroscopy, infrared spectroscopy, x-ray spectroscopy, fluorescence spectroscopy, mass spectroscopy, plasmon resonance (e.g., Cherif et al., Clinical Chemistry, 52:255-262 (2006) and U.S. Pat. No. 7,030,989; herein incorporated by reference), nuclear magnetic resonance spectroscopy, Raman spectroscopy, fluorescence quenching, fluorescence resonance energy transfer, intrinsic fluorescence, ligand fluorescence, and the like.

In some embodiments, microbe can be detected through use of fluorescence anisotropy. Fluorescence anisotropy is based on measuring the steady state polarization of sample fluorescence imaged in a confocal arrangement. A linearly polarized laser excitation source preferentially excites fluorescent target molecules with transition moments aligned parallel to the incident polarization vector. The resultant fluorescence is collected and directed into two channels that measure the intensity of the fluorescence polarized both parallel and perpendicular to that of the excitation beam. With these two measurements, the fluorescence anisotropy, r, can be determined from the equation: r=(Intensity parallel-Intensity perpendicular)/(Intensity parallel+2(Intensity perpendicular)) where the I terms indicate intensity measurements parallel and perpendicular to the incident polarization. Fluorescence anisotropy detection of fluorescent molecules has been described. Accordingly, fluorescence anisotropy can be coupled to numerous fluorescent labels as have been described herein and as have been described in the art.

In some embodiments, microbe can be detected through use of fluorescence resonance energy transfer (FRET). Fluorescence resonance energy transfer refers to an energy transfer mechanism between two fluorescent molecules. A fluorescent donor is excited at its fluorescence excitation wavelength. This excited state is then nonradiatively transferred to a second molecule, the fluorescent acceptor. Fluorescence resonance energy transfer may be used within numerous configurations to detect captured microbe. For example, in some embodiments, a first labeling molecule can be labeled with a fluorescent donor and second labeling molecule can be labeled with a fluorescent acceptor. Accordingly, such labeled first and second labeling molecules can be used within competition assays to detect the presence and/or concentration of microbe in a sample. Numerous combinations of fluorescent donors and fluorescent acceptors can be used for detection.

In some embodiments, microbe can be detected through use of polynucleotide analysis. Examples of such methods include, but are not limited to, those based on polynucleotide hybridization, polynucleotide ligation, polynucleotide amplification, polynucleotide degradation, and the like. Methods that utilize intercalation dyes, fluorescence resonance energy transfer, capacitive deoxyribonucleic acid detection, and nucleic acid amplification have been described, for example, in U.S. Pat. No. 7,118,910 and No. 6,960,437; herein incorporated by reference). Such methods can be adapted to provide for detection of one or more microbe nucleic acids. In some embodiments, fluorescence quenching, molecular beacons, electron transfer, electrical conductivity, and the like can be used to analyze polynucleotide interaction. Such methods are known and have been described, for example, in Jarvius, DNA Tools and Microfluidic Systems for Molecular Analysis, Digital Comprehensive Summaries of Uppsala Dissertations from the Faculty of Medicine 161, ACTA UNIVERSITATIS UPPSALIENSIS UPPSALA 2006, ISBN: 91-554-6616-8; Singh-Zocchi et al, Proc. Natl. Acad. Sci, 100:7605-7610 (2003); Wang et al. Anal. Chem., 75:3941-3945 (2003); and Fan et al, Proc. Natl. Acad. Sci, 100:9134-9137 (2003) and in U.S. Pat. Nos. 6,958,216; No. 5,093,268; and U.S. Pat. No. 6,090,545, the content of all of which is incorporated herein by reference. In some embodiments, the polynucleotide analysis is by polymerase chain reaction (PCR). The fundamentals of PCR are well-known to the skilled artisan, see, e.g. McPherson, et al., *PCR, A Practical Approach*, IRL Press, Oxford, Eng. (1991), hereby incorporated by reference.

In some embodiments, a metabolic assay is used to determine the relative number of microbes in a subsample compared to a control. As will be apparent to one of ordinary skill in the art any metabolic indicator that can be associated with cells can be used, such as but not limited to, turbidity, fluorescent dyes, and redox indicators such as, but not limited to, AlamarBlue, MTT, XTT, MTS, and WST. Metabolic indicators can be components inherent to the cells or components added to the environment of the cells. In some embodiments, changes in or the state of the metabolic indicator can result in alteration of ability of the media containing the sample to absorb or reflect particular wavelengths of radiation.

Exemplary metabolic assays include, but are not limited to, ATP Luminescence, reactive oxygen species (ROS) assays, Resazurin assays, Luminol, MTT-metabolic assays, and the like. Further, as one of skill in the art is well aware, kits and methods for carrying out metabolic assays are commercially available. For example, 2-(N-(7-Nitrobenz-2-oxa-1,3-diazol-4-yl)Amino)-2-Deoxyglucose (2-NBDG), ATP Determination Kit, AMPLEX® Red Galactose/Galactose Oxidase Assay Kit, AMPLEX® Red Glucose/Glucose Oxidase Assay Kit, AMPLEX® Red Glutamic Acid/Glutamate Oxidase Assay Kit, AMPLEX® Red Hydrogen Peroxide/Peroxidase Assay Kit, AMPLEX® Red Monoamine Oxidase Assay Kit, AMPLEX® Red Neuraminidase (Sialidase) Assay Kit, AMPLEX® Red Phosphatidylcholine-Specific Phospholipase C Assay Kit, AMPLEX® Red Sphingomyelinase Assay kit, AMPLEX® Red Uric Acid/Uricase Assay Kit, AMPLEX® Red Xanthine/Xanthine Oxidase Assay Kit, THIOLTRACKER™ Violet (Glutathione Detection Reagent), THIOLTRACKER™ Violet (Glutathione Detection Reagent), and VYBRANT® Cell Metabolic Assay Kit from Invitrogen; Adenosine 5'-triphospahte (ATP) Luminescence Assay Kit (ENLITEN® from Promega; ATPLITE™ from PerkinElmer Life Sciences; ATP Bioluminescence Assay kit HS II from Boehringer Mannheim, Germany; Adenosine 5'-triphosphate (ATP) Luminescence Assay Kit from EMD Millipore; Reactive Oxygen Species (ROS) Assays from Cell BioLabs, Inc.; Cellular Reactive Oxygen Species Detection Assay Kit from ABCAM®; hROS Detection Kit from Cell Technology, Inc.; and ABTS Antioxidant Assay Kit, ORAC Antioxidant Assay Kit, OxiSelect HORAC Activity Assay Kit, OxiSelect In Vitro ROS/RNS Assay Kit (Green Fluorescence), OxiSelect Intracellular ROS Assay Kit (Green Fluorescence), OxiSelect ORAC Activity Assay Kit, OxiSelect Total Antioxidant Capacity (TAC) Assay Kit, and Total Antioxidant Capacity Assay Kit from BioCat.

In some embodiments, microbe detection and/or identification can use one or more embodiments of the compositions and/or methods described in the International Application No. PCT/US12/71398 filed Dec. 21, 2012, content of which is incorporated herein by reference.

In some embodiments, the assay or process 1200 described herein can be adapted for use in a high-throughput platform, e.g., an automated system or platform. For example, in some embodiments, one or more multi-well plates (e.g., 96 and/or 384 wells), each well of which comprises a gel matrix and/or detection substrate with different antibiotic profiles, can be set up on an imaging platform. In other embodiments, multiple capillary gel matrices (e.g., in a microfluidic device) with antibiotic profiles can be set up on an imaging platform. Coordinates of each individual microbe can be determined, e.g., by imaging, prior to addition of at least one antibiotic agent. During and/or after incubation in the antibiotic agent for a period of time, responses of the individual microbes to the antibiotic agent can be monitored in real-time, e.g., by imaging a color change/shift of a metabolic indicator or dye. In addition, based on the previous recorded coordinates, the same microbes can be tracked during and/or after antibiotic incubation to determine their individual response.

Comparison with Reference or Control

In some embodiments, the antibiotic sensitivity testing methods described herein are based on the direct measurement of microbe's ability to grow in the presence of the tested antibiotics. This direct measurement can provide the clinically relevant result that the physicians require for selecting a treatment regimen, even without identifying the causative microbes or pathogens, and is thus generally superior to methods that test for indirect properties (e.g. presence of antibiotic-resistance genes or enzymes).

While similar to blood culture methods currently employed in the art, the antibiotic sensitivity testing method described herein is able to detect microbes and their antibiotic agent sensitivity using shorter growth times. Without wishing to be bound by a theory, this is, in part, enabled by the ability of microbe-targeting molecules (e.g., MBL, FcMBL, or Akt-FcMBL) to capture the microbes and thus to concentrate them from a biological fluid. Further, the ability of the microscopic approach to detect and quantify small numbers of microbial cells (e.g., bacterial cells), and in turn, small difference in microbial counts (e.g., bacterial counts) can increase the sensitivity of the detection. Consequently, whereas blood-culture based antibiotic resistance testing methods typically requires three lengthy incubation steps, some embodiments of the antibiotic sensitivity testing method described herein can require only one short incubation step.

In some embodiments, the antibiotic sensitivity testing methods described herein are based on the direct measurement of microbe's ability to undergo a metabolic change (e.g. production of ROS, change in ATP or pH levels) in response to an antibiotic that is directly related to its loss of viability or induction of death, without producing a change in cell growth (i.e., change in cell number).

Once cell counts (e.g., microbe or pathogen counts) or functional response level for the reference or control (i.e., the microbes or pathogens cultured in the absence of any antibiotic agent) and antibiotic agent-treated subsamples have been determined, degree of antibiotic resistance can be determined by comparing these numbers. For example, subsamples that display cell counts or functional response level similar (e.g., within 0.5%, 1%, 1.5%, 2%, 2.5%. 3%, 3.5%, 4%, 4.5%, 5%, 5.5%, 6%, 6.5%, 7%, 7.5%, 8%, 8.5%, 9%, 9.5%, 10%, 15%, 20%, or any statistically significant determination) to the reference count can indicate that they are resistant to the antibiotic agent with which they were treated, and thus their growth is unencumbered.

Subsamples in which growth can be antibiotic agent inhibited, in contrast, do not benefit from the incubation time, and therefore, their cell counts or functional response levels are generally lower, for example, by at least about 5%, at least about 10%, at least about 15%, at least about 20%, at least about 25%, at least about 30%, at least about 35%, at least about 40%, at least about 45%, at least about 50%, at least about 55%, at least about 60%, at least about 70%, at least about 80%, at least about 90%, at least about 95% or higher, as compared to the reference or control.

In some embodiments, if one antibiotic agent treated subsample has a higher microbial or bacterial count than another antibiotic agent treated subsample, e.g., by at least about 5%, at least about 10%, at least about 20%, at least about 30% or higher, it can indicate that the microbes are more resistant to the former than the latter.

Based on the microbial count numbers or functional response among the subsamples of microbes isolated from a biological fluid of a subject, in some embodiments, a skilled practitioner, e.g., a physician, can prescribe or administer to the subject in need thereof an antibiotic agent or a combination of antibiotic agent to which reduced the cell number or functional response level by at least about 5%, at least about 10%, at least about 15%, at least about 20%, at least about 25%, at least about 30%, at least about 35%, at least about 40%, at least about 45%, at least about 50%, at least about 55%, at least about 60%, at least about 70%, at least about 80%, at least about 90%, at least about 95% or higher, as compared to a reference. In some embodiments, a skilled practitioner (e.g., a physician) can prescribe or administer to the subject in need thereof an antibiotic agent or a combination of antibiotic agents that has yielded the highest reduction in cell count or functional response level, as compared to a reference.

In some embodiments, there can be substantially no change in the cell count or functional response level in the reference subsample (i.e., microbes cultured in the absence of any antibiotics), which can indicate that the subject does not have any microbial infection and thus no treatment is required. In some embodiments, there can be substantially no change in the cell count or functional response level in the reference subsample (i.e., microbes cultured in the absence of any antibiotics), which does not exclude the presence of microbes whose growth is not supported by the test media.

In some embodiments, more than one types of microbial detection (e.g., bacterial and fungal detection) can be combined into the same antibiotic sensitivity testing method (e.g. bacterial detection, fungal detection, and antibiotic sensitivity) as described herein.

In some embodiments, a reference or control used in the assay described herein can refer to a sample comprising a portion of the microbe (e.g., pathogen) captured and isolated from a biological sample and subjected to substantially the same microbial culture condition in the absence of an antibiotic.

In some embodiments, a reference or control used in the assay described herein can refer to the number of viable microbes (e.g., viable pathogens) initially present in a subsample (e.g., viable cell count) before incubation with an antibiotic.

An Embodiment of the Assay

An exemplary protocol for determining the antibiotic susceptibility of a microbe (e.g., a pathogen) directly from a test sample is as follows:
  (i) Collect test sample (e.g., blood in a heparin tube);
  (ii) Add an excess of heparin (e.g., about 1 mg of additional heparin for each ml of test sample;
  (iii) Dilute test sample about 1:1 with 1×TBST $Ca^{2+}$;

(iv) Add about 5-7 µl (2 mg/ml) of Akt-FcMBL beads for each ml of test sample;
(v) Incubate for about 20 minutes at about room temperature with mixing;
(vi) Separate the beads with attached bacteria from test sample;
(vii) Washing the beads (about 3 times) in 1×TBST $Ca^{2+}$; at this step outgrowth or culture/cell expansion can be performed if necessary to reach sufficient numbers for sample division;
(viii) Divide the bead sample substantially equally into growth media with or without antibiotic (possible because of additional heparin);
(ix) Grow for 1 to 8 hours (dependent on species or titer);
(x) Measure viability (e.g., ATP generation) at each hour until antibiotic susceptibility determined; and
(xi) Optionally perform additional testing (residual growth available for additional tests).

Alternative Embodiment of the Assay

An exemplary protocol for determining the antibiotic susceptibility from individual microbes is as follows:

(1) Capture of Microorganisms or Microbes (e.g., Bacteria or Pathogens):

Microorganisms are extracted and purified from a clinical sample using capture beads coated with Akt-FcMBL (e.g., 1 µM MyONE T1 streptavidin beads coated with biotinylated Akt-FcMBL). Alternatively, capture beads can also be coated with a specific (antibody) or other nonspecific lectin or other agent by physical or chemical means relevant to the type of sample processed.

An exemplary sample capture protocol:
10 µl of a bacterial dilution are added to 1×TBST $Ca^{2+}$5 mM with 10 µl of Akt-FcMBL magnetic beads (2 mg/ml).
Bacteria are captured by mixing, e.g., ~10 minutes on Hula mixer
Bead/bacteria are washed at least 3 times in TBST 5 mM $Ca^{2+}$
Optional outgrowth or culture/cell expansion of bacteria from microbe-poor or microbe-rare samples
Bead/bacteria are resuspended in 100 µl TBST 5 mM $Ca^{2+}$
2 µl of bead/bacteria are used for each subsample (2) Labeling of the Microorganisms (Optional):

Specific or non-specific tags (e.g., fluorescent beads or any compound not compromising bacterial metabolism) can be used to label bacteria.

For example, 2 µl of biotin Akt-FcMBL coated 40 nm FluoSpheres (505/515-Life Technologies) can be used to label bacteria. The labeled bead/bacteria are washed at least 2 times to remove unbound FluoSpheres and resuspended at desired concentrated suspension for use as described in the step above. In some embodiments, the tagged bacteria from the specimen can be concentrated in a suspension.

(3) Metabolic Detection Substrate or Dyes:

A metabolic detection substrate is made by immobilizing one or many indicators of bacterial metabolism. In such embodiments, gels can be reactive to bacterial metabolism and/or death and/or growth that can be analyzed using a microscope (e.g., a fluorescent microscope).

For example: Inclusion of Resazurin and Sytox Green 11 in a ~0.5 mm thick 3.0% NUSIEVE® agarose gel in TBS-T/$Ca^{2+}$5 mM over a microscope coverslip can be used for this embodiment of the assay described herein. Use of alternate dyes or indicators such as Syto9 or Propidium Iodine in a more controlled hydragel can also be used. Additionally or alternatively, covalent binding of such indicators of bacterial metabolism to a surface can also be used.

Addition of nutrients to the detection substrate gel can be done at this stage to incorporate the nutrients in the matrix or they can be added later to the gel for diffusion of nutrients.

An identical test gel containing the aforementioned compounds plus a given concentration of one or more tested antimicrobial agents is provided. Combinations of antimicrobial agents can also be evaluated.

(4) Addition and Incubation of Captured Bacteria to the Test Gel Samples:

At this stage, captured bacteria (e.g., captured fluorescent bacteria, if labeled) are cultured on a surface reactive to bacterial metabolism in the presence or absence of the tested antimicrobial agent or by addition of antimicrobial agent following detection of growth.

For example, the cell suspension from stage (2) can be applied to detection substrate gel from stage (3) and overlaid with a nutrient low melt gel not interfering with metabolic detection (TBS-T/$Ca^{++}$5 mM, 0.5% agarose gel, Brain/Heart Infusion (BHI) broth). Alternatively, the bead/bacteria suspension from stage (2) can be added to an imaging compatible surface (for example, a glass coverslip or a multi-well plate, e.g., 96 well dish) immobilized by a magnet and overlaid with a low melt agarose or other matrix containing appropriate reagents and growth media (example: TBS-T/$Ca^{++}$5 mM 3.0% NUSIEVE® agarose gel, Brain Heart Infusion (BHI) broth, Resazurin, and Sytox Green 11). The gel once set is incubated at 37° C. and imaged in real time.

(5) Fluorescent Microscope Read of the Susceptibility to the Antimicrobial Agent:

After incubation for a pre-determined period of time, e.g., for about an hour or less, a microbe's biological response to the antimicrobial agent (e.g., metabolic activity, growth and/or cell viability) can be detected.

For example, the microscope can be focused on the tested bacteria to detect fluorescence from the tag of bacteria, if it was labeled in stage (2), (or luminescence or radiological decay or magnetic spin or other, depending on the labeling molecule or tag applied in stage (2)). In some embodiments, the bacteria can be labeled with fluorescent nanospheres coated with Fc-MBL (FluoSpheres, excitation 515 nm/emission 535 nm, Life Technologies).

Additionally or alternatively, the fluorescence (or luminescence or radiological decay or magnetic spin or other) of the metabolic detection substrates or dyes can be measured.

For example: The reduction of resazurin to resorufin (560 nm excitation/590 nm emission) by bacteria can be detected on the control gel not containing antibiotics, whereas the abolition of the background noise is detected on the antibiotic containing gel.

Figure 16:
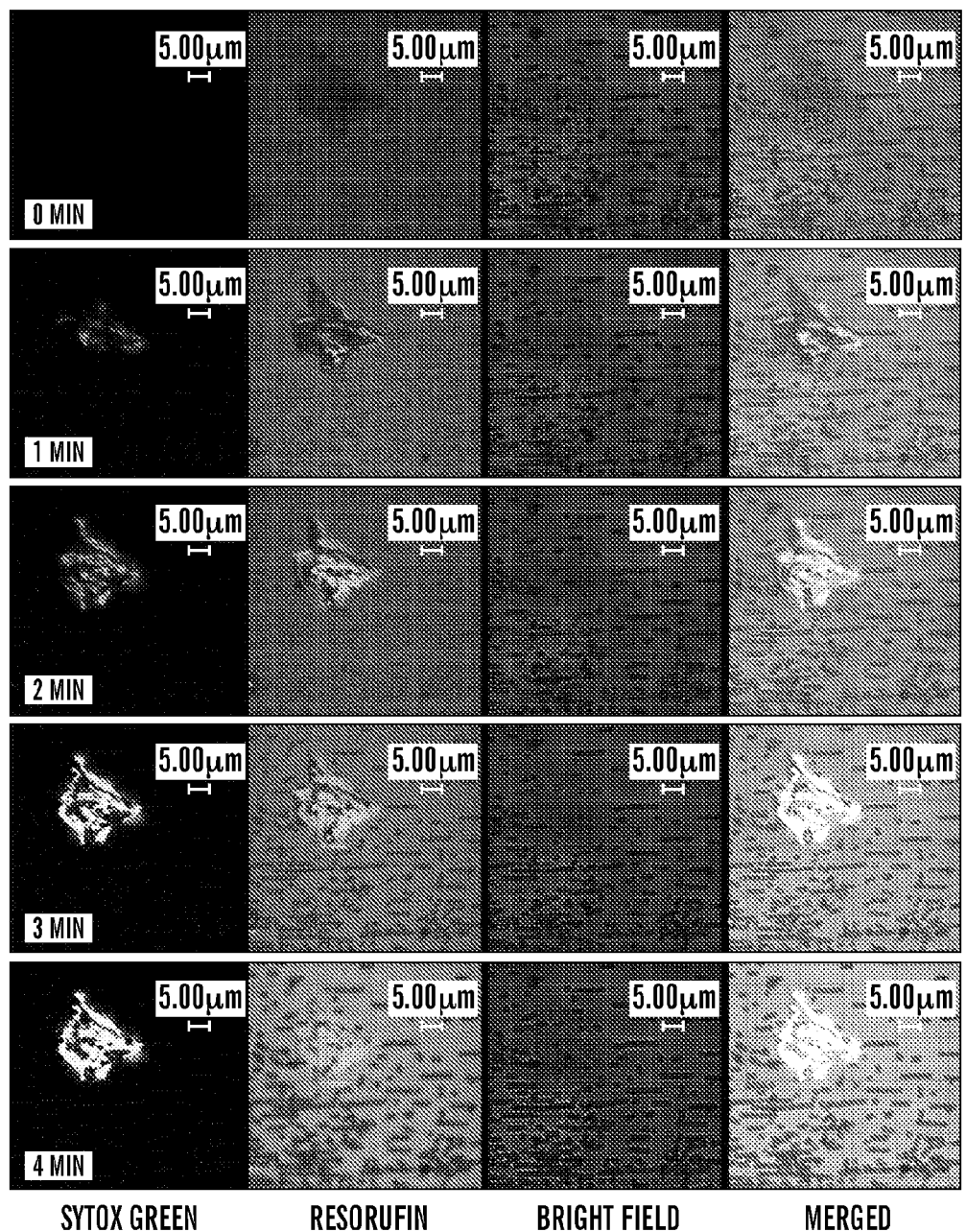
FIG. 16 is a set of images showing results of an individual cell antibiotic susceptibility testing (microcolony-based antibiotic susceptibility testing) according to one embodiment described herein. $E.\ coli$ were captured on 1 μm FcMBL-coated magnetic beads and overlaid with alginate gel, stains for labeling live (e.g., resazurin stain) or dead (e.g., Sytox green stain) cells (live/dead stains), and growth media, e.g., RPMI 1640. Viability was assessed at indicated time points after addition of about 128 mg/L carbenicillin. The microcolony-based AST can antibiotic susceptibility data within minutes, enabling selecting bateriocidal compounds within the clinically relevant time frame.

Alternative example: The reduction of resazurin to resorufin (560 nm excitation/590 nm emission) by bacteria can be detected before addition of antimicrobial agent. The coordinates of the bacteria on an imaging surface are recorded and media including antimicrobial is then added. Bacteria can be detected for switch between resorufin detection (red) to detection of Sytox Green 11 uptake (green). A red to green shift indicating antibiotic activity (e.g., as shown in FIG. 16)

(6) Identification of the Captured Microbe (Optional):

Addition of specific fluorescent identification markers or transfer to MALDI-TOF MS identification of the tagged microorganism or in situ PCR can provide complete microbiological documentation of an infection in 3 hours or less instead of the current 48 hours that are the current standard of care. Decreasing such a turn-around time can improve patient outcome and increase survival of the patient in intensive care infectious diseases and septic shock.

Microbe-Targeting Substrate

Suitable microbe-targeting substrate can be fabricated from a wide variety of materials and in a variety of formats. For example, solid substrates can be utilized in the form of beads (including polymer beads, magnetic beads or particles, and the like), nanoparticles, microparticles, filters, fibers, screens, mesh, tubes, hollow fibers, microfluidic channels, membranes, nucleic acid scaffolds, protein scaffolds, lipid scaffolds, dendrimers, nanoparticles, microtiter plates, nanotubes, magnetic particles, microchips, filtration devices, diagnostic strips, dipsticks, extracorporeal devices, spiral mixers, and other like substrates commonly utilized in assay formats, and any combination thereof. The particular format of the solid substrate is not critical to the invention. The solid substrate is preferably chosen to maximize signal-to-noise ratios, primarily to minimize background binding, as well as for ease of separation of reagents and cost. Without wishing to be bound by a theory, substrates having defined surface chemistry can be used to minimize chemical agglutination and non-specific binding.

In some embodiments, the microbe-targeting substrate is a particle, e.g., a nano- or microparticle. The particle can be of any shape, including but not limited to spherical, rod, elliptical, cylindrical, disc, shell, and prism and these can be part of a network. The term "particle" as used herein refers to a particle having a size of about 1 nm to about 1 mm in size. For example, a particle can be from about 0.005 µm to about 500 µm, about 0.01 µm to about 250 µm, about 0.05 µm to about 100 µm, about 50 nm to about 250 µm, about 50 nm to about 50 µm, about 50 nm to about 1 µm, about 80 nm to about 750 µm. In one embodiment, the particle is about 25 nm to about 250 nm, or about 90 nm to about 200 nm in size. In one embodiment, the particle can be about 0.1 µm to about 10 µm or about 0.5 µm to about 5 µm.

In some embodiments, the particle can be a sphere. As used herein, the term "sphere" refers to a particle having a substantially spherical form. A substantially spherical particle is a particle with a difference between the smallest radii and the largest radii generally not greater than about 40% of the smaller radii, and more typically less than about 30%, less than 20%, less than 15%, less than 10%, or less than 5%.

In some embodiments, the microbe-targeting substrate is a nanoparticle. As used herein, the term "nanoparticle" refers to particles that are on the order of $10^{-9}$ or one billionth of a meter and below. Generally, nanoparticles have a diameter in the range from about 1 nm to about 1000 nm. The term "nanoparticle" includes nanospheres; nanorods; nanoshells; and nanoprisms; and these nanoparticles can be part of a nanonetwork.

It will be understood by one of ordinary skill in the art that particles usually exhibit a distribution of particle sizes around the indicated "size." Unless otherwise stated, the term "size" as used herein refers to the mode of a size distribution of microparticles, i.e., the value that occurs most frequently in the size distribution. Accordingly, the particles can be, e.g., monodisperse or polydisperse and the variation in size of the particles of a given dispersion can vary.

Methods for measuring the microparticle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the microbe-targeting substrate is a magnetic substrate. As used herein, the term "magnetic substrate" can refer to a solid substrate that is attracted or repelled by a magnetic field gradient or has a non-zero magnetic susceptibility. The magnetic substrate can be ferromagnetic, paramagnetic or super-paramagnetic. In some embodiments, magnetic substrate can be super-paramagnetic. In some embodiments, magnetic substrate can have a polymer shell for protecting the microbe-targeting molecule from exposure to iron provided that the polymer shell has no adverse effect on the magnetic property.

Using a magnetic substrate can be advantageous because the microbe-bound magnetic substrate can be easily separated from a sample fluid using a magnetic field, be examined for the presence of the microbe, and/or be used to transfer the collected microbes to conventional microbe culture (e.g., pathogen culture), analysis, identification or sensitivity testing assays.

In some embodiments, the magnetic substrate is a magnetic bead. Without limitations, the magnetic beads can range in size from 1 nm to 1 mm, i.e., a magnetic bead can be or nanometer or micrometer scale. For example, magnetic beads can be about 1 nm to about 500 µm, about 10 nm to about 250 µm, about 20 nm to about 100 µm, about 50 nm to about 250 µm in size. In some embodiments, magnetic beads can be about 0.05 µm to about 100 µm in size. In some embodiments, magnetic beads can be about 0.05 µm to about 10 µm in size. In some embodiments, magnetic beads can be about 0.05 µm to about 5 µm in size. In some embodiments, magnetic beads can be about 0.08 µm to about 1 µm in size. In one embodiment, the magnetic beads can be about 25 nm to about 250 nm, or about 90 nm to about 200 nm in size. In one embodiment, the magnetic beads can be about 0.1 µm to about 10 µm or about 0.5 µm to about 5 µm.

In some embodiments, the magnetic bead is a magnetic nanoparticle or magnetic microparticle. Magnetic nanoparticles and microparticles are a class of particle which can be manipulated using magnetic field or magnetic field gradient. Such particles commonly consist of magnetic elements such as iron, nickel and cobalt and their oxide compounds. Magnetic nanoparticles and microparticles are well-known and methods for their preparation have been described in the art. See, e.g., U.S. Pat. No. 6,878,445; No. 5,543,158; No. 5,578,325; No. 6,676,729; No. 6,045,925; and No. 7,462,446; and U.S. Patent Publications No. 2005/0025971; No. 2005/0200438; No. 2005/0201941; No. 2005/0271745; No. 2006/0228551; No. 2006/0233712; No. 2007/01666232; and No. 2007/0264199.

Magnetic beads are also widely and commercially available, with or without functional groups capable of binding to coupling molecules. Magnetic beads functionalized with various functional groups, e.g., amino groups, carboxylic acid groups, epoxy groups, tosyl groups, or silica-like groups, are also widely and commercially available. Suitable magnetic beads are commercially available such as from PerSeptive Diagnostics, Inc. (Cambridge, Mass.); Invitrogen Corp. (Carlsbad, Calif.); Cortex Biochem Inc. (San Leandro, Calif.); and Bangs Laboratories (Fishers, Ind.). In particular embodiments, magnetic particles that can be used herein can be any DYNABEADS® magnetic microbeads (Invitrogen Inc.), depending on the substrate surface chemistry.

In some embodiments, the microbe-targeting substrate is a microbe-targeting magnetic particle or bead coated with at least one microbe-targeting molecule. Microbe-targeting particles and microbe-targeting magnetic beads are also described in the International Application Publication Nos. WO/2011/090954 and WO/2013/012924, contents of both of which are incorporated herein by reference.

Microbe-Targeting Molecules or Microbe-Binding Molecules

The terms "microbe-targeting molecules" and "microbe-binding molecules" are used interchangeably herein. Any molecule or material that can bind to a microbe can be employed as the microbe-binding molecule (or microbe-targeting molecules). Exemplary microbe-binding molecules (or microbe-targeting molecules) include, but are not limited to, opsonins, lectins, antibodies and antigen binding fragments thereof, proteins, peptides, nucleic acids, carbohydrates, lipids, and any combinations thereof. The microbe-targeting molecule can comprise at least one (e.g., one, two, three, four, five, six, seven, eight, nine, ten, eleven, twelve, thirteen, fourteen, fifteen, sixteen, seventeen, eighteen, nineteen, twenty or more) microbe surface-binding domain ("microbe binding domain"). The term "microbe surface-binding domain" as used herein refers to any molecules or a fragment thereof that can specifically bind to the surface of a microbe, e.g., any component present on a surface of a microbe.

Materials or substances which can serve as microbe-binding molecules include, for example, peptides, polypeptides, proteins, peptidomimetics, antibodies, antibody fragments (e.g., antigen binding fragments of antibodies), carbohydrate-binding protein, e.g., a lectin, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptidoglycan, lipopolysaccharide, small molecules, and any combinations thereof. The microbe-binding molecule can be covalently (e.g., cross-linked) or non-covalently linked to the substrate surface.

In some embodiments, the microbe surface-binding domain can comprise an opsonin or a fragment thereof. The term "opsonin" as used herein refers to naturally-occurring and synthetic molecules which are capable of binding to or attaching to the surface of a microbe or a pathogen, of acting as binding enhancers for a process of phagocytosis. Examples of opsonins which can be used in the engineered molecules described herein include, but are not limited to, vitronectin, fibronectin, complement components such as C1q (including any of its component polypeptide chains A, B and C), complement fragments such as C3d, C3b and C4b, mannose-binding protein, conglutinin, surfactant proteins A and D, C-reactive protein (CRP), alpha2-macroglobulin, and immunoglobulins, for example, the Fc portion of an immunoglobulin.

In some embodiments, the microbe surface-binding domain comprises a carbohydrate recognition domain or a carbohydrate recognition portion thereof. As used herein, the term "carbohydrate recognition domain" refers to a region, at least a portion of which, can bind to carbohydrates on a surface of a microbe (e.g., a pathogen).

In some embodiments, the microbe surface-binding domain comprises a lectin or a carbohydrate recognition or binding fragment or portion thereof. The term "lectin" as used herein refers to any molecules including proteins, natural or genetically modified, that interact specifically with saccharides (i.e., carbohydrates). The term "lectin" as used herein can also refer to lectins derived from any species, including, but not limited to, plants, animals, insects and microorganisms, having a desired carbohydrate binding specificity. Examples of plant lectins include, but are not limited to, the Leguminosae lectin family, such as ConA, soybean agglutinin, peanut lectin, lentil lectin, and Galanthus nivalis agglutinin (GNA) from the Galanthus (snowdrop) plant. Other examples of plant lectins are the Gramineae and Solanaceae families of lectins. Examples of animal lectins include, but are not limited to, any known lectin of the major groups S-type lectins, C-type lectins, P-type lectins, and I-type lectins, and galectins. In some embodiments, the carbohydrate recognition domain can be derived from a C-type lectin, or a fragment thereof. C-type lectin can include any carbohydrate-binding protein that requires calcium for binding. In some embodiments, the C-type lectin can include, but is not limited to, collectin, DC-SIGN, and fragments thereof. Without wishing to be bound by theory, DC-SIGN can generally bind various microbes by recognizing high-mannose-containing glycoproteins on their envelopes and/or function as a receptor for several viruses such as HIV and Hepatitis C.

In some embodiments, the microbe-targeting molecules or microbe-binding molecules can comprise a microbe-binding portion of the C-type lectins, including, e.g., but not limited to, soluble factors such as Collectins (e.g., MBL, surfactant protein A, surfactant protein D and Collectin 11), ficolins (e.g. L-Ficolin, Ficolin A), receptor based lectins (e.g DC-SIGN, DC-SIGNR, SIGNR1, Macrophage Mannose Receptor 1, Dectin-1 and Dectin-2), lectins from the shrimp Marsupenaeus japonicus (e.g. Lectin A, Lectin B and Lectin C), or any comginations thereof.

In some embodiments, the microbe-targeting molecules or microbe-binding moelcules can comprise at least a portion of non-C-type lectins (e.g., but not limited to, Wheat Germ Agglutinin).

In some embodiments, the microbe-targeting molecules or microbe-binding moelcules can comprise at least a portion of lipopolysaccharide (LPS)-binding proteins and/or endotoxin binding proteins (e.g., but not limited to, CD14, MD2, lipopolysaccharide binding proteins (LBP), *limulus* anti-LPS factor (LAL-F), or any combinations thereof).

In some embodiments, the microbe-targeting molecules or microbe-binding moelcules can comprise at least a portion of peptidoglycan binding proteins (e.g., but not limited to, mammalian peptidoglycan recognition protein-1 (PGRP-1), PGRP-2, PGRP-3, PGRP-4, or any combinations thereof.

Collectins are soluble pattern recognition receptors (PRRs) belonging to the superfamily of collagen containing C-type lectins. Exemplary collectins include, without limitations, mannan-binding lectin (MBL) or mannose-binding protein, surfactant protein A (SP-A), surfactant protein D (SP-D), collectin liver 1 (CL-L1), collectin placenta 1 (CL-P1), conglutinin, collectin of 43 kDa (CL-43), collectin of 46 kDa (CL-46), and a fragment thereof.

In some embodiments, the microbe-surface binding domain comprises the full amino acid sequence of a carbohydrate-binding protein.

In some embodiments, the microbe surface-binding molecule comprises a mannose-binding lectin (MBL) or a carbohydrate binding fragment or portion thereof. Mannose-binding lectin, also called mannose binding protein (MBP), is a calcium-dependent serum protein that can play a role in the innate immune response by binding to carbohydrates on the surface of a wide range of microbes or pathogens (viruses, bacteria, fungi, protozoa) where it can activate the complement system. MBL can also serve as a direct opsonin and mediate binding and uptake of microbes or pathogens by tagging the surface of a microbe or pathogen to facilitate recognition and ingestion by phagocytes. MBL and an engineered form of MBL (FcMBL and Akt-FcMBL) are described in the International Application Publication Nos. WO/2011/090954 and WO/2013/012924, contents of both of which are incorporated herein by reference.

Without wishing to be bound by a theory, microbe binding molecules comprising lectins or modified versions thereof can act as broad-spectrum microbe binding molecules (e.g., pathogen binding molecules). Accordingly, antibiotic susceptibility method utilizing lectins (e.g., MBL and genetically engineered version of MBL (FcMBL and Akt-Fc-MBL)) as broad-spectrum microbe binding molecules (e.g., pathogen binding molecules) to capture and grow the microbes, can be carried out without identifying the microbe (e.g., pathogen), either for extraction or for antibiotic sensitivity testing.

In some embodiments, at least two microbe surface-binding domains (e.g. two, three, four, five, six, seven or more) microbe surface-binding domains, can be linked together to form a multimeric microbe surface-binding domain. In such embodiments, the distances between microbe surface-binding domains can be engineered to match with the distance between the binding sites on the target microbe surface.

A multimeric microbe surface-binding domain can have each of the individual microbe surface-binding domains be identical. Alternatively, a multimeric microbe surface-binding domain can have at least one, at least two, or at least three microbe surface-binding domains different from the rest. In such embodiments, microbe surface-binding domains that share a common binding specificity for molecule on a microbe surface can be used. By way of example only, the fibrinogen-like domain of several lectins has a similar function to the CRD of C-type lectins including MBL, and function as pattern-recognition receptors to discriminate microbes or pathogens from self. One of such lectins comprising the fibrinogen-like domain is serum ficolins.

Serum ficolins have a common binding specificity for GlcNAc (N-acetyl-glucosamine), elastin or GalNAc (N-acetyl-galactosamine). The fibrinogen-like domain is responsible for the carbohydrate binding. In human serum, two types of ficolin, known as L-ficolin (also called P35, ficolin L, ficolin 2 or hucolin) and H-ficolin (also called Hakata antigen, ficolin 3 or thermolabile b2-macroglycoprotein), have been identified, and both of them have lectin activity. L-ficolin recognizes GlcNAc and H-ficolin recognizes GalNAc. Another ficolin known as M-ficolin (also called P3 5-related protein, ficolin 1 or ficolin A) is not considered to be a serum protein and is found in leucocytes and in the lungs. L-ficolin and H-ficolin activate the lectin-complement pathway in association with MASPs. M-Ficolin, L-ficolin and H-ficolin have calcium-independent lectin activity. Accordingly, in some embodiments, a microbe-targeting molecule can comprise MBL and L-ficolin carbohydrate recognition domains, MBL and H-ficolin carbohydrate recognition domains, or a combination thereof.

Any art-recognized recombinant carbohydrate-binding proteins or carbohydrate recognition domains can also be used in the microbe-targeting molecules. For example, recombinant mannose-binding lectins, e.g., but not limited to, the ones disclosed in the U.S. Pat. Nos. 5,270,199; 6,846,649; and U.S. Patent Application No. US 2004/0,229, 212, content of both of which is incorporated herein by reference, can be used in constructing a microbe-targeting molecule.

The microbe binding molecule can further comprise at least one (e.g., one, two, three, four, five, six, seven, eight, nine, ten, eleven, twelve, thirteen, fourteen, fifteen, sixteen, seventeen, eighteen, nineteen, twenty or more) substrate surface binding domain ("substrate binding domain") adapted for orienting the microbe binding domain away from the substrate surface. As used herein, the term "substrate-binding domain" refers to any molecule that facilitates the conjugation of the engineered molecules described herein to a substrate or a functionalized substrate. The microbe binding domain and the substrate binding domains can be linked by a linker. Similarly, the substrate binding domain and the substrate surface can be linked by a linker.

The substrate-binding domain can comprise at least one amino group that can non-covalently or covalently couple with functional groups on the surface of the substrate. For example, the primary amines of the amino acid residues (e.g., lysine or cysteine residues) at the N-terminus or in close proximity to the N-terminus of the microbe surface-binding domains can be used to couple with functional groups on the substrate surface.

In some embodiments, the substrate-binding domain can comprise at least one, at least two, at least three or more oligopeptides. The length of the oligonucleotide can vary from about 2 amino acid residues to about 10 amino acid residues, or about 2 amino acid residues to about 5 amino acid residues. Determination of an appropriate amino acid sequence of the oligonucleotide for binding with different substrates is well within one of skill in the art. For example, an oligopeptide comprising an amino acid sequence of AKT, which provides a single biotinylation site for subsequent binding to streptavidin-coated substrate. Such single biotinylation site can also enable the microbe surface binding domain of a microbe binding molecule to orient away from the substrate, and thus become more accessible to microbes or pathogens. See, for example, Witus et al. (2010) JACS 132: 16812.

In some embodiments, the substrate-binding domain can comprise at least one oligonucleotide. The sequence and length of the oligonucleotides can be configured according to the types of the substrate, binding density, and/or desired binding strength. For example, if the substrate is a nucleic acid scaffold, e.g., a DNA scaffold, the oligonucleotide sequence of the substrate-binding domain can be designed such that it is complementary to a sub-sequence of the nucleic acid scaffold to where the substrate-binding domain can hybridize.

In some embodiments, the oligonucleotides can include aptamers. As used herein, the term "aptamer" means a single-stranded, partially single-stranded, partially double-stranded or double-stranded nucleotide sequence capable of specifically recognizing a selected non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Methods for selecting aptamers for binding to a molecule are widely known in the art and easily accessible to one of ordinary skill in the art. The oligonucleotides including aptamers can be of any length, e.g., from about 1 nucleotide to about 100 nucleotides, from about 5 nucleotides to about 50 nucleotides, or from about 10 nucleotides to about 25 nucleotides. Generally, a longer oligonucleotide for hybridization to a nucleic acid scaffold can generate a stronger binding strength between the engineered microbe surface-binding domain and substrate.

The microbe-targeting molecules can contain sequences from the same species or from different species. For example, an interspecies hybrid microbe-targeting molecule can contain a linker, e.g., a peptide linker, from a murine species, and a human sequence from a carbohydrate recognition domain protein, provided that they do not provide unacceptable levels of deleterious effects. The engineered microbe-targeting molecules described herein can also include those that are made entirely from murine-derived sequences or fully human.

General methods of preparing such microbe-targeting molecules are well known in the art (Ashkenazi, A. and S. M. Chamow (1997), "Immunoadhesins as research tools and therapeutic agents," Curr. Opin. Immunol. 9(2): 195-200, Chamow, S. M. and A. Ashkenazi (1996). "Immunoadhesins: principles and applications," Trends Biotechnol. 14(2):52-60). In one example, an engineered microbe-targeting molecule can be made by cloning into an expression vector such as Fc-X vector as discussed in Lo et al. (1998) 11:495 and PCT application no. PCT/US2011/021603, filed Jan. 19, 2011, content of both of which is incorporated herein by reference.

In one embodiment, the microbe-targeting molecule comprises an MBL, a carbohydrate recognition domain of an MBL, or a genetically engineered version of MBL (FcMBL) as described in the International Application Publication Nos. WO/2011/090954 and WO/2013/012924, contents of both of which are incorporated herein by reference. Amino acid sequences for MBL and engineered MBL are:

```
(i) MBL full length (SEQ ID NO. 1):
MSLFPSLPLL LLSMVAASYS ETVTCEDAQK TCPAVIACSS PGINGFPGKD
GRDGTKGEKG EPGQGLRGLQ GPPGKLGPPG NPGPSGSPGP KGQKGDPGKS
PDGDSSLAAS ERKALQTEMA RIKKWLTFSL GKQVGNKFFL TNGEIMTFEK
VKALCVKFQA SVATPRNAAE NGAIQNLIKE EAFLGITDEK TEGQFVDLTG
NRLTYTNWNE GEPNNAGSDE DCVLLLKNGQ WNDVPCSTSH LAVCEFPI (ii) MBL without the signal sequence (SEQ ID NO. 2):
ETVTCEDAQK TCPAVIACSS PGINGFPGKD GRDGTKGEKG EPGQGLRGLQ
GPPGKLGPPG NPGPSGSPGP KGQKGDPGKS PDGDSSLAAS ERKALQTEMA
RIKKWLTFSL GKQVGNKFFL TNGEIMTFEK VKALCVKFQA SVATPRNAAE
NGAIQNLIKE EAFLGITDEK TEGQFVDLTG NRLTYTNWNE GEPNNAGSDE
DCVLLLKNGQ WNDVPCSTSH LAVCEFPI (iii) Truncated MBL (SEQ ID NO. 3):
AASERKALQT EMARIKKWLT FSLGKQVGNK FFLTNGEIMT FEKVKALCVK
FQASVATPRN AAENGAIQNL IKEEAFLGIT DEKTEGQFVD LTGNRLTYTN
WNEGEPNNAG SDEDCVLLLK NGQWNDVPCS TSHLAVCEFP I (iv) Carbohydrate recognition domain (CRD) of MBL (SEQ ID NO. 4):
VGNKFFLTNG EIMTFEKVKA LCVKFQASVA TPRNAAENGA
IQNLIKEEAF LGITDEKTEG QFVDLTGNRL TYTNWNEGEP
NNAGSDEDCV LLLKNGQWND VPCSTSHLAV CEFPI (v) Neck + Carbohydrate recognition domain of MBL (SEQ ID NO. 45):
PDGDSSLAAS ERKALQTEMA RIKKWLTFSL GKQVGNKFFL
TNGEIMTFEK VKALCVKFQA SVATPRNAAE NGAIQNLIKE
EAFLGITDEK TEGQFVDLTG NRLTYTNWNE GEPNNAGSDE
DCVLLLKNGQ WNDVPCSTSH LAVCEFPI (vi) FcMBL.81 (SEQ ID NO. 6):
EPKSSDKTHT CPPCPAPELL GGPSVFLFPP KPKDTLMISR TPEVTCVVVD VSHEDPEVKF
NWYVDGVEVH NAKTKPREEQ YNSTYRVVSV LTVLHQDWLN GKEYKCKVSN KALPAPIEKT
ISKAKGQPRE PQVYTLPPSR DELTKNQVSL TCLVKGFYPS DIAVEWESNG QPENNYKTTP
PVLDSDGSFF LYSKLTVDKS RWQQGNVFSC SVMHEALHNH YTQKSLSLSP GAPDGDSSLA
ASERKALQTE FLTNGEIMTF EKVKALCVKF QASVATPRNA AENGAIQNLI MARIKKWLTF
SLGKQVGNKF KEEAFLGITD EKTEGQFVDL TGNRLTYTNW NEGEPNNAGS DEDCVLLLKN
GQWNDVPCST SHLAVCEFPI (vii) Akt-FcMBL (SEQ ID NO. 7):
AKTEPKSSDKTHT CPPCPAPELL GGPSVFLFPP KPKDTLMISR TPEVTCVVVD VSHEDPEVKF
NWYVDGVEVH NAKTKPREEQ YNSTYRVVSV LTVLHQDWLN GKEYKCKVSN KALPAPIEKT
ISKAKGQPRE PQVYTLPPSR DELTKNQVSL TCLVKGFYPS DIAVEWESNG QPENNYKTTP
PVLDSDGSFF LYSKLTVDKS RWQQGNVFSC SVMHEALHNH YTQKSLSLSP GAPDGDSSLA
ASERKALQTE MARIKKWLTF SLGKQVGNKF FLTNGEIMTF EKVKALCVKF QASVATPRNA
AENGAIQNLI KEEAFLGITD EKTEGQFVDL TGNRLTYTNW NEGEPNNAGS DEDCVLLLKN
GQWNDVPCST SHLAVCEFPI (viii) FcMBL.111 (SEQ ID NO. 8):
EPKSSDKTHT CPPCPAPELL GGPSVFLFPP KPKDTLMISR TPEVTCVVVD VSHEDPEVKF
NWYVDGVEVH NAKTKPREEQ YNSTYRVVSV LTVLHQDWLN GKEYKCKVSN KALPAPIEKT
ISKAKGQPRE PQVYTLPPSR DELTKNQVSL TCLVKGFYPS DIAVEWESNG QPENNYKTTP
PVLDSDGSFF LYSKLTVDKS RWQQGNVFSC SVMHEALHNH YTQKSLSLSP GATSKQVGNKF
FLTNGEIMTF EKVKALCVKF QASVATPRNA AENGAIQNLI KEEAFLGITD EKTEGQFVDL
TGNRLTYTNW NEGEPNNAGS DEDCVLLLKN GQWNDVPCST SHLAVCEFPI
```

In some embodiments, microbe-targeting molecule comprises an amino acid sequence selected from SEQ ID NO. 1-SEQ ID NO. 8

Linkers

As used herein, the term "linker" generally refers to a molecular entity that can directly or indirectly connect two parts of a composition, e.g., at least one microbe-binding molecule and at least one substrate-binding domain or at least one enzyme and at least one microbe-binding molecule. In some embodiments, the linker can directly or indirectly connect to one or more microbe-binding molecule or microbe-binding domain.

Linkers can be configures according to a specific need, e.g., based on at least one of the following characteristics. By way of example only, in some embodiments, linkers can be configured to have a sufficient length and flexibility such that it can allow for a microbe surface-binding domain to orient accordingly with respect to at least one carbohydrate on a microbe surface. In some embodiments, linkers can be configured to allow multimerization of at least two engineered microbe-targeting molecules (e.g., to from a di-, tri-, tetra-, penta-, or higher multimeric complex) while retaining biological activity (e.g., microbe-binding activity). In some embodiments, linkers can be configured to facilitate expression and purification of the engineered microbe-targeting molecule described herein. In some embodiments, linkers can be configured to provide at least one recognition-site for proteases or nucleases. In addition, linkers should be non-reactive with the functional components of the engineered molecule described herein (e.g., minimal hydrophobic or charged character to react with the functional protein domains such as a microbe surface-binding domain or a substrate-binding domain).

In some embodiments, a linker can be configured to have any length in a form of a peptide, a protein, a nucleic acid (e.g., DNA or RNA), or any combinations thereof. In some embodiments, the peptide or nucleic acid linker can vary from about 1 to about 1000 amino acids long, from about 10 to about 500 amino acids long, from about 30 to about 300 amino acids long, or from about 50 to about 150 amino acids long. Longer or shorter linker sequences can be also used for the engineered microbe-targeting molecules described herein. In one embodiment, the peptide linker has an amino acid sequence of about 200 to 300 amino acids in length.

In some embodiments, a peptide or nucleic acid linker can be configured to have a sequence comprising at least one of the amino acids selected from the group consisting of glycine (Gly), serine (Ser), asparagine (Asn), threonine (Thr), methionine (Met) or alanine (Ala), or at least one of codon sequences encoding the aforementioned amino acids (i.e., Gly, Ser, Asn, Thr, Met or Ala). Such amino acids and corresponding nucleic acid sequences are generally used to provide flexibility of a linker. However, in some embodiments, other uncharged polar amino acids (e.g., Gln, Cys or Tyr), nonpolar amino acids (e.g., Val, Leu, Ile, Pro, Phe, and Trp), or nucleic acid sequences encoding the amino acids thereof can also be included in a linker sequence. In alternative embodiments, polar amino acids or nucleic acid sequence thereof can be added to modulate the flexibility of a linker. One of skill in the art can control flexibility of a linker by varying the types and numbers of residues in the linker. See, e.g., Perham, 30 Biochem. 8501 (1991); Wriggers et al., 80 Biopolymers 736 (2005).

In alternative embodiments, a linker can be a chemical linker of any length. In some embodiments, chemical linkers can comprise a direct bond or an atom such as oxygen or sulfur, a unit such as NH, C(O), C(O)NH, SO, $SO_2$, $SO_2NH$, or a chain of atoms, such as substituted or unsubstituted C1-C6 alkyl, substituted or unsubstituted C2-C6 alkenyl, substituted or unsubstituted C2-C6 alkynyl, substituted or unsubstituted C6-C12 aryl, substituted or unsubstituted C5-C12 heteroaryl, substituted or unsubstituted C5-C12 heterocyclyl, substituted or unsubstituted C3-C12 cycloalkyl, where one or more methylenes can be interrupted or terminated by O, S, S(O), $SO_2$, NH, or C(O). In some embodiments, the chemical linker can be a polymer chain (branched or linear).

In some embodiments where the linker is a peptide, such peptide linker can comprise at least a portion of an immunoglobulin, e.g., IgA, IgD, IgE, IgG and IgM including their subclasses (e.g., IgG1), or a modified thereof. In some embodiments, the peptide linker can comprise a portion of fragment crystallization (Fc) region of an immunoglobulin or a modified thereof. In such embodiments, the portion of the Fc region that can be used as a linker can comprise at least one region selected from the group consisting of a hinge region, a CH2 region, a CH3 region, and any combinations thereof. By way of example, in some embodiments, a CH2 region can be excluded from the portion of the Fc region as a linker. In one embodiment, Fc linker comprises a hinge region, a CH2 domain and a CH3 domain. Such Fc linker can be used to facilitate expression and purification of the engineered microbe-targeting molecules described herein. The N terminal Fc has been shown to improve expression levels, protein folding and secretion of the fusion partner. In addition, the Fc has a staphylococcal protein A binding site, which can be used for one-step purification protein A affinity chromatography. See Lo K M et al. (1998) Protein Eng. 11: 495-500. Further, such Fc linker have a molecule weight above a renal threshold of about 45 kDa, thus reducing the possibility of engineered microbe-targeting molecules being removed by glomerular filtration. Additionally, the Fc linker can allow dimerization of two engineered microbe-targeting molecules to form a dimer, e.g., a dimeric MBL molecule.

In various embodiments, the N-terminus or the C-terminus of the linker, e.g., the portion of the Fc region, can be modified. By way of example only, the N-terminus or the C-terminus of the linker can be extended by at least one additional linker described herein, e.g., to provide further flexibility, or to attach additional molecules. In some embodiments, the N-terminus of the linker can be linked directly or indirectly (via an additional linker) with a substrate-binding domain adapted for orienting the carbohydrate recognition domain away from the substrate. Exemplary Fc linked MBL (FcMBL and Akt-FcMBL) are described in PCT application no. PCT/US2011/021603, filed Jan. 19, 2011, content of which is incorporated herein by reference.

In some embodiments, the linker can be embodied as part of the microbe surface-binding domain, or part of the microbe surface-binding domain.

In some embodiments, the distance between the microbe surface-binding domain and the substrate surface can range from about 50 angstroms to about 5000 angstroms, from about 100 angstroms to about 2500 angstroms, or from about 200 angstroms to about 1000 angstroms.

In some embodiments, the linkers can be branched. For branched linkers, the linker can linked together at least one (e.g., one, two, three, four, five, six, seven, eight, nine, ten or more) surface binding domain and at least one (e.g., one, two, three, four, five, six, seven, eight, nine, ten or more) microbe surface-binding domain.

In some embodiments provided herein, the linker can further comprise a detectable label. In some embodiments, the detectable label can be a chromogenic or fluorogenic microbe enzyme substrate so that when a microbe binds to the engineered microbe-targeting molecule, the enzyme that the microbe releases can interact with the detectable label to induce a color change. Examples of such microbe enzyme substrate can include, but are not limited to, indoxyl butyrate, indoxyl glucoside, esculin, magneta glucoside, red-β-glucuronide, 2-methoxy-4-(2-nitrovinyl) phenyl β-D-glu-copyranoside, 2-methoxy-4-(2-nitrovinyl) phenyl β-D-cetamindo-2-deoxyglucopyranoside, and any other art-recognized microbe enzyme substrates. Such embodiments can act as an indicator for the presence of a microbe or pathogen.

Conjugation of Microbe-Binding Molecules (or Microbe-Targeting Molecules) to a Substrate The microbe-targeting molecules can be immobilized on any substrate for use in the method described herein.

For microbe-targeting molecules immobilized on a solid substrate, the microbe-binding molecule can further comprise a substrate-binding domain, e.g., adapted for orienting the microbe surface-binding domain away from the substrate. Without limitations, exemplary types of substrates can be a nucleic acid scaffold, a biological molecule (e.g., a living cell), or a solid surface. In some embodiments, the solid surface can be functionalized with a coupling molecule, e.g., an amino group, to facilitate the conjugation of engineered microbe surface-binding domains to the solid surface.

The surface of a substrate can be functionalized to include a coupling molecule. As used herein, the term "coupling molecule" refers to any molecule or any functional group that is capable of selectively binding with a microbe surface-binding domain. Representative examples of coupling molecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule, such as biotin and avidin. The coupling molecules need not comprise an entire naturally occurring molecule but may consist of only a portion, fragment or subunit of a naturally or non-naturally occurring molecule, as for example the Fab fragment of an antibody. The coupling molecule can further comprise a detectable label. The coupling molecule can also encompass various functional groups that can couple the substrate to the engineered microbe surface-binding domains. Examples of such functional groups include, but are not limited to, an amino group, a carboxylic acid group, an epoxy group, and a tosyl group.

The coupling molecule can be conjugated to the surface of a solid substrate covalently or non-covalently using any of the methods known to those of skill in the art. For example, covalent immobilization can be accomplished through, for example, silane coupling. See, e.g., Weetall, 15 Adv. Mol. Cell. Bio. 161 (2008); Weetall, 44 Meths. Enzymol. 134 (1976). The covalent interaction between the coupling molecule and the surface can also be mediated by other art-recognized chemical reactions, such as NHS reaction. The non-covalent interaction between the coupling molecule and the surface can be formed based on ionic interactions, van der Waals interactions, dipole-dipole interactions, hydrogen bonds, electrostatic interactions, and/or shape recognition interactions.

In alternative embodiments, the engineered microbe surface-binding domains can be conjugated with the surface of the solid substrate by a coupling molecule pair. The term "coupling molecule pair" as used herein refers to the first and second molecules that specifically bind to each other. One member of the binding pair is conjugated with the solid substrate while the second member is conjugated with the substrate-binding domain of an engineered microbe surface-binding domain. As used herein, the phrase "first and second molecules that specifically bind to each other" refers to binding of the first member of the coupling pair to the second member of the coupling pair with greater affinity and specificity than to other molecules. Exemplary coupling molecule pairs include, without limitations, any haptenic or antigenic compound in combination with a corresponding antibody or binding portion or fragment thereof (e.g., digoxigenin and anti-digoxigenin; mouse immunoglobulin and goat antimouse immunoglobulin) and nonimmunological binding pairs (e.g., biotin-avidin, biotin-streptavidin), hormone (e.g., thyroxine and cortisol-hormone binding protein), receptor-receptor agonist, receptor-receptor antagonist (e.g., acetylcholine receptor-acetylcholine or an analog thereof), IgG-protein A, lectin-carbohydrate, enzyme-enzyme cofactor, enzyme-enzyme inhibitor, and complementary oligonucleotide pairs capable of forming nucleic acid duplexes). The coupling molecule pair can also include a first molecule that is negatively charged and a second molecule that is positively charged.

One non-limiting example of using conjugation with a coupling molecule pair is the biotin-sandwich method. See, e.g., Davis et al., 103 PNAS 8155 (2006). The two molecules to be conjugated together are biotinylated and then conjugated together using tetravalent streptavidin. In addition, a peptide can be coupled to the 15-amino acid sequence of an acceptor peptide for biotinylation (referred to as AP; Chen et al., 2 Nat. Methods 99 (2005)). The acceptor peptide sequence allows site-specific biotinylation by the E. Coli enzyme biotin ligase (BirA; Id.). An engineered microbe surface-binding domain can be similarly biotinylated for conjugation with a solid substrate. Many commercial kits are also available for biotinylating proteins. Another example for conjugation to a solid surface would be to use PLP—mediated bioconjugation. See, e.g., Witus et al., 132 JACS 16812 (2010). As described earlier, an AKT sequence on the N terminal of the engineered microbe-targeting molecule (e.g., N terminal of the linker between the substrate binding domain and the carbohydrate-binding molecule such as Fc region as described earlier) can allow the substrate binding domain to be biotinylated at a single site and further conjugated to the streptavidin-coated solid surface.

When the affinity of a single microbe-binding domain for a target molecule is relatively low, and such binding is generally driven by avidity and multivalency, multivalency of such engineered microbe-targeting molecules can be effectively increased by attachment of a plurality of microbe-targeting molecules to the solid substrate at a high density, which can be varied to provide optimal functionality. Alternatively, the microbe-targeting molecules can be immobilized on a solid substrate for easy handling during usage, e.g., for isolation, observation or microscopic imaging.

Kit

A kit for determining antibiotic susceptibility of a microbe (e.g., a pathogen) is also provided herein. In some embodiments, the kit comprises: (a) one or more containers containing a solid substrate coated with a plurality of microbe-targeting molecules; (b) an antibiotic agent; and (c) optionally a reagent.

In some embodiments, the kit further comprises at least one reagent for assaying microbial cell viability.

In some embodiments, the kit comprises one or more second containers each containing at least one antibiotic agent. Each such container can contain an antibiotic agent that is different from the others in the kit.

In some embodiments, the kit comprises at least microtiter plate comprising at least one antibiotic agent in at least one well. Without limitations, some wells of the microtiter plate can comprise a distinct antibiotic agents and some wells do not comprise any antibiotic agents, i.e., for use as a control or reference.

In some embodiments, the kit comprises at least one wafer containing one or more antibiotic agents. For example, the wafer containing at least one antibiotic can be placed onto a culture plate (e.g., an agar plate) upon which microbes, e.g., microbes isolated from a biological fluid using the engineered microbe-targeting molecules as described herein, are able to grow. If the microbes are sensitive to certain antibiotics, a clear ring, or zone of inhibition, will be seen around the wafer indicating poor microbial growth. Thus, some embodiments of the kit provided herein can be used for various antibiotic sensitivity testing—an assay to determine the susceptibility of microbes to one or more antibiotics.

In some embodiments, the kit comprises: (a) one or more first containers each containing a population of magnetic microbeads coated with a plurality of engineered microbe-targeting molecules; (b) one or more second containers each containing an antibiotic agent; and (c) at least one polypeptide conjugated with a detectable label.

The polypeptide conjugated to a detectable is configured for binding to the microbes or pathogens of interest. For example, in some embodiments, the polypeptide conjugated to a detectable label can comprise the same carbohydrate recognition domains as used in the microbe-targeting magnetic microbeads. In such embodiments, at least one population of the polypeptide-detectable label conjugate can comprise a carbohydrate recognition domain derived from mannose-binding lectin. Such population of the polypeptide-detectable label conjugate can further comprise a Fc region of an immunoglobulin. In alternative embodiments, the polypeptide conjugated to a detectable label can comprise an antibody that binds to microbes or pathogens. The antibody can be specific to each type of the microbes or pathogens recognized by the microbe-targeting magnetic microbes, or the antibody can be specific to each types of carbohydrate recognition domains employed in the microbe-targeting magnetic microbes. However, the antibody can also be a common antibody that binds to all the microbes or pathogens recognized by the microbe-targeting magnetic microbes.

In some embodiments, the kit comprises: (a) one or more first containers each containing a population of magnetic microbeads coated with a plurality of engineered microbe-targeting molecules; (b) one or more second containers each containing an antibiotic agent; and (c) at least one reagent for determining microbial cell viability by ELISA.

In some embodiment, the at least one reagent for determining microbial cell viability by ELISA is a polypeptide conjugated to a detectable label.

In some embodiments, the polypeptide conjugated to a detectable label is MBL or FcMBL conjugated with HRP, i.e. MBL-HRP or FcMBL-HRP.

In some embodiments, the kit comprises: (a) one or more first containers each containing a population of magnetic microbeads coated with a plurality of engineered microbe-targeting molecules; (b) at least one antibiotic agent; and (c) at least one reagent for determining microbial cell viability by measuring ATP levels or ROS levels.

In some embodiments, the at least one reagent for measuring ATP levels is a BACTITER-GLO™.

In some embodiments, the at least one reagent for measuring ROS levels is Luminol reviative L-012.

In some embodiments, at least one of the first containers contains a population of microbe-targeting magnetic microbeads distinct from other populations in the first containers, e.g., the distinct population of engineered microbe-targeting magnetic microbes can comprise a distinct carbohydrate recognition domain. Depending on the configuration of the protein-detectable label conjugates provided in the kit, different populations of the microbe-targeting magnetic microbeads can be mixed together to form a single mixture for use in a single reaction with a sample, or each different populations can be used separately in a different aliquot of the same sample. After contacting the sample with the microbe-targeting magnetic microbeads, any microbes or pathogens recognized by the microbe-targeting molecules will be bound to the magnetic microbeads.

In some embodiments, at least one of the second containers can contain a distinct population of the protein-detectable label conjugate. The distinct population of the protein-detectable label conjugate can contain a unique protein with the detectable label same as others, or a conjugate comprising a distinct detectable label (e.g., a unique fluorescent molecule) and a distinct protein. As each distinct detectable label can identify the associated protein, conjugates comprising a distinct detectable label associated with a distinct protein can allow detecting in a single sample at least two or more distinct populations of the engineered microbe-targeting magnetic microbeads, e.g., each distinct population comprising a unique carbohydrate recognition domain. In alternative embodiments, the protein-detectable label conjugates in the second containers can comprise the same detectable label. For example, the detectable label can comprise an enzyme (e.g., horseradish peroxidase) that produces a color change in the presence of an enzyme substrate.

In some embodiments, the kit can further comprise a wash buffer, a dilution buffer, a stop buffer (e.g., to stop the color development), a growth media, a substrate for an enzyme for ELISA, heparin, or any combinations thereof.

In some embodiments, the kit can further comprise at least one microtiter plate, e.g., for performing the reaction and the detection.

In some embodiments, the kit can further comprise one or more containers containing a matrix or gel matrix (in liquid or viscous liquid format or in powder format, including lyophilized powder), e.g., for immobilizing a microbe and/or for forming a detection substrate as described herein. Examples of matrix or gel matrix in liquid or powder format can include, but are not limited to, agarose, collagen, matrigel, alginate, biocompatible polymer (e.g., but not limited to, PLGA, PEG, and/or thermally-responsive polymer), hydrogel, gelatin, fibrin, and any combinations thereof.

In some embodiments, the kit can further comprise a detection agent for determining at least metabolism (or metabolic activity) or viability of a microbe as described herein. In some embodiments, the detection agent can be pre-mixed with the matrix or gel matrix included the kit. In other embodiments, the detection agent can be loaded in one or more containers.

In some embodiments, the kit can further comprise at least one solid support described herein for immobilizing a microbe, e.g., but not limited to, multi-well plates, slides (e.g., microscopic slides), cover slips, paper/strips, dipsticks, tubes, capillaries, microfluidic devices and any combinations thereof.

Exemplary Microbes or Pathogens

As used interchangeably herein, the terms "microbes" and "pathogens" generally refer to microorganisms, including bacteria, fungi, protozoan, archaea, protists, e.g., algae, and a combination thereof. The term "microbes" also includes pathogenic microbes, e.g., bacteria causing diseases such as plague, tuberculosis and anthrax; protozoa causing diseases such as malaria, sleeping sickness and toxoplasmosis; fungi causing diseases such as ringworm, candidiasis or histoplasmosis; and bacteria causing diseases such as sepsis. The term "microbe" or "microbes" can also encompass non-pathogenic microbes, e.g., some microbes used in industrial applications.

One skilled in the art can understand that the method described herein can be used to determine the antibiotic susceptibility of any microorganism.

In some other embodiments, the method described herein can be used to determine the antibiotic susceptibility of at least one of the following pathogens that causes diseases: *Bartonella henselae, Borrelia burgdorferi, Campylobacter jejuni, Campylobacterfetus, Chlamydia trachomatis, Chlamydia pneumoniae, Chylamydia psittaci, Simkania negevensis, Escherichia coli* (e.g., O157:H7 and K88), *Ehrlichia chafeensis, Clostridium botulinum, Clostridium perfringens, Clostridium tetani, Enterococcus faecalis, Haemophilus influenzae, Haemophilus ducreyi, Coccidioides immitis, Bordetella pertussis, Coxiella burnetii, Ureaplasma urealyticum, Mycoplasma genitalium, Trichomatis vaginalis, Helicobacter pylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacterium fortuitum, Mycobacterium genavense, Mycobacterium haemophilum, Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis, Treponema pallidum,* Human rhinovirus, Human coronavirus, Dengue virus, Filoviruses (e.g., Marburg and Ebola viruses), Hantavirus, Rift Valley virus, Hepatitis B, C, and E, Human Immunodeficiency Virus (e.g., HIV-1, HIV-2), HHV-8, Human papillomavirus, Herpes virus (e.g., HV-I and HV-II), Human T-cell lymphotrophic viruses (e.g., HTLV-I and HTLV-II), Bovine leukemia virus, Influenza virus, Guanarito virus, Lassa virus, Measles virus, Rubella virus, Mumps virus, Chickenpox (Varicella virus), Monkey pox, Epstein Bahr virus, Norwalk (and Norwalk-like) viruses, Rotavirus, Parvovirus B19, Hantaan virus, Sin Nombre virus, Venezuelan equine encephalitis, Sabia virus, West Nile virus, Yellow Fever virus, causative agents of transmissible spongiform encephalopathies, Creutzfeldt-Jakob disease agent, variant Creutzfeldt-Jakob disease agent, *Candida, Cryptcooccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi,* among other viruses, bacteria, archaea, protozoa, and fungi).

In some embodiments, the method described herein can be used to determine the antibiotic susceptibility of a bacteria present in a biofilm. For example, *Listeria monocytogenes* can form biofilms on a variety of materials used in food processing equipment and other food and non-food contact surfaces (Blackman, J Food Prot 1996; 59:827-31; Frank, J Food Prot 1990; 53:550-4; Krysinski, J Food Prot 1992; 55:246-51; Ronner, J Food Prot 1993; 56:750-8). Biofilms can be broadly defined as microbial cells attached to a surface, and which are embedded in a matrix of extracellular polymeric substances produced by the microorganisms. Biofilms are known to occur in many environments and frequently lead to a wide diversity of undesirable effects. For example, biofilms cause fouling of industrial equipment such as heat exchangers, pipelines, and ship hulls, resulting in reduced heat transfer, energy loss, increased fluid frictional resistance, and accelerated corrosion. Biofilm accumulation on teeth and gums, urinary and intestinal tracts, and implanted medical devices such as catheters and prostheses frequently lead to infections (Characklis W G. Biofilm processes. In: Characklis W G and Marshall K C eds. New York: John Wiley & Sons, 1990: 195-231; Costerton et al., Annu Rev Microbiol 1995; 49:711-45).

In some embodiments, the method described herein can be used to determine the antibiotic susceptibility of a plant pathogen. Plant fungi have caused major epidemics with huge societal impacts. Examples of plant fungi include, but are not limited to, *Phytophthora infestans, Crinipellis perniciosa,* frosty pod (*Moniliophthora roreri*), oomycete *Phytophthora capsici, Mycosphaerella fijiensis, Fusarium Ganoderma* spp fungi and *Phytophthora*. An exemplary plant bacterium includes *Burkholderia cepacia*. Exemplary plant viruses include, but are not limited to, soybean mosaic virus, bean pod mottle virus, tobacco ring spot virus, barley yellow dwarf virus, wheat spindle streak virus, soil born mosaic virus, wheat streak virus in maize, maize dwarf mosaic virus, maize chlorotic dwarf virus, cucumber mosaic virus, tobacco mosaic virus, alfalfa mosaic virus, potato virus X, potato virus Y, potato leaf roll virus and tomato golden mosaic virus.

In yet other embodiments, the method described herein can be used to determine the antibiotic susceptibility of bioterror agents (e.g., *B. Anthracis*, and smallpox).

Test Sample

In accordance with various embodiments described herein, a test sample, including any fluid or specimen (processed or unprocessed), that is suspected of comprising a pathogen can be subjected to an assay or method, kit and system described herein. The test sample or fluid can be liquid, supercritical fluid, solutions, suspensions, gases, gels, slurries, and combinations thereof. The test sample or fluid can be aqueous or non-aqueous.

In some embodiments, the test sample can be an aqueous fluid. As used herein, the term "aqueous fluid" refers to any flowable water-containing material that is suspected of comprising a pathogen.

In some embodiments, the test sample can include a biological fluid obtained from a subject. Exemplary biological fluids obtained from a subject can include, but are not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof. In some embodiments, a biological fluid can include a homogenate of a tissue specimen (e.g., biopsy) from a subject. In one embodiment, a test sample can comprises a suspension obtained from homogenization of a solid sample obtained from a solid organ or a fragment thereof.

In some embodiments, the test sample can include a fluid or specimen obtained from an environmental source, e.g., but not limited to, food products or industrial food products, food produce, poultry, meat, fish, beverages, dairy products, water supplies (including wastewater), surfaces, ponds, rivers, reservoirs, swimming pools, soils, food processing and/or packaging plants, agricultural places, hydrocultures (including hydroponic food farms), pharmaceutical manufacturing plants, animal colony facilities, and any combinations thereof.

In some embodiments, the test sample can include a fluid (e.g., culture medium) from a biological culture. Examples of a fluid (e.g., culture medium) obtained from a biological culture includes the one obtained from culturing or fermentation, for example, of single- or multi-cell organisms, including prokaryotes (e.g., bacteria) and eukaryotes (e.g., animal cells, plant cells, yeasts, fungi), and including fractions thereof. In some embodiments, the test sample can include a fluid from a blood culture. In some embodiments, the culture medium can be obtained from any source, e.g., without limitations, research laboratories, pharmaceutical manufacturing plants, hydrocultures (e.g., hydroponic food farms), diagnostic testing facilities, clinical settings, and any combinations thereof.

In some embodiments, the test sample can include a media or reagent solution used in a laboratory or clinical setting, such as for biomedical and molecular biology applications. As used herein, the term "media" refers to a medium for maintaining a tissue, an organism, or a cell population, or refers to a medium for culturing a tissue, an organism, or a cell population, which contains nutrients that maintain viability of the tissue, organism, or cell population, and support proliferation and growth.

As used herein, the term "reagent" refers to any solution used in a laboratory or clinical setting for biomedical and molecular biology applications. Reagents include, but are not limited to, saline solutions, PBS solutions, buffered solutions, such as phosphate buffers, EDTA, Tris solutions, and any combinations thereof. Reagent solutions can be used to create other reagent solutions. For example, Tris solutions and EDTA solutions are combined in specific ratios to create "TE" reagents for use in molecular biology applications.

In some embodiments, the test sample can be a non-biological fluid. As used herein, the term "non-biological fluid" refers to any fluid that is not a biological fluid as the term is defined herein. Exemplary non-biological fluids include, but are not limited to, water, salt water, brine, buffered solutions, saline solutions, sugar solutions, carbohydrate solutions, lipid solutions, nucleic acid solutions, hydrocarbons (e.g. liquid hydrocarbons), acids, gasolines, petroleum, liquefied samples (e.g., liquefied samples), and mixtures thereof.

Embodiments of the Various Aspects Described Herein can be Illustrated by the Following Numbered Paragraphs.

1. A method for determining antibiotic susceptibility of a microbe, the method comprising:
    (i) obtaining a sample suspected of comprising a microbe, wherein the microbe has been extracted or concentrated from a test sample using a microbe-targeting substrate, wherein the microbe-targeting substrate comprises on its surface a microbe-binding molecule;
    (ii) incubating the substrate-bound microbe in the presence of at least one antibiotic agent for a pre-determined period of time; and
    (iii) detecting the growth or functional response of the microbe to the antibiotic agent,
    wherein reduced growth or function in the presence of the antibiotic agent relative to a reference or control sample indicates that the microbe is susceptible to the antibiotic agent.
2. The method of paragraph 1, further comprising incubating the microbe-targeting substrate in a growth medium to achieve sufficient microbial numbers for use.
3. The method of paragraph 1 or 2, wherein the microbe-targeting substrate is selected from the group consisting of nucleic acid scaffolds, protein scaffolds, lipid scaffolds, dendrimers, nanoparticles, microparticles, microtiter plates, filters, fibers, screens, tubes, nanotubes, magnetic particles, microfluidic channels, membranes, microchips, filtration devices, diagnostic strips, dipsticks, extracorporeal devices, spiral mixers, hollow-fiber reactors, and any combination thereof.
4. The method of any of paragraphs 1-3, wherein the microbe-binding molecule is selected from the group consisting of opsonins, lectins, antibodies and antigen binding fragments thereof, proteins, peptides, peptidomimetics, carbohydrate-binding proteins, nucleic acids, carbohydrates, lipids, steroids, hormones, lipid-binding molecules, cofactors, nucleosides, nucleotides, nucleic acids, peptodogylcan, lipopolysaccharide-binding proteins, small molecules, and any combination thereof.
5. The method of any of paragraphs 1-4, wherein the microbe-binding molecule comprises at least a microbial-binding portion of C-type lectins, collectins, ficolins, receptor-based lectins, lectins from the shrimp Marsupenaeus japonicas, non-C-type lectins, lipopolysaccharide (LPS)-binding proteins, endotoxin-binding proteins, peptidoglycan-binding proteins, or any combinations thereof.
6. The method of paragraph 5, wherein the microbe-binding molecule is selected from the group consisting of mannan-binding lectin (MBL), surfactant protein A, surfactant protein D, collectin 11, L-ficolin, ficolin A, DC-SIGN, DC-SIGNR, SIGNR1, macrophage mannose receptor 1, dectin-1, dectin-2, lectin A, lectin B, lectin C, wheat germ agglutinin, CD14, MD2, lipopolysaccharide-binding protein (LBP), *limulus* anti-LPS factor (LAL-F), mammalian peptidoglycan recognition protein-1 (PGRP-1), PGRP-2, PGRP-3, PGRP-4, or any combinations thereof.
7. The method of any of paragraphs 1-6, wherein the microbe-binding molecule is further conjugated to a linker.
8. The method of any of paragraphs 1-7, wherein the microbe-binding molecule further comprises a substrate-binding domain.
9. The method of paragraph 7 or 8, wherein the substrate binding domain is conjugated to a portion of the linker.

10. The method of any of paragraphs 7-9, wherein the substrate binding domain comprises an amino acid sequence of AKT (alanine, lysine, threonine).

11. The method of any of paragraphs 7-10, wherein the linker comprises a Fc portion of an immunoglobulin.

12. The method of any of paragraphs 1-11, wherein the microbe-binding molecule is selected from the group consisting of MBL (mannose binding lectin), FcMBL (IgG Fc fused to mannose binding lectin), AKT-FcMBL (IgG Fc-fused to mannose binding lectin with the N-terminal amino acid tripeptide of sequence AKT (alanine, lysine, threonine)), and any combination thereof.

13. The method of any of paragraphs 1-12, wherein the microbe-binding molecule comprises an amino acid sequence selected from SEQ ID NO. 1, SEQ ID NO. 2, SEQ ID NO. 3, SEQ ID NO. 4, SEQ ID NO. 5, SEQ ID NO. 6, SEQ ID NO. 6, SEQ ID NO. 7, SEQ ID NO. 8, and any combination thereof.

14. The method of any of paragraphs 1-13, wherein the test sample is a biological fluid obtained or derived from a subject, a fluid or specimen obtained from an environmental source, a fluid from a cell culture, a microbe colony, or any combinations thereof.

15. The method of any of paragraphs 1-14, wherein the test sample is a biological fluid selected from blood, plasma, serum, lactation products, amniotic fluids, sputum, saliva, urine, semen, cerebrospinal fluid, bronchial aspirate, bronchial lavage aspirate fluid, perspiration, mucus, liquefied stool sample, synovial fluid, peritoneal fluid, pleural fluid, pericardial fluid, lymphatic fluid, tears, tracheal aspirate, a homogenate of a tissue specimen, or any mixtures thereof.

16. The method of any of paragraphs 1-15, wherein the test sample is a fluid or specimen obtained from an environmental source selected from a fluid or specimen obtained or derived from food products, food produce, poultry, meat, fish, beverages, dairy product, water (including wastewater), ponds, rivers, reservoirs, swimming pools, soils, food processing and/or packaging plants, agricultural places, hydrocultures (including hydroponic food farms), pharmaceutical manufacturing plants, animal colony facilities, or any combinations thereof.

17. The method of any of paragraphs 1-16, further comprising adding an anticoagulant, such as heparin, to the biological sample before extracting the microbe from the biological sample.

18. The method of any of paragraphs 1-17, further comprising diluting the biological sample before extracting the microbe.

19. The method of any of paragraphs 1-18, further comprising incubating the biological sample with the microbe-targeting substrate for about 1 minute to about 60 minutes for extracting the microbe from the biological sample.

20. The method of any of paragraphs 1-19, further comprising washing the microbe-targeting substrate after extracting the microbe from the biological sample.

21. The method of any of paragraphs 1-20, further comprising dividing the sample from step (i) into a plurality of subsamples before proceeding to step (ii).

22. The method of any of paragraphs 1-21, further comprising detaching the microbe from the microbe-binding substrate before proceeding to step (ii).

23. The method of any of paragraphs 1-22, wherein said incubating of step (ii) is performed for about 30 seconds to about 3 days as determined by the rate of microbial division.

24. The method of any of paragraphs 1-23, wherein said incubating of step (ii) is performed for about 30 seconds to about 300 minutes.

25. The method of any of paragraphs 1-24, wherein said incubating of step (ii) is performed for about 300 minutes to about 24 hours.

26. The method of any of paragraphs 1-25, wherein said incubating of step (ii) is performed for about 1 day to about 3 days 27. The method of any of paragraphs 1-26, wherein said incubating of step (ii) is performed at about 15° C. to about 45° C.

28. The method of any of paragraphs 1-27 wherein said incubating of step (ii) is performed in optimized growth media.

29. The method of any of paragraphs 1-28, wherein said detecting of step (iii) comprises determining number, growth, proliferation, function and/or viability of microbes in the sample relative to the reference or the control.

30. The method of any of paragraphs 1-29, wherein said detecting of step (iii) comprises determining microbial cell viability.

31. The method of paragraph 30, wherein said determining microbial cell viability is by an assay selected from the group consisting of cytolysis or membrane leakage, mitochondrial activity or caspase assays, Reactive Oxygen Species (ROS) production, ATP production, pH, functional assays, or genomic, metabolomic, transcriptomic, proteomic assays, and any combinations thereof.

32. The method of paragraph 30 or 31, wherein said determining microbial cell viability is performed by an assay comprising ATP test, Calcein AM, Clonogenic assay, Ethidium homodimer assay, Evans blue, Fluorescein diacetate hydrolysis/Propidium iodide staining (FDA/PI staining), Flow cytometry, Formazan-based assays (MTT/XTT), Green fluorescent protein, Lactate dehydrogenase (LDH), Methyl violet, Propidium iodide, DNA stain, Trypan Blue (a living-cell exclusion dye), TUNEL assay, ROS test, cell labeling or staining (e.g., a cell-permeable dye (e.g., Carboxylic Acid Diacetate, Succinimidyl Ester (Carboxy-DFFDA, SE)), a cell-impermeable dye, cyanine, phenantridines, acridines, indoles, imidazoles, a nucleic acid stain, a cell permeant reactive tracer (e.g., intracellularly-activated fluorescent dyes CMRA, CMF2HC (4-Chloromethyl-6,8-Difluoro-7-Hydroxycoumarin), CMFDA (5-Chloromethylfluorescein Diacetate), CMTMR (5-(and -6)-(((4-Chloromethyl)Benzoyl)Amino)Tetramethylrhodamine), CMAC (7-Amino-4-Chloromethylcoumarin), CMHC (4-Chloromethyl-7-Hydroxycoumarin)), fluorescent DNA dyes (e.g., DAPI, Heochst family, SYBR family, SYTO family, SYTOX family, ethidium bromide, propidium iodide, acridines, or any combinations thereof); chromogenic dyes (e.g., eosin, hematoxilin, methylene blue, azure, or any combinations thereof); cytoplasma stain (e.g., calcofluor white, periodic acid-schiff stain, or any combinations thereof); metabolic stains (e.g., any diacetate dye (including, rhodamine based-dye, fluorescin, or any combinations thereof), resazurin/resorufin (alamar blue); ROS stains (e.g., DCFDA and related family, calcein-acetoxymethyl and related family); membrane stains (e.g., bodipy, FM 1-43, FM 4-64, and functionally equivalent thereof, CellMask™ stains, DiI, DiO, DiA); biologic stains (e.g., labeled antibodies, labeled chitin-binding protein), optical or microscopic imaging, ELISA, mass spectrometric analysis, or any combinations thereof.

33. The method of paragraph 32, wherein the mass spectrometric analysis is performed on intracellular or extracellular peptides, proteins, glycopeptides, lipopeptides, carbohydrates, metabolites, or any combination thereof.

34. The method of any of paragraphs 1-33, wherein said detecting of step (iii) comprises ELISA.

35. The method of any of paragraphs 1-34, wherein said detecting of step (iii) comprises measuring ATP or ROS levels.

36. The method of any of paragraphs 1-35, wherein said detecting of step (iii) comprises labeling the microbe with a labeling molecule.

37. The method of any of paragraphs 1-36, wherein said detecting of step (iii) comprises optical or microscopic imaging.

38. The method of any of paragraphs 1-37, wherein said detecting of step (iii) comprises a flow cytometric assay.

39. The method of any of paragraphs 1-38, wherein said detecting of step (iii) comprises a colorimetric assay.

40. The method of any of paragraphs 1-39, wherein said detecting of step (iii) comprises mass spectrometry.

41. The method of any of paragraphs 1-40, wherein said detecting of step (iii) comprises detecting at least one metabolite.

42. The method of any of paragraphs 1-41, wherein said detecting of step (iii) comprises determining a metabolic profile.

43. The method of any of paragraphs 1-42, wherein said detecting of step (iii) comprises determining at least one transcriptional change or a transcriptional profile.

44. The method of any of paragraphs 1-43, wherein said incubating of step (ii) further comprises immobilizing at least a portion of the substrate-bound microbe from step (i) in a matrix.

45. The method of paragraph 44, wherein the matrix comprises said at least one antibiotic agent.

46. The method of paragraph 44 or 45, wherein the matrix is reactive to the growth or functional response of the microbe in the matrix.

47. The method of any of paragraphs 44-46, wherein the matrix comprises at least one detection agent to determine at least metabolism or viability of the microbe in the matrix.

48. The method of any of paragraphs 44-47, wherein the matrix is overlaid with a medium containing at least one antibiotic agent or detection agent or any combination thereof that can diffuse into the matrix to reach the microbe.

49. The method of paragraph 48, wherein said at least one detection agent is selected from the group consisting of resazurin or molecules derived from a nucleic acid binding agent, calcein AM, a tetrazolium salt, a protease marker, a pH indicator, an ATP indicator, a redox indicator, an esterase indicator, an ROS indicator, a cell-permeable dye (e.g., Carboxylic Acid Diacetate, Succinimidyl Ester (Carboxy-DFFDA, SE)), a cell-impermeable dye, cyanine, phenantridines, acridines, indoles, imidazoles, a nucleic acid stain, a cell permeant reactive tracer (e.g., intracellularly-activated fluorescent dyes CMRA, $CMF_2HC$ (4-Chloromethyl-6,8-Difluoro-7-Hydroxycoumarin), CMFDA (5-Chloromethylfluorescein Diacetate), CMTMR (5-(and -6)-(((4-Chloromethyl)Benzoyl) Amino)Tetramethylrhodamine), CMAC (7-Amino-4-Chloromethylcoumarin), CMHC (4-Chloromethyl-7-Hydroxycoumarin)), fluorescent DNA dyes (e.g., DAPI, Heochst family, SYBR family, SYTO family (e.g., SYTO 9), SYTOX family (e.g., SYTOX green), ethidium bromide, propidium iodide, acridines, or any combinations thereof); chromogenic dyes (e.g., eosin, hematoxilin, methylene blue, azure, or any combinations thereof); cytoplasma stain (e.g., calcofluor white, periodic acid-schiff stain, or any combinations thereof); metabolic stains (e.g., any diacetate dye (including, rhodamine based-dye, fluorescin, or any combinations thereof), resazurin/resorufin (alamar blue); ROS stains (e.g., DCFDA and related family, calcein-acetoxymethyl and related family); membrane stains (e.g., bodipy, FM 1-43, FM 4-64, and functionally equivalent thereof, CellMask™ stains, Dil, DiO, DiA); biologic stains (e.g., labeled antibodies, labeled chitin-binding protein), or any combinations thereof.

50. The method of any of paragraphs 44-49, wherein the matrix is selected from a group consisting of an agarose gel, a collagen gel, a matrigel, an alginate gel, a biocompatible polymer gel, a hydrogel, gelatin, a fibrin gel, and any combinations thereof.

51. The method of any of paragraphs 1-50, further comprising determining an identity of the microbe.

52. The method of paragraph 51, wherein the identity of the microbe is determined by subjecting the microbe that is untreated with said at least one antibiotic agent to mass spectrometry or surface enhanced Raman spectroscopy or nucleic acid amplification or hybridization or any physical or chemical methods known to identify microbes or a plurality of distinct identification markers for specific microbes or any combinations thereof.

53. A kit for determining antibiotic susceptibility of a microbe in a sample, the kit comprising: (a) one or more containers containing a microbe-targeting substrate coated with a plurality of microbe-binding molecules; (b) an antibiotic agent; and (c) optionally a reagent.

54. The kit of paragraph 53, further comprising one or more containers containing a matrix for immobilizing a microbe.

55. The kit of paragraph 53 or 54, wherein the matrix further comprises a detection agent for determining at least metabolism or viability of a microbe.

56. The kit of any of paragraphs 53-55, further comprising at least one solid support for immobilizing the microbe thereon.

57. The kit of any of paragraphs 53-56, further comprising one or more containers containing the detection agent for determining at least metabolism or viability of a microbe.

58. A system for determining antibiotic susceptibility of a microbe comprising:
   (i) a capture or separation system for capturing a microbe from a biological fluid, wherein, the capture or separation system comprises a microbe-targeting substrate, wherein the microbe-targeting substrate comprises on its surface a microbe-binding molecule;
   (ii) an incubation system for incubating the microbe with or without an antibiotic agent; and
   (iii) a detection system for detecting microbe growth or a functional response after incubation.

59. The system of paragraph 58, wherein the incubation system comprises at least one multi-well plate holder.

60. The system of any of paragraphs 58 or 59, wherein at least one of the capture or separation system, the incubation system, and the detection system is adapted to be a module of a microfluidic device.

61. The system of any of paragraphs 58-60, wherein at least one of the capture or separation system, the incubation system, and the detection system comprises a microfluidic channel.

62. The system of any of paragraphs 58-61, further comprising an identification system for determining an identity of the microbe.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "antibody" as used herein refers to immunoglobulin molecules and immunologically active portions of immunoglobulin molecules (molecules that contain an antigen binding site which specifically binds an antigen), including monoclonal antibodies (including full length monoclonal antibodies), polyclonal antibodies, multispecific antibodies (for example, bispecific antibodies), chimeric antibodies, humanized antibodies, human antibodies, and single chain antibodies (scFvs).

The term "peptide" refers to a polymer of amino acids, or amino acid analogs, regardless of its size or function. In some embodiments, the term "peptide" refers to small polypeptides, e.g., a polymer of about 15-25 amino acids.

The term "oligonucleotide" as used herein refers to a short nucleic acid polymer, typically with twenty or fewer bases.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein.

In some embodiments, the subject is a mammal. The mammal can be a human, non-human primate, mouse, rat, dog, cat, horse, or cow, but are not limited to these examples. Mammals other than humans can be advantageously used as subjects that represent animal models of diseases or disorders.

A subject can be one who has been previously diagnosed with or identified as suffering from or having a disease or disorder caused by any microbes or pathogens described herein. In some embodiments, a subject can be one who is suspected of or at risk of having a disease or disorder caused by any microbes or pathogens described herein. By way of example only, a subject can be diagnosed with or suspected of having sepsis, inflammatory diseases, or infections.

In some embodiments, a subject can include domestic pets (e.g., but not limited to, dogs and cats). Accordingly, some embodiments of the assays, methods, kits and/or systems described herein can be used for veterinary applications.

As used herein, the term "peptidomimetic" means a peptide-like molecule that has the activity of the peptide on which it is structurally based. Such peptidomimetics include chemically modified peptides, peptide-like molecules containing non-naturally occurring amino acids, and peptoids, and have an activity such as the cardiac specificity of the peptide upon which the peptidomimetic is derived (see, for example, Goodman and Ro, Peptidomimetics for Drug Design, in "Burger's Medicinal Chemistry and Drug Discovery", Vol. 1 (ed. M. E. Wolff; John Wiley & Sons 1995), pages 803-861).

A variety of peptidomimetics are known in the art and can be used with a method described herein, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an Nα-Cα cyclized amino acid; an Nα-methylated amino acid; αβ- or γ-amino cycloalkane carboxylic acid; an α,β-unsaturated amino acid; a β,β-dimethyl or β-methyl amino acid; αβ-substituted-2,3-methano amino acid; an N—Cδ or Cα-Cδcyclized amino acid; a substituted proline or another amino acid mimetic. A peptidomimetic which mimics peptide secondary structure can contain, for example, a non-peptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; transolefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a peptide of described herein, as well as potential geometrical and chemical complementarity to a cognate receptor. Where no crystal structure of a peptide described herein is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a peptide described herein, for example, having specificity for the microbes.

The terms "homology" as used herein refers to sequence similarity between two peptides or between two nucleic acid molecules. Homology can be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology refers to a function of the number of identical or similar amino acids at positions shared by the compared sequences. A sequence which is "unrelated" or "non-homologous" shares less than 40% identity. Determination of homologs of the genes or peptides described herein can be easily ascertained by the skilled artisan.

The term "conservative substitution," when describing a polypeptide, refers to a change in the amino acid composition of the polypeptide that does not substantially alter the polypeptide's activity, fore examples, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or nonpolar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In addition, individual substitutions, deletions or additions that alter, add or delete a single amino acid or a small percentage of amino acids in an encoded sequence are also "conservative substitutions." Insertions or deletions are typically in the range of about 1 to 5 amino acids.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Rapid Antibiotic Sensitivity Testing Based on Magnetic Separation and Microscopy Bacteremia, a condition that is also known as bacterial sepsis or blood poisoning, describes a bacterial infestation of a patient's blood and is a major killer in the US and worldwide. Worldwide, there are 18 million cases of sepsis per year, which result in over 6 million deaths, and in the US alone there are 750,000 cases a year, which result in over 200,000 deaths. When physicians suspect that a patient is suffering from bacteremia they must act quickly: since bacteria can divide very rapidly, every hour lost before the correct treatment is administered can make a crucial difference in patient outcome. Consequently, physicians must rush to answer two questions: does the patient indeed have bacteremia, and if so, what antibiotics to prescribe. Unfortunately, the present approach to answering these questions—blood culture—takes two days or more to yield an answer, which quite often proves too long.

The inventors have developed a technique for detecting bacteremia and providing the causative agent's antibiotic resistance profile that can yield its answers in a few hours or less. The technique consists of the following steps: (i) extraction and concentration of pathogens from blood using functionalized magnetic beads; (ii) splitting into subsamples and incubation with antibiotic-supplemented growth media;

(iii) fluorescent labeling of pathogens; (iv) microscopic imaging and counting of the extracted, labeled pathogens.

Pathogen Extraction and Concentration:

Previous work by the inventors had demonstrated a method for the extraction and concentration of pathogens from blood that is based on magnetic beads that are coated with mannose binding lectin (MBL). MBL is an innate-immune-system protein that adheres to most blood-borne pathogens, and so it makes the magnetic beads suitably selective. Using this method, the inventors can capture individual pathogen cells from large sample volumes. The inventors have also used alternatives to MBL, including antibodies, other lectins and vancomycin.

Brief Culture in the Presence of Antibiotics:

Once the pathogen has been extracted from blood, sample is split into several subsamples. In turn, a sufficient amount of bacterial growth medium (e.g. LB broth) that is supplemented with one or more of the antibiotics to which the bacteria's sensitivity is in question is added to each subsample. At least additional subsample is supplemented with growth medium that is not supplemented with antibiotics, for use as a reference.

The subsamples are incubated under substantially identical conditions (e.g., heated to a suitable temperature) and enabling the bacteria to multiply. This incubation is continued for only as long as is necessary to create a sufficient and robust difference in bacterial counts between samples that are antibiotic inhibited to those that are not as measured by the subsequent readout steps. This incubation time is likely between half an hour and two hours.

Fluorescent Staining:

Although the magnetic capture step should specifically extract pathogens, it is can be beneficial to use a subsequent staining with a reagent that enhances this specificity. Furthermore, using a fluorescent reagent can provide excellent signal-to-noise in the imaging/readout, thus maintaining sensitivity. Inventors have used a variety of fluorescent stains, which are typically conjugates of a fluorophore or quantum dot with a probe element. There are many suitable stains, including ones based on MBL, gram-specific antibodies and wheat germ agglutinin. The staining can be done either prior to or after the pathogens have been laid out for microscopic imaging.

Microscopic Imaging:

Microscopy of fluorescently stained bacteria can yield images from which one can easily count small numbers of bacterial cells. Since microscopy works best when the sample is presented as a flat layer (so that the entire image is within the microscope's depth of field), care must be taken to present the sample suitably. Inventors have identified three different ways in which one can present the sample in this fashion: on the surface of the magnetic element used for magnetic separation, in a microfluidic channel or slide-coverslip sandwich with a small channel-height/gap, and after filtration through a membrane-type filter. The advantage of using membrane filters is that they can also be used to remove many of the magnetic beads that are not bound to a pathogen, hence removing potential obstructions. The inventors and others have also developed filtration cells that allow in situ imaging of the captured portion.

Analysis:

Once bacterial counts for the reference and antibiotic-treated subsamples have been obtained, antibiotic resistance can be determined by comparing these numbers. In particular, subsamples that are resistant to the antibiotics with which they were treated display counts that are similar to the reference, indicating that their growth was unencumbered. Subsamples in which growth was antibiotic-inhibited, in contrast, do not benefit from the incubation time, and so their counts are lower.

As with blood culture, the method disclosed herein is based on the direct measurement of bacteria's ability to grow in the presence of the tested antibiotics. This direct measurement provides the clinically relevant result that the physicians are seeking and is thus superior to methods that test for indirect properties, e.g., presence of antibiotic-resistance genes or enzymes.

In contrast to blood culture, the method disclosed herein is able to detect bacteria and their antibiotic sensitivity using short growth times. This is enabled by the inventors' microscopic approach's ability to detect and quantify small numbers of bacterial cells, and in turn, small difference in bacterial counts. Consequently, whereas blood-culture based antibiotic resistance typically requires three lengthy incubation steps, the method disclosed herein requires only one short step.

Further, the method disclosed herein can be applied with little modification to the analogous case of fungemia—a fungal infestation of blood. In this case, the antibiotic matrix can be replaced with a suitable set of antifungal drugs, and the capture reagent chosen or supplemented to ensure fungal capture. Moreover, bacterial and fungal detection can easily be combined into the same test as is needed, e.g., bacterial detection, fungal detection, and antibiotic sensitivity.

Example 2

Rapid Antibiotic Sensitivity Testing Based on Magnetic Separation and ELISA

The inventors have developed a method for rapid isolation, detection, and antibiotic susceptibility determination of bacteremia or other microbial infections using magnetic separation and ELISA/metabolic readout. This provides a technique for detecting bacteremia and determining the antibiotic resistance profile of the causative agent within a few hours or less.

Generally, the method comprises: (i) extraction and concentration of pathogens from blood using functionalized magnetic beads; (ii) splitting into subsamples and incubation with antibiotic-supplemented media (Yeast extract free media for ELISA or other for Luciferase based assay); and (iii) detection of pathogen growth using an ELISA assay (Enzyme Linked Immunosorbent Assay) or Luciferase detection of ATP production assay, for example BACTI-TER-GLO™ Microbial Cell Viability Assay from Promega (Cat No. G8230).

Pathogen Extraction and Concentration:

The inventors have previously demonstrated a method for the extraction and concentration of pathogens from blood that is based on magnetic beads that are coated with an engineered mannose binding lectin (MBL). MBL is a key component of the innate immune system, which binds to carbohydrate structures containing mannose, N-acetyl glucosamine and fucose on the surface of pathogens and that are not found on mammalian cells. MBL binds to at least 36 species of bacteria (e.g. Gram positive: *Staphylococci*, MRSA, VRSA, Streptococci, *Clostridium*; Gram negative: *Pseudomonas, E. coli*, Klebsiella), 17 viruses (e.g. CMV, HIV, Ebola, HSV, HepB), 20 fungi (e.g., *Candida, Aspergillus, Cryptococcus*), and 9 parasites (e.g. *Malaria, Schistosoma*), in addition to at least one molecular toxin (e.g., LPS endotoxin). Consequently, MBL serves as a broad-spectrum capture reagent, allowing a wide range of pathogens to be extracted and concentrated from blood samples. The inventors had demonstrated magnetic captured using FcMBL, a form that were engineered for better properties (e.g., reduced complement activation) and improved recombinant expression. Nevertheless, the inventor and others have also used alternatives to MBL, including antibodies, other lectins and vancomycin.

Brief Culture in the Presence of Antibiotics:

Once the pathogens are captured from blood, the method comprises splitting the bead/pathogens into several subsamples. Each subsample is added to a sufficient amount of bacterial growth medium (e.g., custom yeast extract free media "F media" [2% glycerol, 0.99 mM KaHPO4, Supplement EZ, ACGU, MOPS, 5 mM $Ca^{2+}$, 0.1% Tween, 2.5 ul Beads] that is supplemented with one or more of the antibiotics to which the bacteria's sensitivity is in question, including at least one reference subsample of growth medium that is not supplemented with antibiotics. The set of subsamples samples are incubated in a culture plate (96 deep well culture plate) under substantially identical conditions to enable the bacteria to multiply. This can be done, for example, at 37° C. and in high-speed shaker/incubator to yield optimal bacterial growth conditions. This incubation continues as only as long as is necessary to create a sufficient and robust difference in bacterial counts between samples that are antibiotic inhibited and those that are not as measured by our subsequent readout steps. This incubation time is typically between two hours and four hours.

Enzyme-Linked Assay:

The antibiotic sensitivity is determined by comparing the growth of bacteria in the presence of antibiotics versus reference samples: after the brief culture period, subsamples with resistant bacteria contain approximately the same bacterial counts as the reference, whereas susceptible ones contain smaller numbers. Consequently, relative counts in the various subsamples are evaluated. To this end, the inventors have developed an enzyme-linked assay (ELISA) that uses an FcMBL-HRP conjugated general pathogen probe avoiding the need of identifying the resistant pathogen. The inventors add the FcMBL probe reagent that has been conjugated with a suitable enzyme (typically horseradish peroxidase, HRP). Following incubation the subsamples are washed to remove unbound probe. Each subsample now contains specifically bound probe (with it reporter enzyme) that is indicative of the bacterial count. The reporter-enzyme's substrate (typically TMB in the case of HRP) is added in order to "develop" the assay and produce a readable output (a colorimetric change, which is measurable as light absorption at particular wavelengths).

In one embodiment, the inventors have used FcMBL-HRP as the enzyme-linked reporter. Reagents based on MBL, and FcMBL in particular, attach selectively to a broad range of pathogens, and so they enable the method described herein to detect the majority of blood-borne pathogens with high sensitivity and specificity. Further amplification of this signal could be obtained by multimerizing the recognition molecule (FcMBL, etc.) and/or the multimerizing the detection enzyme (HRP, etc.). For instance, phage expression can be used to yield multimerized MBL and provide a scaffold to increase the concentration of HRP (either through direct coupling of HRP to the phage particles or using an HRP-antiM13 conjugated antibody).

It is to be understood that one can also use probe reagents that provide a different selectivity than that used for magnetic capture (e.g., MBL). For example, one can use wheat germ agglutinin, which binds gram positive and gram negative bacteria but does not bind to fungi, or antibodies, which are specific to gram positive or gram negative bacteria.

Figure 2:
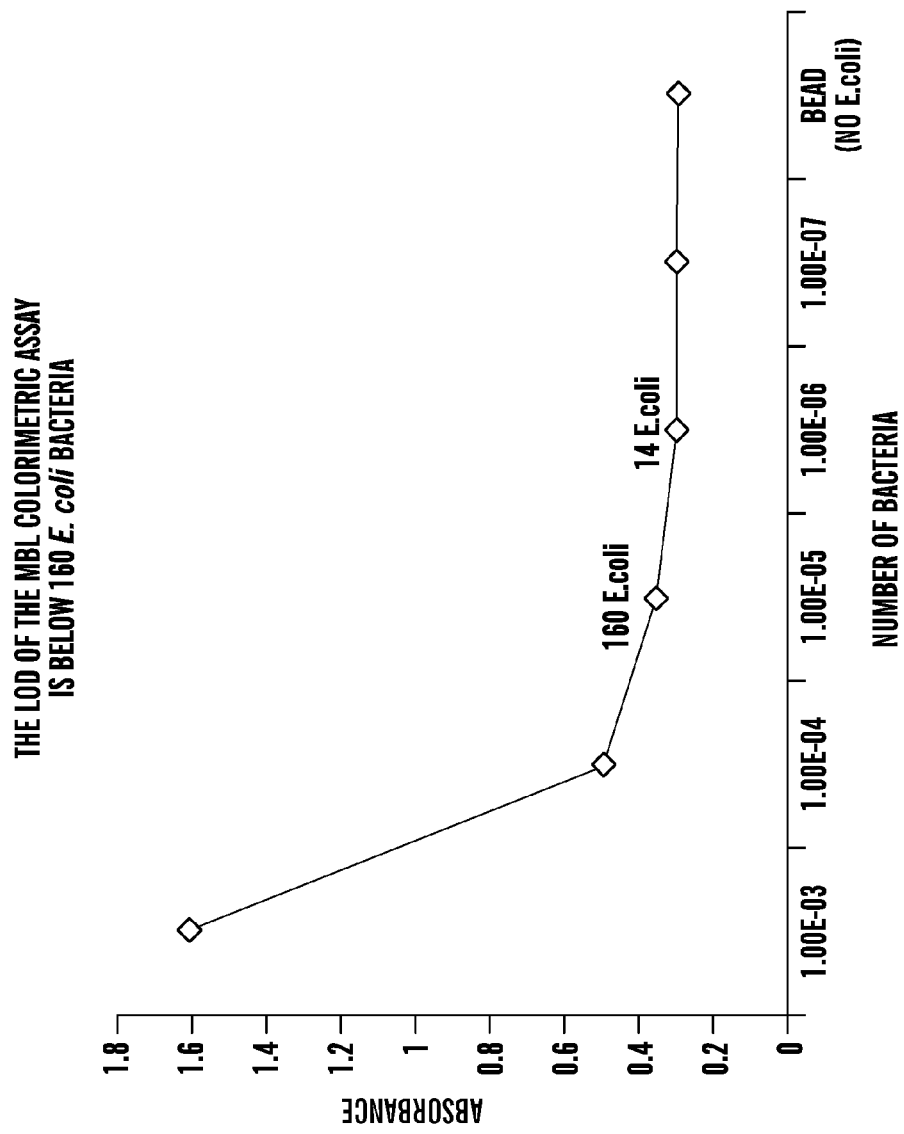
FIG. 2 is a line graph showing sensitivity (limit of detection=LOD): Serial dilutions of $E.\ coli$ were used to determine the LOD of the MBL linked with HRP (FcMBL-HRP) ELISA.

Preliminary Results:

To determine antibiotic susceptibility the inventors used both colony counts ("longterm" testing) and the FcMBL ELISA. As shown in FIG. 2, the ELISA assay has a limit of detection of below 160 bacteria.

Figure 3A:
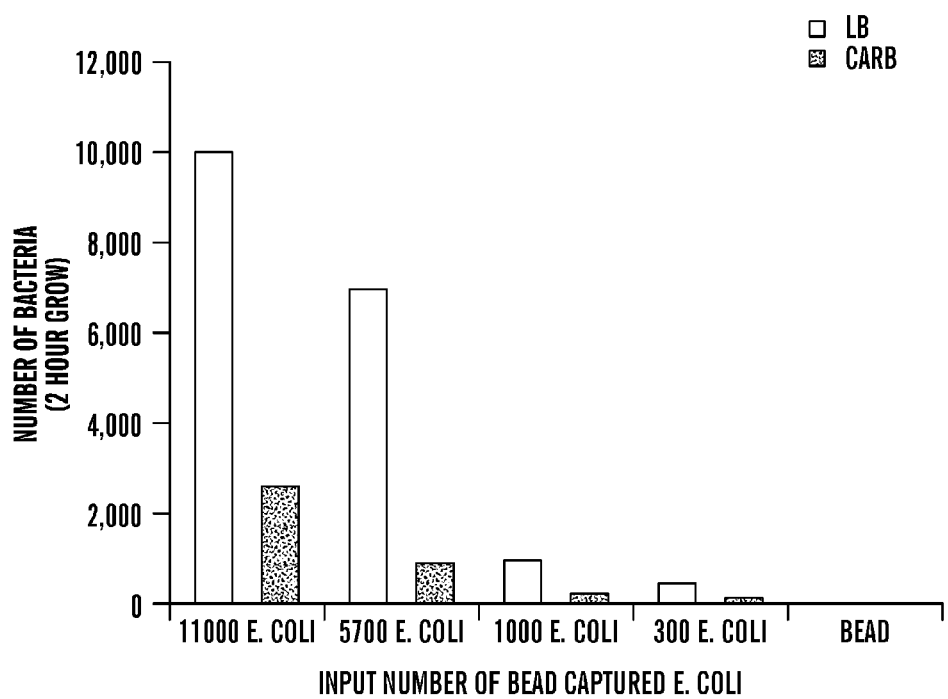
FIGS. 3A and 3B are bar graphs showing antibiotic sensitivity (bactericidal antibiotic Carbenicillin (100 μg/ml) or the bacteriostatic antibiotic Spectinomycin). Bacteria were captured by FcMBL and cultured for 2 hours at 37° C. Due to low number of bacteria detected in the Carbenicillin samples, data is also presented in a separate chart (FIG. 3B).
Figure 3B:
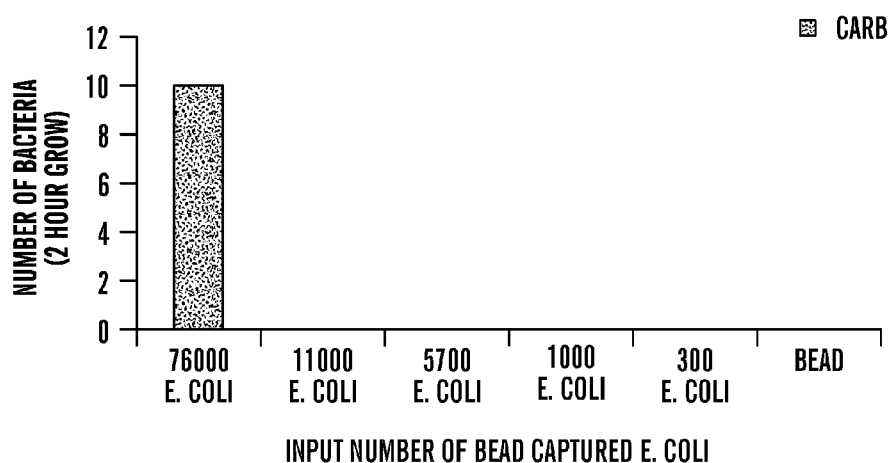

In preliminary studies, the inventors tested the discrimination of the antibiotic susceptibility assay described herein with a range of titers of DH5alpha *E. coli* (corresponding to blood titers from a range of sepsis patients from septic shock to SIRS) FcMBL bead captured bacteria were cultured for 2 hours at 37° C. with vigorous agitation/aeration in Luria Broth (LB) or in LB supplemented with the bacteriocidal antibiotic Carbenicillin or the bacteriostatic antibiotic Spectomycin. The bacteria were quantified on LB Agar plates. In all cases, the inventors were able to discriminate between the growth in LB compared with growth in LB with bacteriocidal or bacteriostatic antibiotic (see FIG. 3). The counts with the bacteriocidal antibiotic were the lowest of the three conditions tested. As shown in FIG. 3, the assay was able to discriminate between these three conditions even at the lowest titer of *E coli*—300 colonies.

Figure 4:
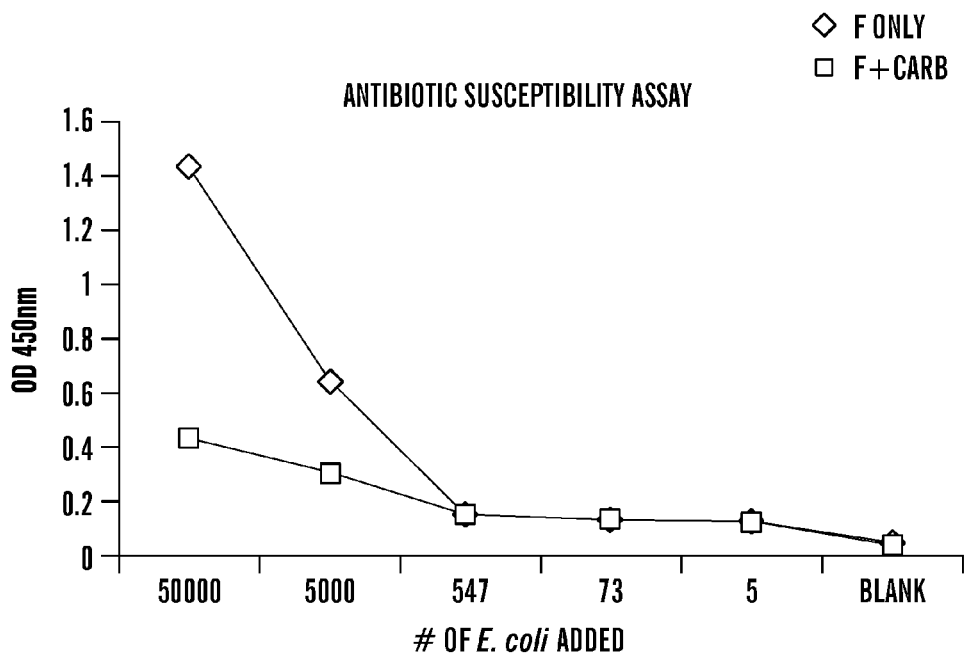
FIG. 4 is a line graph showing antibiotic susceptibility of wild-type $E.\ coli$: Serial dilution of $E.\ coli$ were captured by FcMBL beads for 10 min, transferred to 1 ml F media (2% glycerol, 0.99 mM $KaHPO_4$, Supplement EZ, ACGU, MOPS, 5 mM $Ca^{++}$, 0.1% Tween) with or without carbenicillin (100 ug/ml), cultured for 4 hours at 37° C. shaking at 950 rpms, and growth difference was determined by FcMBL ELISA.
Figure 5:
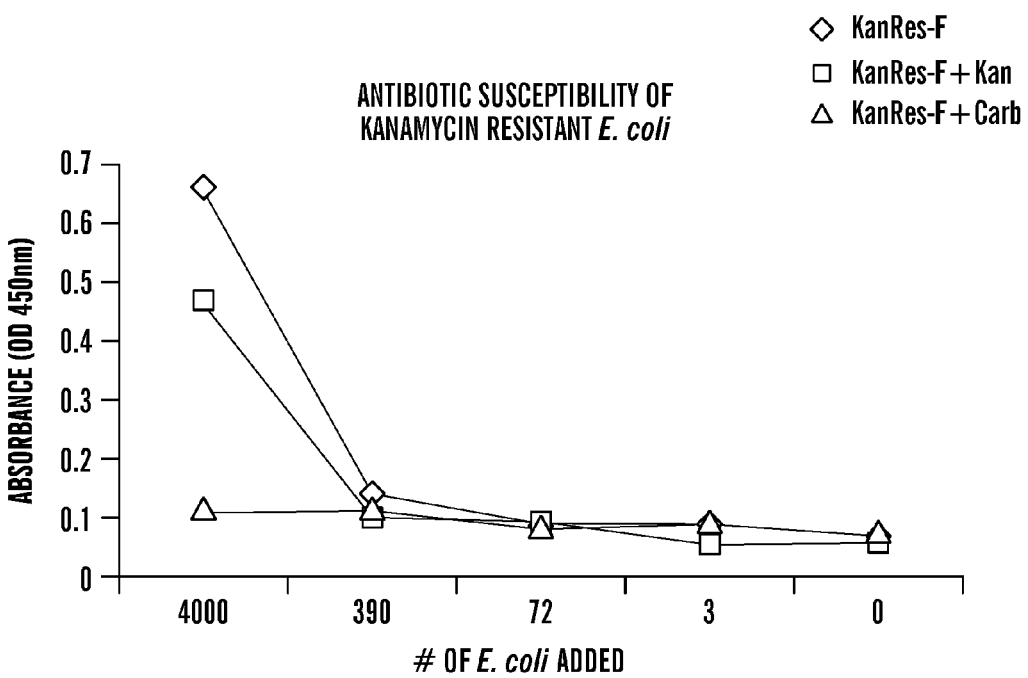
FIG. 5 is a line graph showing antibiotic susceptibility of $Kan^{res}$ $E.\ coli$: Serial dilution of the two $E.\ coli$ were captured by FcMBL beads for 10 min, transferred to 1 ml F media with or without antibiotic-carbenicillin (100 ug/ml) or kanamycin (50 ug/ml), cultured for 4 hours at 37° C. 950 rpms, and growth difference determined by FcMBL ELISA.
Figure 6:
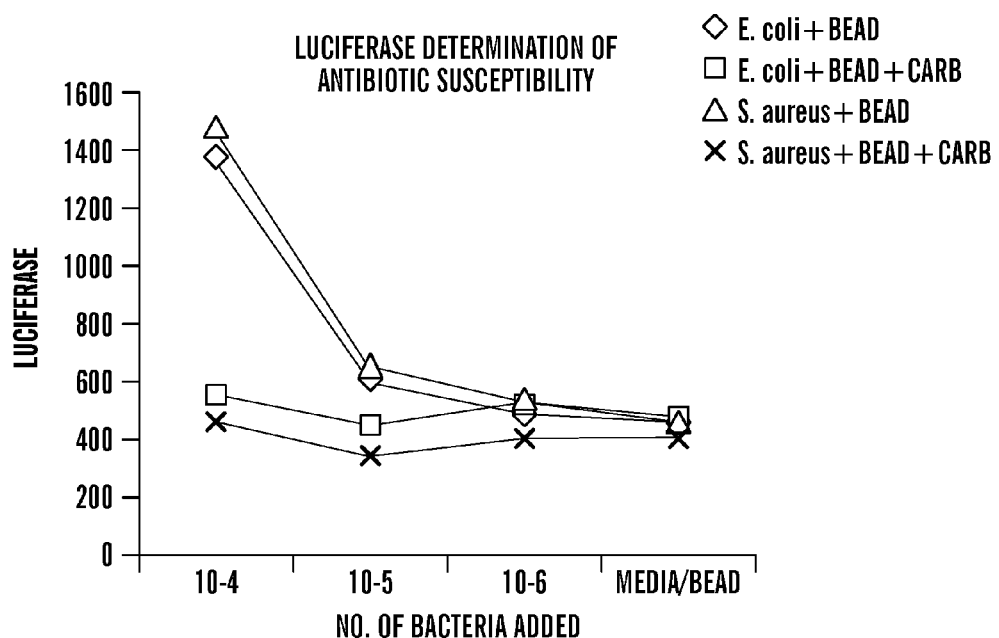
FIG. 6 is a line graph showing determination of antibiotic susceptibility using the luciferase assay. Serial dilutions of $E.\ coli$ and $S.\ aureus$ were captured by FcMBL beads (10 mins), transferred to 1 ml Mueller Hinton broth and growth determined by BACTITERGLO® luciferase assay (100 ul of culture). The LOD was determined to be 40 cfu/ml after 3 hours of growth.
Figure 7:
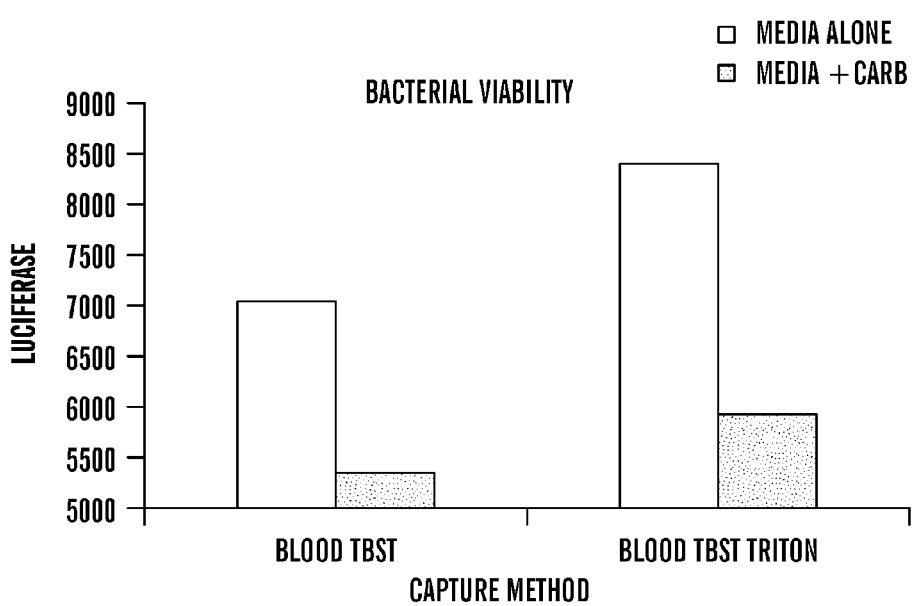
FIG. 7 shows antibiotic susceptibility of $S.\ aureus$ captured from blood. Human blood with 1:1 TBST Ca 5 mM with or without 1% Triton was spiked with 10 ul of diluted $S.\ aureus$ and the bacteria captured with FcMBL beads. The captured bacteria following 3 washes (1x capture buffer and 2×TBST Ca) were transferred to 1 ml Mueller Hinton broth with or without 100 ug/ml Carbenicillin, incubated at 37° C. 950 rpms for 4 hours, and growth determined by BACTITERGLO® luciferase assay (100 ul of culture).

Rapid Detection of Antibiotic Susceptibility:

For the rapid determination of antibiotic susceptibility the inventors used the FcMBL bead capture and growth with the FcMBL-HRP ELISA. The growth was carried out for 4 hours (grown in F media), beads collected, and bacteria growth measured by Fc-MBL ELISA. The experiment was performed with both wt *E. coli* (FIG. 4) and a Kanamycin resistant *E. coli* (FIG. 5). As seen from FIGS. 5 and 6, the assay was able to rapidly determine (3-5 hours) the antibiotic susceptibility of captured bacteria without the need to identify the bacteria.

Rapid Detection of Antibiotic Susceptibility—2:

The use of the ELISA to determine bacterial growth requires the use of a yeast extract free media. For pathogens that require yeast extract in the media the inventors developed the assay with a secondary readout based on the ATP levels (determines bacterial viability and growth) using a luciferase reporter. One exemplary assay for ATP levels is from Promega Corp. which uses a proprietary luciferase reporter for ATP levels. The inventors tested the secondary assay measuring growth of bacteria in combination with the FcMBL bead capture and growth. Conditions of capture and growth were as described above. The luciferase assay was performed as outlined by the manufacturer (only 100 ul of the culture is measured for activity—bacterial growth). Preliminary results are outlined in FIG. 6. As seen, combination of these procedures allowed the determination of antibiotic susceptibility in 3-5 hours with a detection limit of 40 cfu/ml for the *E. coli*.

Summary and Remarks:

In this example, the inventors used two different methods for the detection of antibiotic susceptibility of captured bacterial samples that do not require the previous identification of the pathogen. The methods are based on the direct measurement of bacteria's ability to grow in the presence of the tested antibiotic agents. This direct measurement provides the clinically relevant result that a physician seeks and is thus superior to methods that test for indirect properties, e.g., presence of antibiotic-resistance genes or enzymes. In contrast to blood culture, the method described herein is able to detect pathogens and their antibiotic sensitivity using short growth times and requires only one short culture step. Furthermore, since MBL and FcMBL serve as broad-spectrum pathogen binding molecules, there is no need to specifically identify the pathogen, either for extraction or for antibiotic sensitivity testing.

Further, the methods can be applied with little modification to the analogues case of fungemia—a fungal infestation of blood. In this case, the antibiotic matrix can be replaced with a suitable set of antifungal drugs, and the capture reagent (e.g. MBL) chosen or supplemented to ensure fungal capture. Moreover, bacterial and fungal detection can easily be combined into the same test as is needed, e.g., bacterial detection, fungal detection, and antibiotic sensitivity.

Example 3

Plating Captured/Outgrown Bacteria can Generate Artificially Low Counts

Capture efficiency of Akt-FcMBL beads was determined by plate counts
  5 ul Akt-FcMBL beads+10 ul of either S. aureus or E. coli in 1 mL TBST-Ca$^+$
  Hula 10 min
  Wash 1× in TBST-Ca$^+$ while on magnet
  Counts:
  Number of bacteria added (input), supernatant from beads (uncaptured), and bead fraction post wash (captured)

Figure 8:
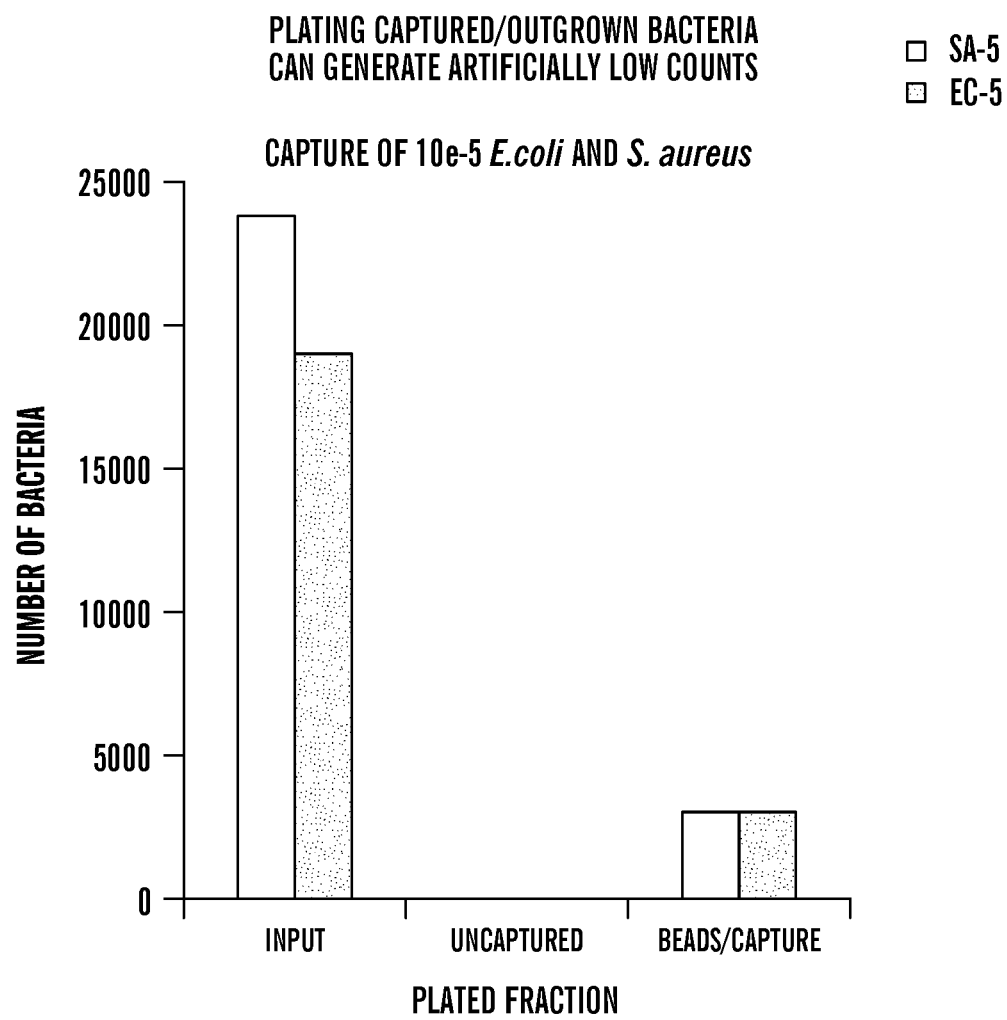
FIG. 8 is a bar graph showing plating captured/outgrown bacteria generates artificially low counts.

As seen in FIG. 8, plating of bead fractions can generate artificially low readouts of bacteria number. Thus, readouts other than plating (such as Fc-MBL ELISA, metabolic assays—ATP luminescence) can be more useful for measuring growth of bacteria isolated with the Akt-FcMBL beads.

Without wishing to be bound by a theory, the FcMBL beads are binding all the bacteria. However, these clump together and so the standard technology of plating out and counting colonies may not be viable to quantify the number of pathogens captured the results are artificially low). Therefore, one may have to use other assays to quantify the captured pathogens.

Example 4

ATP Luminescence is a More Sensitive Readout of Viability than ROS

Figure 9B:
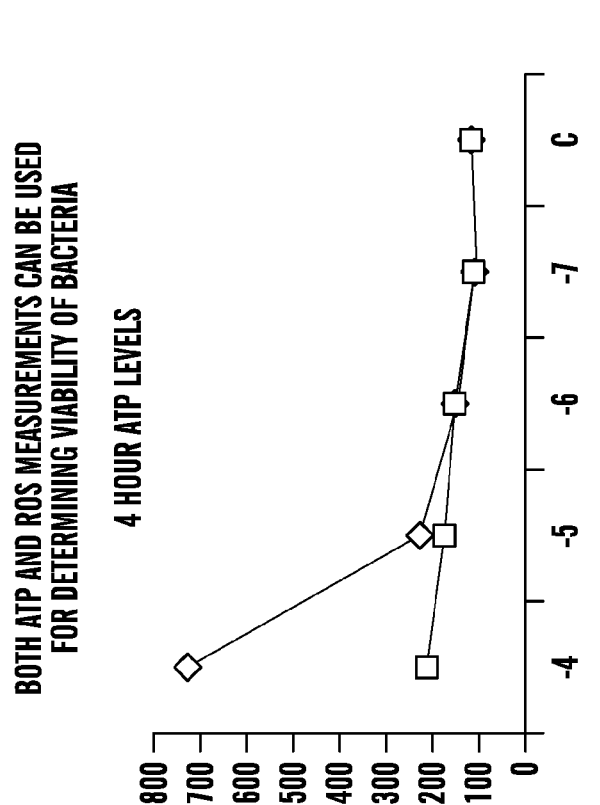
FIGS. 9A and 9B are line graphs showing both reactive oxygen species (ROS) assay (FIG. 9A) and ATP Luminescence (FIG. 9B) assays can be used. ROS LOD=-3 (~20,000 $S.\ aureus$ added), ATP Luminescence LOD=-5 (310 $S.\ aureus$ added).
Figure 9A:
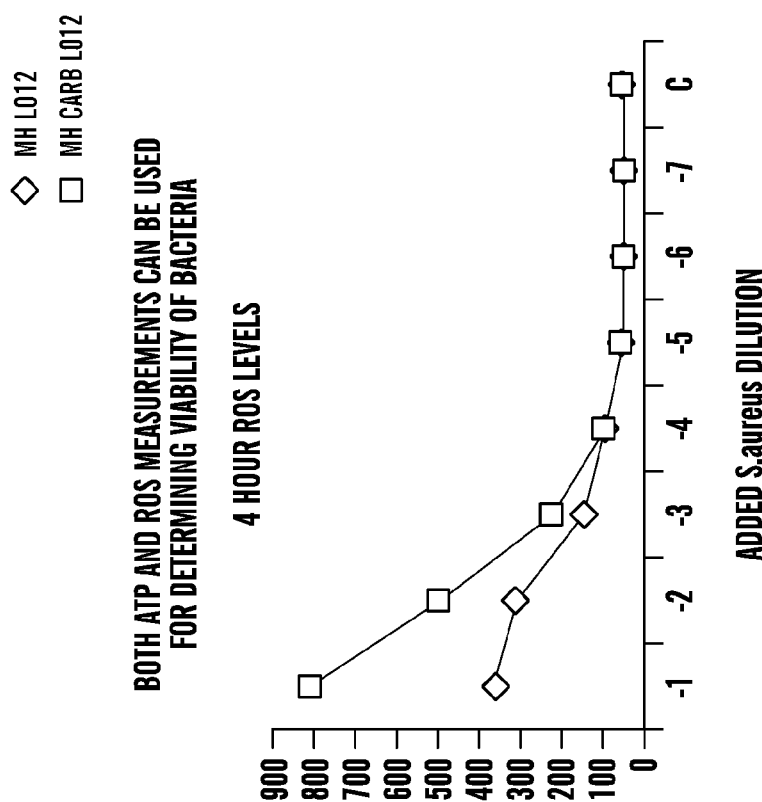

Serial dilutions of S. aureus were grown in Mueller Hinton broth with or without carbenicillin (100 ug/ml, 500 ul media, 37° C., at 950 rpm). ROS and ATP levels were determined at 4 hours in duplicate cultures. FIG. 9A, ROS—Luminol derivative L-012 (2.5 ul of 20 mM+100 ul culture, 1 min, and luminescence determined). FIG. 9B, ATP—BACTITERGLO® luciferase (100 ul+100 ul culture, 5 min, and luminescence determined).

Example 5

Figures 10A, 10B:
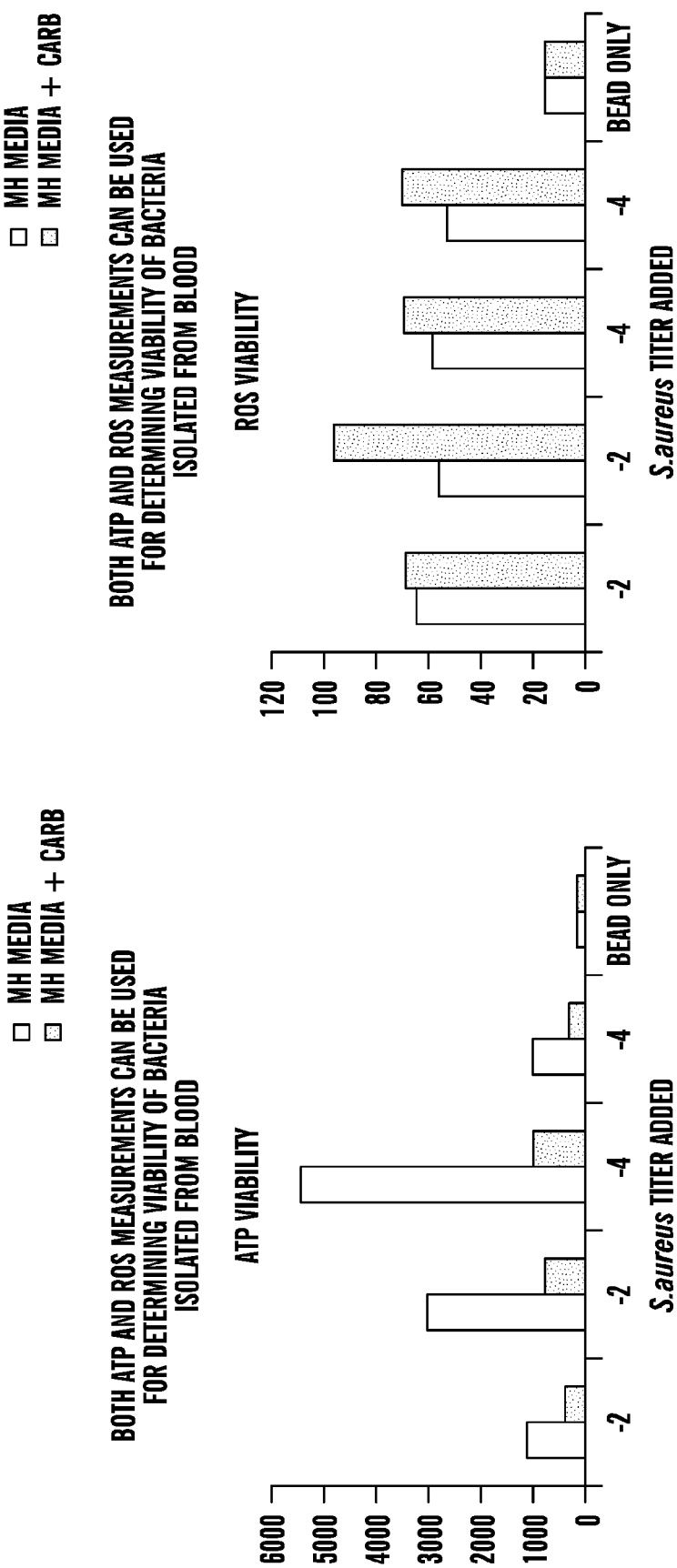
FIGS. 10A and 10B are bar graphs showing both ATP (FIG. 10A) and ROS (FIG. 10B) measurements can be used for determining viability of bacterial isolated from blood. However, ATP luciferase is more sensitive. (-4 titer=5000 $S.\ aureus$ added).
Figures 11A, 11B:
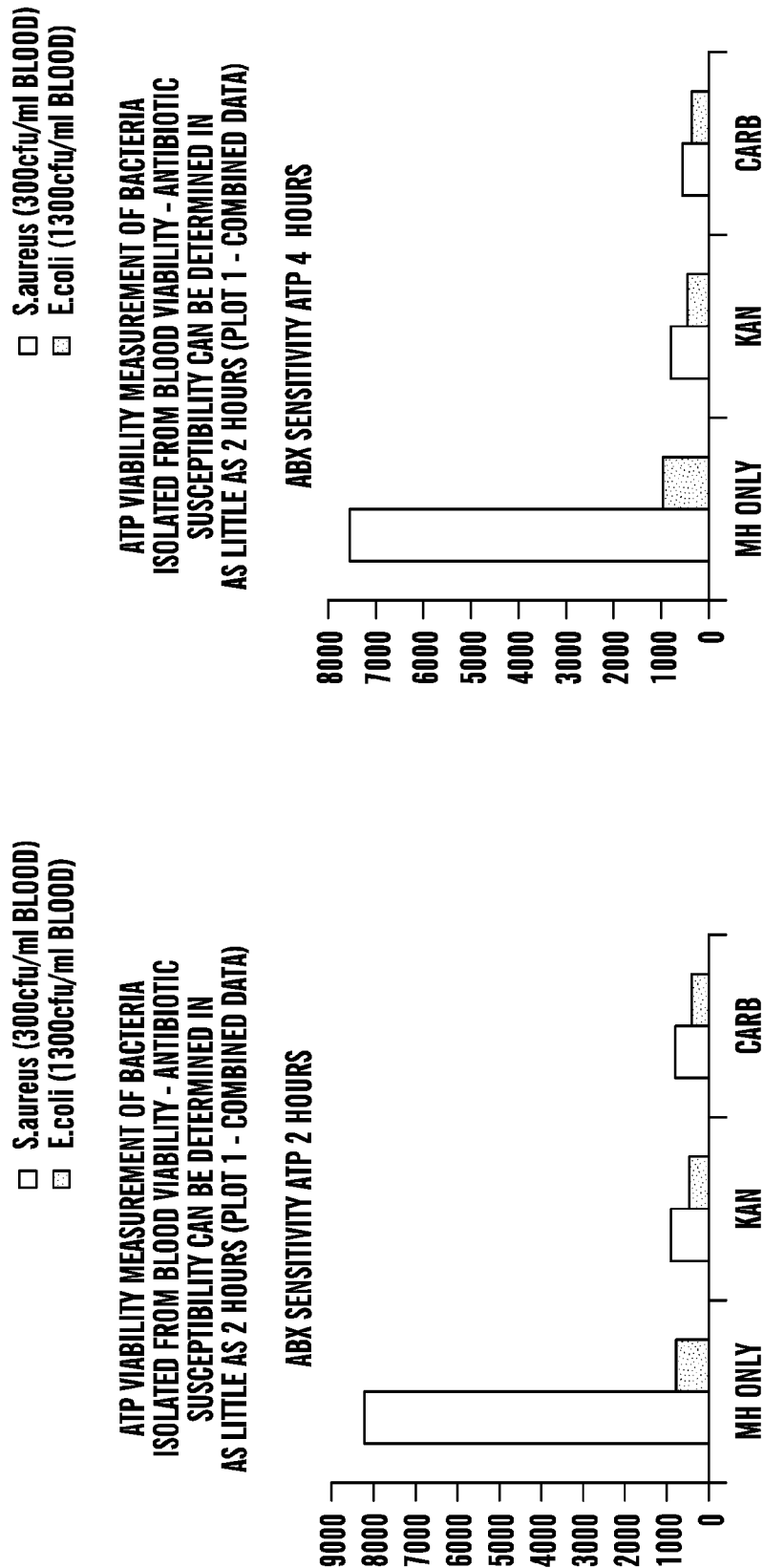

Both ATP and ROS Measurements can be Used for Determining Viability of Bacteria Isolated from Blood Dilutions of S. aureus ($10^{-2}$, $10^{-4}$ fold dilutions) were added to 1 ml blood, captured by Akt-FcMBL beads, washed and grown in Mueller Hinton broth with or without carbenicillin (100 ug/ml). ROS and ATP levels were determined at 5 hour. FIG. 10A, ATP—BACTITERGLO® luciferase (100 ul+100 ul culture, 5 min, and luminescence determined). FIG. 10B, ROS—Luminol derivative L-012 (2.5 ul of 20 mM+100 ul culture, 1 min, and luminescence determined).

1 ml of blood spiked with S. aureus, diluted 1:1 with 1×TBST Ca 1% triton
  7 ul of Akt-FcMBL beads (1 uM), added and bacteria captured for 20 mins 4° C.
  Samples washed 1× in TBST Ca 1% triton, 2× in TBST Ca
  Resuspended in 500 ul media, 37° C., at 950 rpm As seen from FIGS. 10A and 10B, both read outs can be used to determine antibiotic susceptibility of bacteria isolated from blood.

Example 6

Antibiotic Susceptibility can be Determined in as Little as 2 Hours

Dilutions of S. aureus or E. coli ($10^{-2}$ fold dilution) were added to 1 ml of heparinized sheep blood, captured by Akt-FcMBL beads, washed and grown in Mueller Hinton broth with or without carbenicillin (100 ug/ml) or Kanamycin (50 ug/ml).
  1 ml of heparinized sheep's blood spiked with S. aureus, and diluted 1:1 with 1×TBST Ca 1% triton
  7 ul of Akt-FcMBL beads (1 uM), added and bacteria captured for 20 minutes
  Samples washed 1× in TBST Ca 1% triton, 2× in TBST Ca
  Resuspended in 500 ul media, 37° C., at 950 rpm
  ATP levels were determined at 2 and 4 hours
  ATP—BACTITERGLO® luciferase (100 ul+100 ul culture, 5 min, and luminescence determined)

As seen from FIGS. 11A-11D, antibiotic susceptibility can be determined in as little as 2 hours. 300 cfu were added and the captured fraction was split into 3 sub fractions. High heparin content allowed splitting of the sample comprising the bead and/or bead-bound pathogen. Without wishing to be bound by a theory, extra heparin can prevent clotting on beads. In addition, addition of extra heparin allows dividing the beads/bugs into multiple samples for testing different antibiotics. Moreover, reproducibility of the assay was improved significantly as compared to FIGS. 11A and 11B Example 7

Culture of Bacteria in the Presence of FcMBL Beads

Bacteria (E. coli and S. aureus) growth was compared in the presence or absence of FcMBL bead.
  10 ul of S. aureus (110000 cfu/ml) or E. coli (90,000 cfu/ml) were added to 1×TBST 5 mM Ca$^{2+}$
  One set of bacteria was captured by 5 ul of FcMBL beads (1 uM), washed once, and resuspended in Mueller Hinton broth
  The second set of bacteria were centrifuged and resuspended in Mueller Hinton broth
  An aliquot of each was plated to determine bacterial growth during capture and wash steps (30 minutes total)
  Bacteria were incubate 4 hours, 37° C., at 950 rpms
  Growth was determined by luminescence read of ATP generation (BACTITERGLO®)

In some embodiments, captured microbes can be maintained on the microbe-targeting substrate during culture. In some embodiments, culturing bacteria in the presence of beads can concentrate bacteria together which may localize growth factors. Alternatively, or in addition, the MBL on the beads could be binding yeast from the media and giving the bacteria higher local concentration of nutrients.

Example 8

50/50 Akt-FcMBL/Heparin Beads Capture Bacteria with the Same Efficiency as Akt-FcMBL Beads Capture efficiency of heparinized beads were determined using rapid ATP quantification assay (BACTITERGLO®).

Figure 12A:
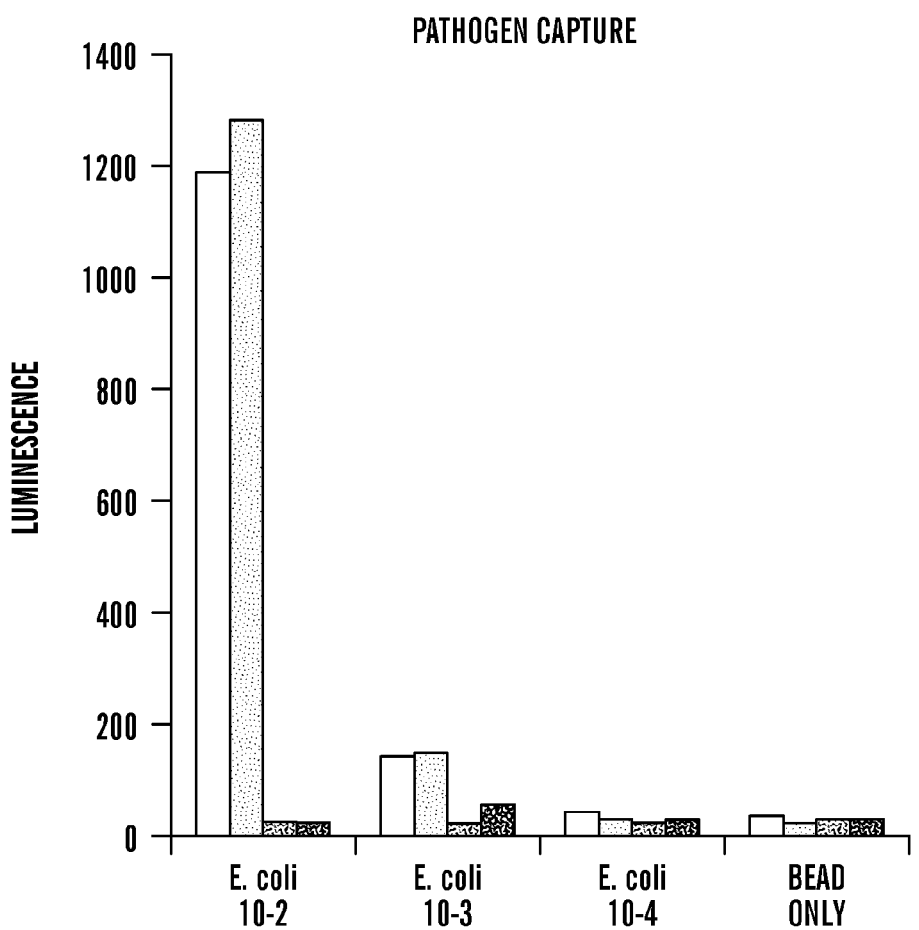
FIGS. 12A and 12B are bar graphs showing 50/50 Akt-FcMBL/Heparin (The beads were coupled to both Akt-FcMBL and heparin using an equimolar mix of biotinylated Akt-FcMBL and biotinylated heparin to generate an estimated 50/50 mix of Akt-FcMBL/heparin on MyONE streptavidin beads [Invitrogen]) beads capture bacteria with the same efficiency as Akt-FcMBL beads. Akt-FcMBL and Akt-FcMBL are described in PCT application no. PCT/US2011, content of which is incorporated herein by reference.
Figure 12B:
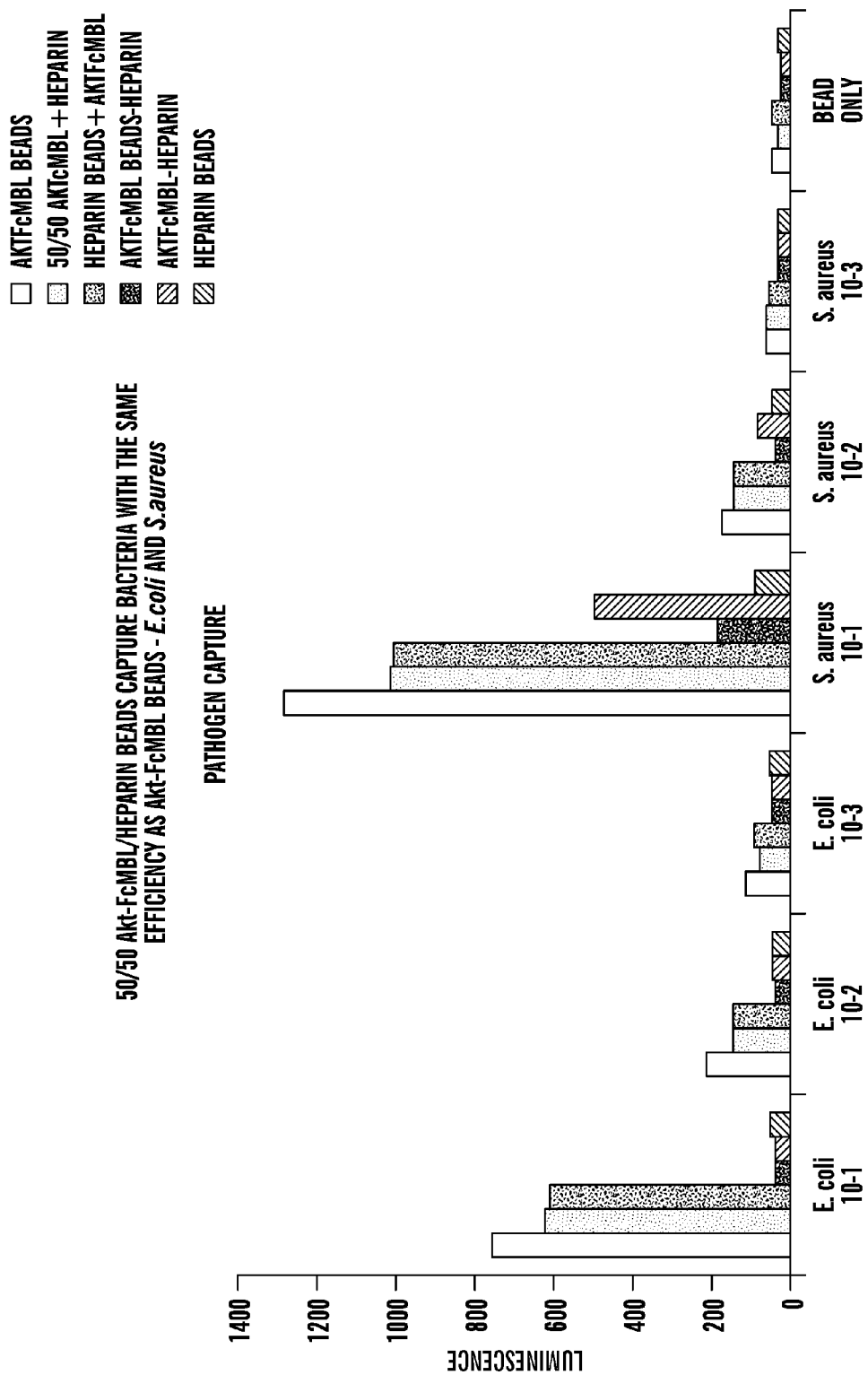

FIG. 12A, Bead 1: Akt-FcMBL; Bead 2:1:1 ratio–Akt-FcMBL: Biotin heparin; Bead 3: Heparin cross-linked to Akt-FcMBL directly; and Bead 4: Heparin only. Capture method:
- 10 ul bacteria spiked into 1 mL TBST comprising $Ca^{2+}$ (TBST-Ca), with 2 ul beads.
- 10 min shake, 900 rpm
- Collect beads on KINGFISHER, wash once in TBST-Ca, resuspend in 100 ul TBST-Ca (working volume for BACTITERGLO®).
- Add 100 ul BACTITERGLO® reagent.
- Read luminescence FIG. 12B, Bead 1: AOB Akt-FcMBLcoupled beads (AOB=aminooxybiotin); Bead 2:1:1 ratio–AOB Akt-FcMBL: Biotin heparin coupled beads; Bead 3: Heparin Beads+AKTFcMBL-1 um beads conjugated with heparin, then coupled with AOB AKT-FcMBL; Bead 4: AKTFcMBL Beads-heparin—Previously coupled AOB AKT-FcMBL beads are conjugated with heparin; Bead 5: Heparin conjugated to Akt-FcMBL directly and coupled to 1 uM beads; and Bead 6: Heparin conjugated beads. Capture method:
- 10 ul bacteria spiked into 1 mL TBST-Ca, with 2 ul beads.
- 10 min shake, 900 rpm
- Collect beads on KINGFISHER, wash once in TBST-Ca, resuspend in 100 ul TBST-Ca (working volume for BACTITERGLO®).
- Add 100 ul BACTITERGLO® reagent.
- Read luminescence Example 9

Antibiotic Susceptibility of Pathogens from Human Blood can be Determined in as Little as 2 Hours Viability of bacteria isolated from human blood was determined using the ATP assay. Dilutions of *S. aureus* or *E. coli* ($10^{-3}$, $10^{-4}$, $10^{-5}$) were added to 1 ml of heparinized blood (1 mg/ml added to blood collected in heparin tube) diluted 1:1 with 1×TBST Ca2+, captured by Akt-FcMBL beads, washed, divided into 4 fractions and grown in 250 µl Mueller Hinton broth with or without Kanamycin (50 ug/ml) 37° C., at 950 rpm. ATP levels were determined at 2 hours using BACTITER-GLO™ luciferase (100 ul+100 ul culture, 5 min), and luminescence determined. Data was plotted as percent of untreated culture ATP levels. As seen from FIGS. 14A-14D, antibiotic susceptibility can be determined in as little as 2 hours. Further, addition of additional heparin allowed splitting of beads following capture in blood.

Example 10

Antibiotic Susceptibility of MRSA, *E. coli* and *S. aureus*

Figure 15B:
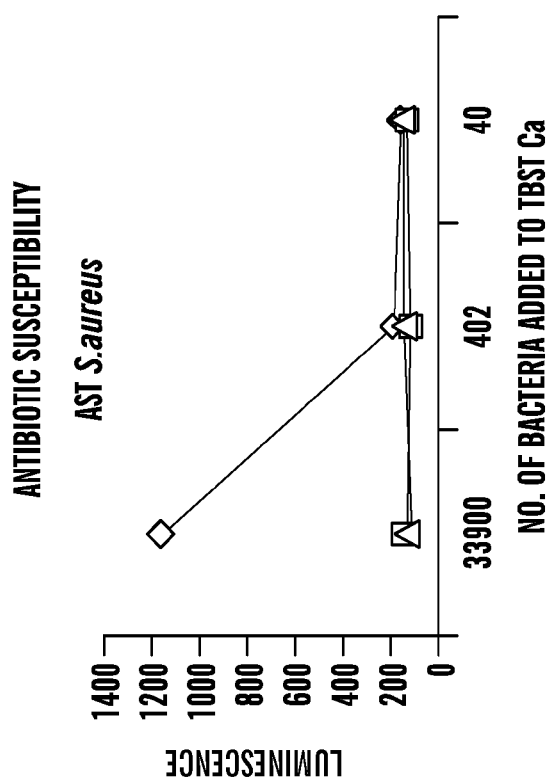
FIGS. 15A-15B are line graphs showing antibiotic susceptibility of $E.\ coli$ (FIG. 15A), and $S.\ aureus$ (FIG. 15B) determined using an embodiment of the assay described herein.
Figure 15A:
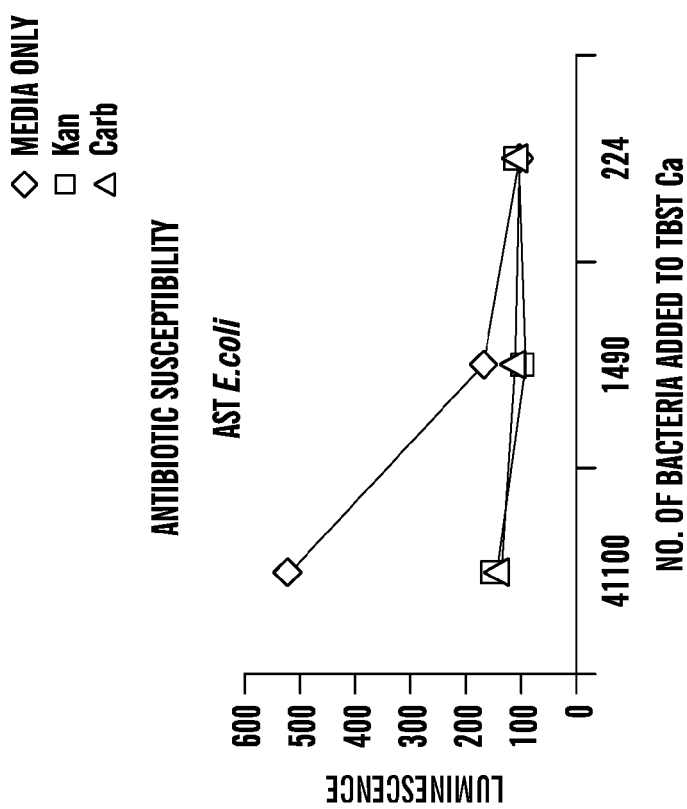

Application of the assay to other bacteria was also determined. Dilutions of bacteria were added to TBST Ca 5 mM. Capture was with 10 µg of AKT-FcMBL 1 µM beads for 10 minutes. Beads were washed 3× in TBST Ca 5 mM and divided. Divided beads were added to Mueller Hinton broth with or without antibiotic (Carb 100 µg/ml, Kan 50 µg/ml). Bacteria were and grown in 96 deep well plate for 2 or 4 hours and bacterial viability determined by luciferase measurement of ATP. As seen in FIGS. 15A-15B, antibiotic susceptibility of *E. coli* and *S. aureus* can be determined using the assay.

Example 11

Rapid Detection of Antibiotic Susceptibility from Single Bacterium

Bacteria in a biological sample were captured by FcMBL coated magnetic beads. The bead/bacteria were washed and added to a microscope compatible surface (for example, plasma treated coverslip or glass bottom microplates) and immobilized by an underlying magnet. A low melt agarose gel 37° C. containing growth media (BHI), resazurin (a stain for labeling live cells), and Sytox Green 11 (a stain for labeling dead cells) was overlaid on the bacteria-bound FcMBL magnetic beads to immobilize and/or secure the bacteria in place. In some embodiments where the bead/bacteria were spotted on glass bottom microplates, the wells were filled with growth medium containing fluorescent stains for live and/or dead cells. The captured bacteria were incubated on the slide or in the wells for about 1-2 hours at about 36-37° C. and imaged by microscopy, e.g., fluorescent microscopy. Live cells could be identified by resorufin (metabolized resazurin) stain and coordinates of the live cells could be determined and stored for iterative imaging. An antibiotic agent (e.g., kanamycin at 50 µg/ml) in growth media (e.g., BHI) containing live-dead stain was added. Bacteria can be observed for, for example, growth in the presence of the antibiotics (to determine the resistance of the bacteria to the particular antibiotics), cell death determined by fluorescent stain for dead cells (to determine bactericidal activity), and/or inhibition of growth (to determine bacteriostatic activity). For example, bacteria were examined for Sytox green staining (switching from red-resorufin to green—the Sytox green 11 entry into the cell as a measure of cell death). The captured *E. coli* grown in the gel matrix demonstrated a reaction to the Kanamycin addition. For example, a color change from red-resorufin to green—the Sytox green 11 was observed for some of the bacteria within 5 minutes and a complete effect within 30-40 minutes for all cells in the tracked fields of vision (FIG. 16).

The process described herein allows the detection of resistance to kanamycin without previous culture in a time frame of ~120-~150 minutes. Different embodiments of the assay or process described herein can be used with other classes of antimicrobial agents, and thus provide major clinical significance and revolutionize the field of clinical microbiology and infectious diseases management.

An exemplary method for detection of antibiotic susceptibility from individual bacteria (FIG. 16) is shown below:
- Bacteria (e.g., *E. coli*) in a biological sample (or about 10 µL of TBST containing 5 mM $Ca^{2+}$ washed *E. coli*) can be captured by about 1 µM FcMBL Beads (10 µl of about 1 mg/ml FcMBL beads) added in 1 about 1 mL TBST containing 5 mM $Ca^{2+}$ (capture time: ~10 min).
- The captured bacteria is washed at least 2 times with TBST containing 5 mM $Ca^{2+}$
- The washed bacteria is resuspended in about 100 µl TBST containing 5 mM $Ca^{2+}$ (2 can be used per coverslip spot)

One or more coverslips are set up

Coverslips are plasma treated for 60 sec to increase gel adhesion.

~2 µl of bead-captured *E. coli* are spotted on the coverslip and held in place by an underlying magnet 3% NUSIEVE® gel in 50% TBST-$Ca^{2+}$/50% growth medium (e.g., BHI broth) with 20 µM resazurin and 5 µM Sytox Green 11 is overlaid on the bead-captured *E. coli* and allowed to set.

Captured bacteria are incubated at 37° C. for about 1 hour and imaged on SP5 confocal microscope 40× at 37° C.

Live bacteria are located by Alamar BLUE®[reduction of resazurin to resorufin (560 nm excitation/590 nm emission)]

An antibiotic agent (e.g., Kanamycin) is added at a concentration in the medium (BHI containing resazurin-Sytox green) of about 50 mg/L.

Bacteria is imaged for acquisition of Sytox green

The method can be applied to one or multiple pathogens and one or multiple antimicrobial agents. Bacterial growth can be observed in real time and the identity of the pathogen is not required. The pathogen grown in an antimicrobial-free media can be isolated from the gel and used for identification (for example, but not limited to, MALDI-TOF mass spectroscopy), leading to rapid identification as well as antibiotic susceptibility.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

---

What is claimed is:

1. A method for determining antibiotic susceptibility of a microbe, the method comprising:
   (i) obtaining a sample comprising a microbe, wherein the microbe is bound to a microbe-targeting substrate, wherein the microbe-targeting substrate comprises a solid substrate and a microbe-binding molecule on a surface of the solid substrate, wherein the microbe-binding molecule comprises at least one carbohydrate recognition domain and N-terminus of the microbe-binding molecule is linked to the solid substrate;
   (ii) incubating the solid substrate-bound microbe in the presence of at least one antibiotic agent for a pre-determined period of time; and
   (iii) detecting the growth, viability, or functional response of the microbe to the antibiotic agent,
   wherein reduced growth, viability, or function in the presence of the antibiotic agent relative to a reference or control sample indicates that the microbe is susceptible to the antibiotic agent.

2. The method of claim 1, wherein the sample comprising the solid substrate-bound microbe is obtained by contacting a test sample suspected of comprising a microbe with the microbe-targeting substrate.

3. The method of claim 1, wherein the solid substrate is selected from the group consisting of nucleic acid scaffolds, protein scaffolds, lipid scaffolds, dendrimers, nanoparticles, microparticles, microtiter plates, filters, fibers, screens, tubes, nanotubes, magnetic particles, microfluidic channels, membranes, microchips, filtration devices, diagnostic strips, dipsticks, extracorporeal devices, spiral mixers, hollow fibers, and any combination thereof.

4. The method of claim 3, wherein the microbe-targeting substrate comprises magnetic particles.

5. The method of claim 1, wherein the carbohydrate recognition domain comprises at least a microbial-binding portion of C-type lectins, collectins, ficolins, receptor-based lectins, lectins from the shrimp Marsupenaeus japonicas, non-C-type lectins, lipopolysaccharide (LPS)-binding proteins, endotoxin-binding proteins, peptidoglycan-binding proteins, or any combinations thereof.

6. The method of claim 5, wherein the carbohydrate recognition domain comprises at least a microbial-binding portion of mannan-binding lectin (MBL), surfactant protein A, surfactant protein D, collectin 11, L-ficolin, ficolin A, DC-SIGN, DC-SIGNR, SIGNR1, macrophage mannose receptor 1, dectin-1, dectin-2, lectin A, lectin B, lectin C, wheat germ agglutinin, CD14, MD2, lipopolysaccharide-binding protein (LBP), limulus anti-LPS factor (LAL-F), mammalian peptidoglycan recognition protein-1 (PGRP-1), PGRP-2, PGRP-3, PGRP-4, or any combinations thereof.

7. The method of claim 1, wherein the microbe-binding molecule is attached to the surface of the solid substrate through a linker.

8. The method of claim 7, wherein N terminus of the linker comprises an amino acid sequence of AKT (alanine, lysine, threonine).

9. The method of claim 7, wherein the linker comprises a Fc portion of an immunoglobulin.

10. The method of claim 1, wherein the microbe-binding molecule is selected from the group consisting of MBL (mannose binding lectin), FcMBL (IgG Fc fused to mannose binding lectin), AKT-FcMBL (IgG Fc-fused to mannose binding lectin with the N-terminal amino acid tripeptide of sequence AKT (alanine, lysine, threonine)), and any combination thereof.

11. The method of claim 1, wherein the microbe-binding molecule comprises an amino acid sequence selected from SEQ ID NO. 1, SEQ ID NO. 2, SEQ ID NO. 3, SEQ ID NO. 4, SEQ ID NO. 5, SEQ ID NO. 6, SEQ ID NO. 6, SEQ ID NO. 7, SEQ ID NO. 8, and any combination thereof.

12. The method of claim 2, wherein the test sample is a biological fluid obtained or derived from a subject, a fluid or specimen obtained from an environmental source, a fluid from a cell culture, a microbe colony, or any combinations thereof.

13. The method of claim 1, wherein the test sample is a biological fluid selected from blood, plasma, serum, lactation products, amniotic fluids, sputum, saliva, urine, semen, cerebrospinal fluid, bronchial aspirate, bronchial lavage aspirate fluid, perspiration, mucus, liquefied stool sample, synovial fluid, peritoneal fluid, pleural fluid, pericardial fluid, lymphatic fluid, tears, tracheal aspirate, a homogenate of a tissue specimen, or any mixtures thereof.

14. The method of claim 1, wherein the test sample is a fluid or specimen obtained from an environmental source selected from a fluid or specimen obtained or derived from food products, food produce, poultry, meat, fish, beverages, dairy product, water (including wastewater), ponds, rivers, reservoirs, swimming pools, soils, food processing and/or packaging plants, agricultural places, hydrocultures (including hydroponic food farms), pharmaceutical manufacturing plants, animal colony facilities, or any combinations thereof.

15. The method of claim 1, wherein said detecting the growth, viability, or functional response of the microbe is by an assay selected from the group consisting of cytolysis, membrane leakage, mitochondrial activity, caspase assays, Reactive Oxygen Species (ROS) production, ATP production, pH, genomic, metabolomic, transcriptomic, proteomic assays, and any combinations thereof.

16. The method of claim 1, wherein said detecting the growth, viability, or functional response of the microbe comprises ELISA, optical or microscopic imaging, flow cytometry, mass spectrometry, PCR, luminescence or fluorescence labeling, or any combinations thereof.

17. The method of claim 1, wherein the solid substrate-bound microbe from step (i) is immobilized in a gel matrix, prior to the incubation in the presence of at least one antibiotic agent.

18. The method of claim 17, wherein the gel matrix is reactive to the growth, viability, or functional response of the microbe immobilized in the gel matrix.

19. The method of claim 17, wherein the gel matrix comprises at least one detection agent to determine at least metabolism or viability of the microbe in the matrix.

20. The method of claim 19, wherein said at least one detection agent is selected from the group consisting of resazurin or molecules derived from a nucleic acid binding agent, calcein AM, a tetrazolium salt, a protease marker, a pH indicator, an ATP indicator, a redox indicator, an esterase indicator, an ROS indicator, a cell-permeable dye, Carboxylic Acid Diacetate, Succinimidyl Ester, a cell-impermeable dye, cyanine, phenantridines, acridines, indoles, imidazoles, a nucleic acid stain, a cell permeant reactive tracer, intracellularly-activated fluorescent dyes, CMRA, $CMF_2HC$ (4-Chloromethyl-6,8-Difluoro-7-Hydroxycoumarin), CMFDA (5-Chloromethylfluorescein Diacetate), CMTMR (5-(and-6)-(((4-Chloromethyl)Benzoyl)Amino)Tetramethylrhodamine), CMAC (7-Amino-4-Chloromethylcoumarin), CMHC (4-Chloromethyl-7-Hydroxycoumarin)), fluorescent DNA dyes, DAPI, Heochst family, SYBR family, SYTO family, SYTO 9, SYTOX family, SYTOX green, ethidium bromide, propidium iodide, acridines, chromogenic dyes, eosin, hematoxilin, methylene blue, azure, cytoplasma stain, calcofluor white, periodic acid-schiff stain, metabolic stains, any diacetate dye, rhodamine based-dye, fluorescin, resazurin/resorufin (alamar blue), ROS stains, DCFDA and related family, calcein-acetoxymethyl and related family, membrane stains, bodipy, FM 1-43, FM 4-64, DiI, DiO, DiA, biologic stains, labeled antibodies, labeled chitin-binding protein, and any combinations thereof.

21. The method of claim 17, wherein the gel matrix is selected from a group consisting of an agarose gel, a collagen gel, a matrigel, an alginate gel, a biocompatible polymer gel, a hydrogel, gelatin, a fibrin gel, and any combinations thereof.

22. The method of claim 19, wherein said detecting the growth, viability, or functional response of the microbe comprises imaging the microbe for a detectable signal change in the detection agent, thereby providing a real time and/or single cell antibiotic susceptibility analysis.

23. The method of claim 1, wherein total time for steps (i)-(iii) is less than 6 hours.

24. The method of claim 1, wherein the determined antibiotic susceptibility of the microbe identifies an effective antimicrobial treatment without first identifying the microbe.

25. The method of claim 1, wherein the method excludes a culturing step for cell expansion prior to the incubation in the presence of said at least one antibiotic agent.

26. The method of claim 1, further comprising determining identity of the microbe by subjecting the solid substrate-bound microbe that is untreated with said at least one antibiotic agent to mass spectrometry or surface enhanced Raman spectroscopy or nucleic acid amplification or hybridization or any combinations thereof.

* * * * *

SEQUENCE LISTING

```
<160> NUMBER OF SEQ ID NOS: 8

<210> SEQ ID NO 1
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ser Leu Phe Pro Ser Leu Pro Leu Leu Leu Ser Met Val Ala
1               5                   10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
                35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220
```

```
Leu Leu Lys Asn Gly Gln Trp Asn Asp Val Pro Cys Ser Thr Ser His
225                 230                 235                 240

Leu Ala Val Cys Glu Phe Pro Ile
                245
```

<210> SEQ ID NO 2
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Glu Thr Val Thr Cys Glu Asp Ala Gln Lys Thr Cys Pro Ala Val Ile
1               5                   10                  15

Ala Cys Ser Ser Pro Gly Ile Asn Gly Phe Pro Gly Lys Asp Gly Arg
            20                  25                  30

Asp Gly Thr Lys Gly Glu Lys Gly Glu Pro Gly Gln Gly Leu Arg Gly
        35                  40                  45

Leu Gln Gly Pro Pro Gly Lys Leu Gly Pro Pro Gly Asn Pro Gly Pro
    50                  55                  60

Ser Gly Ser Pro Gly Pro Lys Gly Gln Lys Gly Asp Pro Gly Lys Ser
65                  70                  75                  80

Pro Asp Gly Asp Ser Ser Leu Ala Ala Ser Glu Arg Lys Ala Leu Gln
                85                  90                  95

Thr Glu Met Ala Arg Ile Lys Lys Trp Leu Thr Phe Ser Leu Gly Lys
            100                 105                 110

Gln Val Gly Asn Lys Phe Phe Leu Thr Asn Gly Glu Ile Met Thr Phe
        115                 120                 125

Glu Lys Val Lys Ala Leu Cys Val Lys Phe Gln Ala Ser Val Ala Thr
    130                 135                 140

Pro Arg Asn Ala Ala Glu Asn Gly Ala Ile Gln Asn Leu Ile Lys Glu
145                 150                 155                 160

Glu Ala Phe Leu Gly Ile Thr Asp Glu Lys Thr Glu Gly Gln Phe Val
                165                 170                 175

Asp Leu Thr Gly Asn Arg Leu Thr Tyr Thr Asn Trp Asn Glu Gly Glu
            180                 185                 190

Pro Asn Asn Ala Gly Ser Asp Glu Asp Cys Val Leu Leu Leu Lys Asn
        195                 200                 205

Gly Gln Trp Asn Asp Val Pro Cys Ser Thr Ser His Leu Ala Val Cys
    210                 215                 220

Glu Phe Pro Ile
225
```

<210> SEQ ID NO 3
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Ala Ala Ser Glu Arg Lys Ala Leu Gln Thr Glu Met Ala Arg Ile Lys
1               5                   10                  15

Lys Trp Leu Thr Phe Ser Leu Gly Lys Gln Val Gly Asn Lys Phe Phe
            20                  25                  30
```

```
Leu Thr Asn Gly Glu Ile Met Thr Phe Glu Lys Val Lys Ala Leu Cys
         35                  40                  45

Val Lys Phe Gln Ala Ser Val Ala Thr Pro Arg Asn Ala Ala Glu Asn
 50                  55                  60

Gly Ala Ile Gln Asn Leu Ile Lys Glu Glu Ala Phe Leu Gly Ile Thr
 65                  70                  75                  80

Asp Glu Lys Thr Glu Gly Gln Phe Val Asp Leu Thr Gly Asn Arg Leu
                 85                  90                  95

Thr Tyr Thr Asn Trp Asn Gly Glu Pro Asn Asn Ala Gly Ser Asp
             100                 105                 110

Glu Asp Cys Val Leu Leu Leu Lys Asn Gly Gln Trp Asn Asp Val Pro
         115                 120                 125

Cys Ser Thr Ser His Leu Ala Val Cys Glu Phe Pro Ile
130                 135                 140

<210> SEQ ID NO 4
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Val Gly Asn Lys Phe Phe Leu Thr Asn Gly Glu Ile Met Thr Phe Glu
 1               5                  10                  15

Lys Val Lys Ala Leu Cys Val Lys Phe Gln Ala Ser Val Ala Thr Pro
             20                  25                  30

Arg Asn Ala Ala Glu Asn Gly Ala Ile Gln Asn Leu Ile Lys Glu Glu
         35                  40                  45

Ala Phe Leu Gly Ile Thr Asp Glu Lys Thr Glu Gly Gln Phe Val Asp
     50                  55                  60

Leu Thr Gly Asn Arg Leu Thr Tyr Thr Asn Trp Asn Gly Glu Pro
 65                  70                  75                  80

Asn Asn Ala Gly Ser Asp Glu Asp Cys Val Leu Leu Leu Lys Asn Gly
                 85                  90                  95

Gln Trp Asn Asp Val Pro Cys Ser Thr Ser His Leu Ala Val Cys Glu
            100                 105                 110

Phe Pro Ile
        115

<210> SEQ ID NO 5
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Pro Asp Gly Asp Ser Ser Leu Ala Ala Ser Glu Arg Lys Ala Leu Gln
 1               5                  10                  15

Thr Glu Met Ala Arg Ile Lys Lys Trp Leu Thr Phe Ser Leu Gly Lys
             20                  25                  30

Gln Val Gly Asn Lys Phe Phe Leu Thr Asn Gly Glu Ile Met Thr Phe
         35                  40                  45

Glu Lys Val Lys Ala Leu Cys Val Lys Phe Gln Ala Ser Val Ala Thr
     50                  55                  60
```

Pro Arg Asn Ala Ala Glu Asn Gly Ala Ile Gln Asn Leu Ile Lys Glu
65                  70                  75                  80

Glu Ala Phe Leu Gly Ile Thr Asp Glu Lys Thr Glu Gly Gln Phe Val
                85                  90                  95

Asp Leu Thr Gly Asn Arg Leu Thr Tyr Thr Asn Trp Asn Glu Gly Glu
            100                 105                 110

Pro Asn Asn Ala Gly Ser Asp Glu Asp Cys Val Leu Leu Leu Lys Asn
        115                 120                 125

Gly Gln Trp Asn Asp Val Pro Cys Ser Thr Ser His Leu Ala Val Cys
130                 135                 140

Glu Phe Pro Ile
145

<210> SEQ ID NO 6
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Ala Pro Asp Gly Asp Ser Ser Leu Ala
225                 230                 235                 240

Ala Ser Glu Arg Lys Ala Leu Gln Thr Glu Met Ala Arg Ile Lys Lys
                245                 250                 255

Trp Leu Thr Phe Ser Leu Gly Lys Gln Val Gly Asn Lys Phe Phe Leu
            260                 265                 270

```
Thr Asn Gly Glu Ile Met Thr Phe Glu Lys Val Lys Ala Leu Cys Val
            275                 280                 285

Lys Phe Gln Ala Ser Val Ala Thr Pro Arg Asn Ala Ala Glu Asn Gly
290                 295                 300

Ala Ile Gln Asn Leu Ile Lys Glu Ala Phe Leu Gly Ile Thr Asp
305                 310                 315                 320

Glu Lys Thr Glu Gly Gln Phe Val Asp Leu Thr Gly Asn Arg Leu Thr
                325                 330                 335

Tyr Thr Asn Trp Asn Glu Gly Glu Pro Asn Asn Ala Gly Ser Asp Glu
            340                 345                 350

Asp Cys Val Leu Leu Lys Asn Gly Gln Trp Asn Asp Val Pro Cys
            355                 360                 365

Ser Thr Ser His Leu Ala Val Cys Glu Phe Pro Ile
    370                 375                 380

<210> SEQ ID NO 7
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Pro Asp Gly Asp Ser
225                 230                 235                 240

Ser Leu Ala Ala Ser Glu Arg Lys Ala Leu Gln Thr Glu Met Ala Arg
                245                 250                 255
```

```
Ile Lys Lys Trp Leu Thr Phe Ser Leu Gly Lys Gln Val Gly Asn Lys
            260                 265                 270

Phe Phe Leu Thr Asn Gly Glu Ile Met Thr Phe Glu Lys Val Lys Ala
        275                 280                 285

Leu Cys Val Lys Phe Gln Ala Ser Val Ala Thr Pro Arg Asn Ala Ala
    290                 295                 300

Glu Asn Gly Ala Ile Gln Asn Leu Ile Lys Glu Ala Phe Leu Gly
305                 310                 315                 320

Ile Thr Asp Glu Lys Thr Glu Gly Gln Phe Val Asp Leu Thr Gly Asn
                325                 330                 335

Arg Leu Thr Tyr Thr Asn Trp Asn Glu Gly Glu Pro Asn Asn Ala Gly
            340                 345                 350

Ser Asp Glu Asp Cys Val Leu Leu Leu Lys Asn Gly Gln Trp Asn Asp
        355                 360                 365

Val Pro Cys Ser Thr Ser His Leu Ala Val Cys Glu Phe Pro Ile
    370                 375                 380

<210> SEQ ID NO 8
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Thr Ser Lys Gln Val Gly Asn Lys
225                 230                 235                 240
```

```
                        -continued
Phe Phe Leu Thr Asn Gly Glu Ile Met Thr Phe Glu Lys Val Lys Ala
                245             250                 255

Leu Cys Val Lys Phe Gln Ala Ser Val Ala Thr Pro Arg Asn Ala Ala
            260             265                 270

Glu Asn Gly Ala Ile Gln Asn Leu Ile Lys Glu Glu Ala Phe Leu Gly
        275                 280                 285

Ile Thr Asp Glu Lys Thr Glu Gly Gln Phe Val Asp Leu Thr Gly Asn
    290                 295                 300

Arg Leu Thr Tyr Thr Asn Trp Asn Glu Gly Glu Pro Asn Asn Ala Gly
305                 310                 315                 320

Ser Asp Glu Asp Cys Val Leu Leu Leu Lys Asn Gly Gln Trp Asn Asp
                325             330                 335

Val Pro Cys Ser Thr Ser His Leu Ala Val Cys Glu Phe Pro Ile
                340             345                 350
```